(12) United States Patent
Walensky et al.

(10) Patent No.: US 11,220,532 B2
(45) Date of Patent: Jan. 11, 2022

(54) TARGETING DEREGULATED WNT SIGNALING IN CANCER USING STABILIZED ALPHA-HELICES OF BCL-9

(71) Applicant: DANA-FARBER CANCER INSTITUTE, INC., Boston, MA (US)

(72) Inventors: Loren D. Walensky, Newton, MA (US); Ruben Carrasco, Brookline, MA (US); Gregory H. Bird, Pelham, NH (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/876,779

(22) Filed: May 18, 2020

(65) Prior Publication Data

US 2021/0002336 A1    Jan. 7, 2021

Related U.S. Application Data

(62) Division of application No. 14/111,299, filed as application No. PCT/US2012/033822 on Apr. 16, 2012, now Pat. No. 10,703,785.

(60) Provisional application No. 61/475,932, filed on Apr. 15, 2011.

(51) Int. Cl.
| | |
|---|---|
| *C07K 14/47* | (2006.01) |
| *C07K 14/82* | (2006.01) |
| *A61K 38/17* | (2006.01) |
| *A61K 45/06* | (2006.01) |
| *G01N 33/53* | (2006.01) |
| *A61K 38/00* | (2006.01) |

(52) U.S. Cl.
CPC .......... *C07K 14/47* (2013.01); *A61K 38/1709* (2013.01); *A61K 45/06* (2013.01); *C07K 14/82* (2013.01); *G01N 33/53* (2013.01); *A61K 38/00* (2013.01)

(58) Field of Classification Search
None
See application file for complete search history.

(56) References Cited

U.S. PATENT DOCUMENTS

| | | |
|---|---|---|
| 7,084,244 B2 | 8/2006 | Gilon et al. |
| 7,192,713 B1 | 3/2007 | Verdine et al. |
| 7,723,469 B2 | 5/2010 | Walensky et al. |
| 10,703,785 B2 | 7/2020 | Walensky et al. |
| 2002/0086986 A1 | 7/2002 | Basler et al. |
| 2005/0250680 A1 | 11/2005 | Walensky et al. |
| 2006/0008848 A1 | 1/2006 | Verdine et al. |
| 2006/0014675 A1 | 1/2006 | Arora et al. |
| 2007/0197772 A1 | 8/2007 | Arora et al. |
| 2010/0234563 A1 | 9/2010 | Arora et al. |
| 2014/0113857 A1 | 4/2014 | Walensky et al. |

FOREIGN PATENT DOCUMENTS

| | | |
|---|---|---|
| CN | 1852974 A | 10/2006 |
| CN | 1906209 A | 1/2007 |
| EP | 1997828 A2 | 12/2008 |
| WO | 2005005601 A2 | 1/2005 |
| WO | 2005/044839 A3 | 5/2005 |
| WO | 2008/121767 A2 | 10/2008 |
| WO | 2009/108261 A2 | 9/2009 |
| WO | 2010/148335 A2 | 12/2010 |
| WO | 2011/008260 A2 | 1/2011 |

OTHER PUBLICATIONS

National Cancer Institute (<https://www.cancer.gov/about-cancer/understanding/what-is-cancer> accessed Apr. 19, 2021).*
American Association of Neurological Surgeons (https://www.aans.org/en/Patients/Neurosurgical-Conditions-and-Treatments/Brain-Tumors accessed Apr. 19, 2021).*
Mani et al. ("BCL9 promotes Tumor progression by conferring enhanced proliferative, metastatic and angiogenic properties to cancer cells" Cancer Research, Oct. 2009; vol. 69 (19)).*
Barker, N. et al., "Mining the Wnt pathway for cancer therapeutics", Nat Rev Drug Discov, 2006, 5:997-1014.
Basu, A. et al., "Overexpression of Vascular Endothelial Growth Factor and the Development of Post-Transplantation", Cancer Res., 2008, 68(14):5689-5698.
Bird, G. H., et al., "Chapter 22 Synthesis and Biophysical Characterization of Stabilized a-Helices of BCL-2 Domains", Methods in Enzymology, 2008, 446:369-386.
Bird, G.H et al., "Hydrocarbon double-stapling remedies the proteolytic instability of a lengthy peptide therapeutic", 2010, 107(32):14093-14098.
Bolstad, B. M., et al., "A comparison of normalization methods for high density oligonucleotide array data based on variance and bias," Bioinformatics, 2003, 19(2):185-193.
Brembeck, F. H et al., "Essential role of BCL9-2 in the switch between β-catenin's adhesive and transcriptional functions", Genes Dev, 2004, 18:2225-2230.

(Continued)

*Primary Examiner* — James H Alstrum-Acevedo
*Assistant Examiner* — Tara L Martinez
(74) *Attorney, Agent, or Firm* — Fish & Richardson P.C.

(57) ABSTRACT

The invention provides structurally-constrained peptides by hydrocarbon stapling of a BCL9 HD2 helix for use as a therapeutic agent. The invention further provides methods and kits for use of the structurally-constrained peptide of the instant invention. The invention is based, at least in part, on the results provided herein demonstrating that hydrocarbon stapled helical peptides display excellent proteolytic, acid, and thermal stability, restore the native helical structure of the peptide, possess superior pharmacokinetic properties compared to the corresponding unmodified peptides, and are highly effective in binding to β-catenin in vitro, in cellulo, and in vivo, disrupting the BCL9/β-catenin interaction, and thereby interfering with deregulated Wnt/β-catenin signaling for therapeutic benefit in a variety of human diseases including human cancer.

17 Claims, 41 Drawing Sheets
Specification includes a Sequence Listing.

(56) References Cited

OTHER PUBLICATIONS

Chapman, R.N. et al., "A Highly Stable Short α-Helix Constrained by a Main-Chain Hydrogen-Bond Surrogate", J. Am. Chem. Soc, 2004, 126(39):12252-12253.
Chittenden, T., et al., "A conserved domain in Bak, distinct from BH1 and BH2, mediates cell death and protein binding functions", Embo Journal, 1995, 14(22):5589-5596.
Clevers, H.,"Wnt β Catenin Signaling in Development and Disease", Cell, 2006,127(3):469-480.
Dejana, E., "The Role of Wnt Signaling in Physiological and Pathological Angiogenesis", Circulation Research, 2010, 107:943-952.
Deka, J. et al., "Bcl9/Bcl9l are Critical for Wnt-Mediated Regulation of Stem Cell Traits in Colon Epithelium and Adenocarcinomas", Cancer Res, 2010, 70:6619-6628.
Ellenberger, T.E., et al., "The GCN4 basic region leucine zipper binds DNA as a dimer of uninterrupted α Helices Crystal structure of the protein-DNA complex Cell", 1992, 71(7):1223-1237.
Ilyas, M., et al., "β-Catenin mutations in cell lines established from human colorectal cancers", Proc Natl Acad Sci USA, 1997, 94(19):10330-10334.
Kawamoto, S.A et al., "Design of Triazole-Stapled BCL9 α-Helical Peptides to Target the β-Catenin/B-Cell CLL/lymphoma9 (BCL9) Protein-Protein Interaction", Journal of Medicinal Chemistry, 2011, 55:1137-1146.
Kawamoto, "Targeting the BCL9/B9L Binding Interaction with Beta-catenin as a Potential Anticancer Strategy", Ph. D. Thesis, 2010, University of Michigan.
Kim et al., "Introduction of All-Hydrocarbon I, i+3 staples into a-helices via Ring-closing Olefin Metathesis", Organic Letters, 2010, 12(13):3046-3049.
Klaus, A., et al., "Wnt signaling and its impact on development and cancer", Nat Rev Cancer, 2008, 8:387-398.
Kussie, P.H., et al., "Structure of the MDM2 Oncoprotein Bound to the p53 Tumor Suppressor Transactivation Domain", Science, 1996, 274(5289):948-953.
Lepourcelet, M. et al., "Small-molecule antagonists of the oncogenic Tcf β-catenin protein complex", Cancer Cell, 2004, 5(1):91-102.
Liu, et al., "Engineering a tRNA and aminoacyl-tRNA synthetase for the site-specific incorporation of unnatural amino acids into proteins in vivo", Proc. Nat. Acad. Sci (USA), 1997, 94:10092-10097.
Logan, C. Y., et al., "The Wnt Signaling Pathway in Development and Disease", Rev Cell Dev Biol, 2004, 20: 781-810.
Lupas, A., et al., "Predicting coiled coils from protein sequences", Science, 1991, 252(5009):1162-1164.
Mahon, A.B., et al., "Design synthesis and protein-targeting properties of thioether-linked hydrogen bond surrogate helices", Chem. Commun, 2012, 48(10): 1416-1418.
Mani, M., et al., "BCL9 Promotes Tumor Progression by Conferring Enhanced Proliferative, Metastatic, and Angiogenic Properties to Cancer Cells", Cancer Res, 2009, 69:7577-86.
McCarthy, D. J. et al., "Testing significance relative to a fold-change threshold is a TREAT", Bioinformatics, 2009, 25(6)765-771.
Naldini, et al., PNAS, 1996 Efficient transfer, integration, and sustained long-term expression of the transgene in adult rat brains injected with a lentiviral vector.
Pitter, K. et al., Chapter 23 Dissection of the BCL-2 Family Signaling Network with Stabilized α-Helices of BCL-2 Domains Methods Enzymol, 2008, 446:387-408.
Sampietro, J et al., "Crystal Structure of a I3-Catenin BCL9 Tcf4 Complex" Mol Cell, 2006, 24: 293-300.
Schafmeisitter, C., et al., "An All-Hydrocarbon Cross-Linking System for Enhancing the Helicity and Metabolic Stability of Peptides," Chem Soc, 2000, 122:5891-5892.
Shang, Y., et al., "Cofactor Dynamics and Sufficiency in Estrogen Receptor—Regulated Transcription" Cell, 2000, 103, 843-52.
Smyth, G. K., "Linear Models and Empirical Bayes Methods for Assessing Differential Expression in Microarray Experiments", Statistical Applications in Genetics and Molecular Biology, 2004, vol. 3, Issue 1, Article 3.
Subramanian, A. et al., "Gene set enrichment analysis a knowledge-based approach for interpreting genome-wide expression profiles". Proc Natl Acad Sci USA, 2005, 102:15545-50.
Sukhdeo, K. et al., "Targeting the beta-catenin TCF transcriptional complex in the treatment of multiple myeloma", Proc Natl Acad Sci USA, 2007, 104:7516-21.
Sustmann, C., et al., Cell-Type-Specific Function of BCL9 Involves a Transcriptional Activation Domain That Synergizes with I3-Catenin Mol Cell Biol, 2008,28:3526-37.
Takada, Kohichi et al., "Targeted Disruption of the BCL9/β Catenin Complex Inhibits Oncogenic Wnt Signaling", Science Translational Medicine, 2012, 4(148), pp. 148ra117.
Tassone, P. et al., "A clinically relevant SCID-hu in vivo model of human multiple myeloma", Blood, 2005,106(2): 713-716.
L. G. Van der Flier et al., "The Intestinal Wnt/TCF Signature", Gastroenterology, 2007,132(2):628-632.
Vermeulen L., et al., "Wnt activity defines colon cancer stem cells and is regulated by the microenvironment", Nat Cell Biol, 2010, 12:468.
Walensky, L. D., et al., "Activation of Apoptosis in Vivo by a Hydrocarbon-Stapled BH3 Helix", Science, 2004, 305:1466-70.
Walensky et al., "Hydrocarbon-stapled peptides: principles, practice, and progress", J Med Chem, 2014, 57(15):6275-88.
Cooke, Robert, "Anticancer drugs are not enough to conquer cancer", 2001, Shanghai People's Publishing House. Dr. Folkman's War: Angiogenesis and the Struggle to Defeat Cancer.
Shuai, W., et al., "Research on BCL9 with Tumor and Tumor Target Treatment", Life Science Research, 2013, 17(1):86-89.
Bernal et al.. "Reactivation of the p53 tumor suppressor pathway by a stapled p53 peptide," J Am Chem Soc, 2007, 129(9):2456-7.
Chan et al., "Targeted inactivation of CTNNBI reveals unexpected effects of beta-catenin mutation," Proc Natl Acad Sci USA, Jun. 2002, 99(12):8265-70.
Extended European Search Report in European U.S. Appl. No. 12/771,731 2, dated Nov. 6, 2014, 3 pages.
Extended European Search Report in European Appln. No. 18164082.2, dated May 15, 2018, 6 pages.
Extended European Search Report in European Appln. No. 20172306.1, dated Jul. 28, 2020, 2 pages.
Gsea-msigdb.org, "UCSan Diego Overview," 2020, retrieved on Feb. 10, 2021, retrieved from URL<https://www.gsea-msigdb.org/gsca/index.jsp>, 1 page.
Mollering et al., "Direct inhibition of the NOTCH transcription factor complex," Nature, 2009, 462(7270): 182-8.
Ncbi.nlm.nih.gov, "Gene Expression Omnibus," 2020, retrieved on Feb. 10, 2021, retrieved from URL<https://www.ncbi.nlm.nih.gov/geo/>, 1 page.
PCT International Preliminary Report on Patentability in International Appln. No. PCT/US2012/033822, dated Oct. 15, 2013, 8 pages.
PCT International Search Report and Written Opinion in International Appln. No. PCT/US2012/033822, dated Nov. 8, 2012, 11 pages.
Synthetic Peptides a User's Guide, 2nd Ed., 2002, Chapter 3, 139 pages.

\* cited by examiner

BCL9 HD2    $_{352}$LSQEQLEHRERSLQTLRDIQRMLE$_{374}$    (SEQ ID NO: 1)

SAH-BCL9$_A$    LSQEQLEHRERSLQTLR⊗IQR⊗LF    (SEQ ID NO: 3)

SAH-BCL9$_B$    LSQEQLEHRERSL⊗TLR⊗IQRBLF    (SEQ ID NO: 4)

SAH-BCL9$_C$    LSQEQLEHRE⊗SLQ⊗LRDIQRBLF    (SEQ ID NO: 5)

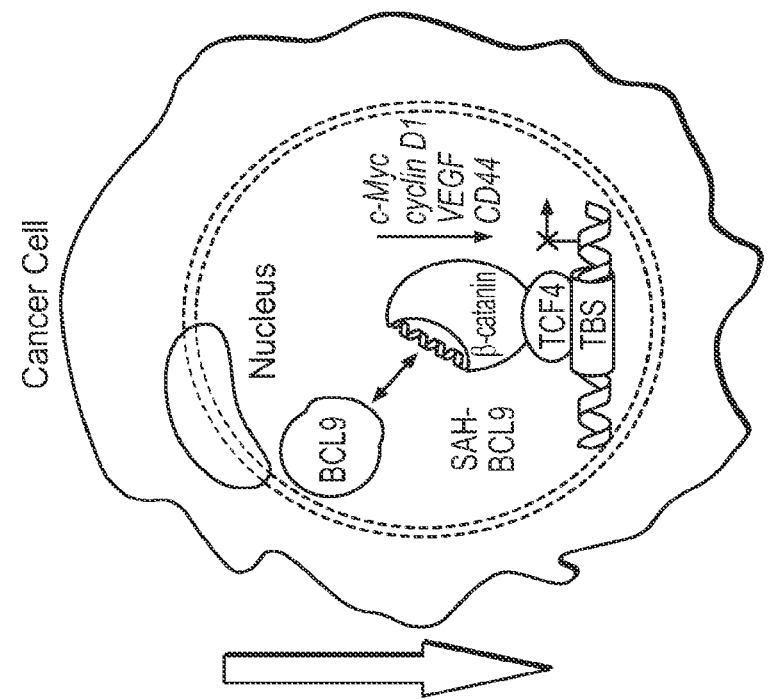
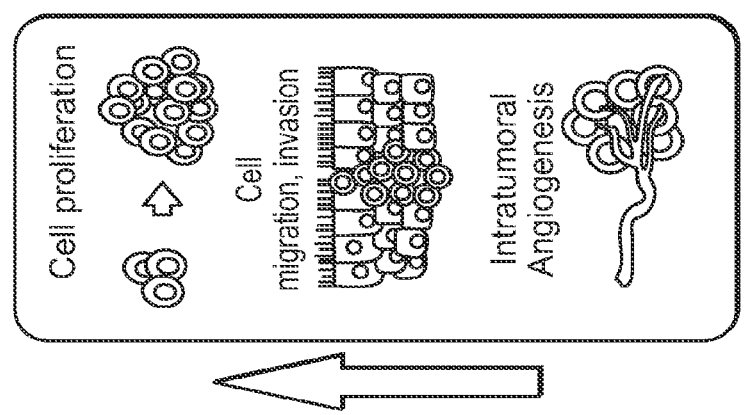
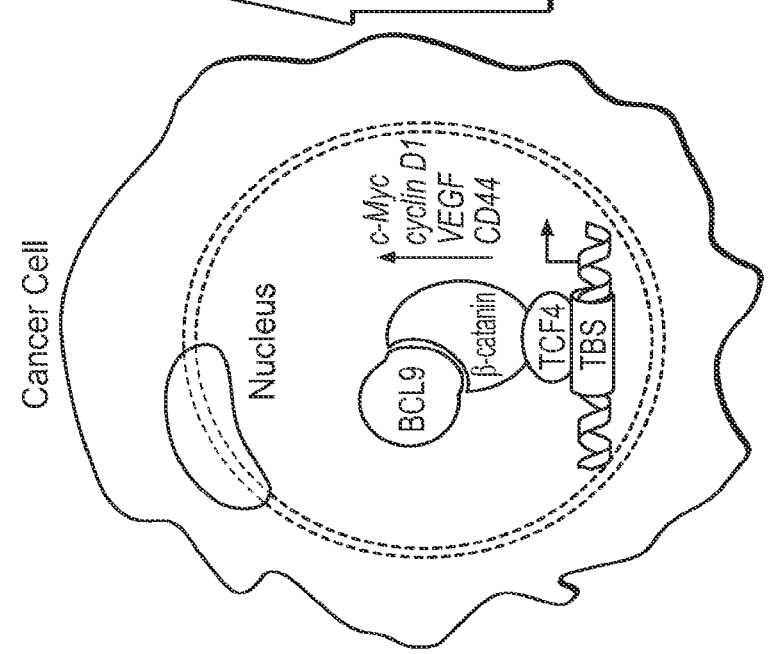
FIG. 5

351 LSQEQLEHRERSLQTLRDIQRBLF 374      BCL9-HD2 domain (SEQ ID NO: 2)
    -SQEQLE--ER-LQ--RD-QR---          non-interacting face
    -----HR--S--TL--I--MLF            interacting face (consensus)
    ("SQEQLE" disclosed as residues 2-6 of SEQ ID NO: 2)

i, i+4 single staples:

XSQEXLEHRERSLQTLRDIQRBLF  (SEQ ID NO: 8)
LXQEXEHRERSLQTLRDIQRBLF   (SEQ ID NO: 9)
LSXEQLXHRERSLQTLRDIQRBLF  (SEQ ID NO: 10)
LSQXQLEXRERSLQTLRDIQRBLF  (SEQ ID NO: 11)
LSQEXLEHXERSLQTLRDIQRBLF  (SEQ ID NO: 12)
LSQEQXEHRXRSLQTLRDIQRBLF  (SEQ ID NO: 13)
LSQEQLXHREXSLQTLRDIQRBLF  (SEQ ID NO: 14)
LSQEQLEXRERXLQTLRDIQRBLF  (SEQ ID NO: 15)
LSQEQLEHXERSXQTLRDIQRBLF  (SEQ ID NO: 16)
LSQEQLEHRXRSLXTLRDIQRBLF  (SEQ ID NO: 17)
LSQEQLEHRERSXQTLXDIQRBLF  (SEQ ID NO: 18)
LSQEQLEHRERXLQTXRDIQRBLF  (SEQ ID NO: 19)
LSQEQLEHRERSXQTLXDIQRBLF  (SEQ ID NO: 20)
LSQEQLEHRERSLXTLRXIQRBLF  (SEQ ID NO: 21)
LSQEQLEHRERSLQXLRDXQRBLF  (SEQ ID NO: 22)
LSQEQLEHRERSLQTLXRDIXRBLF (SEQ ID NO: 23)
LSQEQLEHRERSLQTLRXDIQXBLF (SEQ ID NO: 24)
LSQEQLEHRERSLQTLRXIQRXLF  (SEQ ID NO: 25)
LSQEQLEHRERSLQTLRDXQRBXF  (SEQ ID NO: 26)
LSQEQLEHRERSLQTLRDIXRBLX  (SEQ ID NO: 27)

FIG. 15A

FIG. 15B i, i+7 staples:

XSQEQLEXRERSLQTLRDIQRBLF (SEQ ID NO: 28)
LXQEQLEHXERSLQTLRDIQRBLF (SEQ ID NO: 29)
LSXEQLEHRXRSLQTLRDIQRBLF (SEQ ID NO: 30)
LSQXQLEHREXSLQTLRDIQRBLF (SEQ ID NO: 31)
LSQEXLEHRERXLQTLRDIQRBLF (SEQ ID NO: 32)
LSQEQXEHRERSXQTLRDIQRBLF (SEQ ID NO: 33)
LSQEQLXHRERSLXTLRDIQRBLF (SEQ ID NO: 34)
LSQEQLEXRERSLQXLRDIQRBLF (SEQ ID NO: 35)
LSQEQLEHXERSLQTXRDIQRBLF (SEQ ID NO: 36)
LSQEQLEHRXRSLQTLXDIQRBLF (SEQ ID NO: 37)
LSQEQLEHREXSLQTLRXIQRBLF (SEQ ID NO: 38)
LSQEQLEHRERXLQTLRDXQRBLF (SEQ ID NO: 39)
LSQEQLEHRERSXQTLRDIXRBLF (SEQ ID NO: 40)
LSQEQLEHRERSLXTLRDIQXBLF (SEQ ID NO: 41)
LSQEQLEHRERSLQXLRDIQRXLF (SEQ ID NO: 42)
LSQEQLEHRERSLQTXRDIQRBXF (SEQ ID NO: 43)
LSQEQLEHRERSLQTLXDIQRBLX (SEQ ID NO: 44)

i, i+3 single staples:

XSQXQLEHRERSLQTLRDIQRBLF (SEQ ID NO: 45)
LXQEXLEHRERSLQTLRDIQRBLF (SEQ ID NO: 46)
LSXEQXEHRERSLQTLRDIQRBLF (SEQ ID NO: 47)
LSQEXLEXRERSLQTLRDIQRBLF (SEQ ID NO: 48)
LSQEQXEHXERSLQTLRDIQRBLF (SEQ ID NO: 49)
LSQEQLXHRXRSLQTLRDIQRBLF (SEQ ID NO: 50)
LSQEQLEXREXSLQTLRDIQRBLF (SEQ ID NO: 51)
LSQEQLEHXERXLQTLRDIQRBLF (SEQ ID NO: 52)
LSQEQLEHRXRSXQTLRDIQRBLF (SEQ ID NO: 53)
LSQEQLEHREXSLXTLRDIQRBLF (SEQ ID NO: 54)
LSQEQLEHRERXLQXLRDIQRBLF (SEQ ID NO: 55)
LSQEQLEHRERSXQTXRDIQRBLF (SEQ ID NO: 56)
LSQEQLEHRERSLXTLXDIQRBLF (SEQ ID NO: 57)
LSQEQLEHRERSLQXLRXIQRBLF (SEQ ID NO: 58)
LSQEQLEHRERSLQTXRDXQRBLF (SEQ ID NO: 59)
LSQEQLEHRERSLQTLXDIXRBLF (SEQ ID NO: 60)
LSQEQLEHRERSLQTLRXIQXBLF (SEQ ID NO: 61)
LSQEQLEHRERSLQTLRDXQRXLF (SEQ ID NO: 62)
LSQEQLEHRERSLQTLRDIXRBXF (SEQ ID NO: 63)
LSQEQLEHRERSLQTLRDIQXBLX (SEQ ID NO: 64)

FIG. 15C

<u>i, i+3 double staples:</u>
XSQXQLEHRERSLQTLRDIQXBLX (SEQ ID NO: 65)
XSQXQLEHRERSLQTLRDIXRBXF (SEQ ID NO: 66)
XSQXQLEHRERSLQTLRDXQRBXF (SEQ ID NO: 67)

<u>i, i+4 double staples:</u>
XSQEXLEHRERSLQTLRDIXRBLX (SEQ ID NO: 68)
XSQEXLEHRERSLQTLRDXQRBXF (SEQ ID NO: 69)
XSQEXLEHRERSLQTLXDIQRXLF (SEQ ID NO: 70)

<u>i, i+7 double staples:</u>
XSQEQLEXRERSLQTLXDIQRBLX (SEQ ID NO: 71)
XSQEQLEXRERSLQTXRDIQRBXF (SEQ ID NO: 72)
XSQEQLEXRERSLQXLRDIQRXLF (SEQ ID NO: 73)

<u>Mixed i, i+4; i, i+3; and i, i+7 double staples:</u>
XSQEXLEHRERSLQTLXDIQRBLX (SEQ ID NO: 74)
XSQEXLEHRERSLQTXRDIQRBXF (SEQ ID NO: 75)
XSQEXLEHRERSLQXLRDIQRXLF (SEQ ID NO: 76)

XSQEXLEHRERSLQTLRDIQXBLX (SEQ ID NO: 77)
XSQEXLEHRERSLQTLRDIXRBXF (SEQ ID NO: 78)
XSQEXLEHRERSLQTLRDXQRXLF (SEQ ID NO: 79)

XSQEQLEXRERSLQTLRDIXRBLX (SEQ ID NO: 80)
XSQEQLEXRERSLQTLRDXQRBXF (SEQ ID NO: 81)
XSQEQLEXRERSLQTLRXIQRXLF (SEQ ID NO: 82)

XSQEQLEXRERSLQTLRDIQXBLX (SEQ ID NO: 83)
XSQEQLEXRERSLQTLRDIXRBXF (SEQ ID NO: 84)
XSQEQLEXRERSLQTLRDXQRXLF (SEQ ID NO: 85)

XSQXQLEHRERSLQTLRDIXRBLX (SEQ ID NO: 86)
XSQXQLEHRERSLQTLRDXQRBXF (SEQ ID NO: 87)
XSQXQLEHRERSLQTLRXIQRXLF (SEQ ID NO: 88)

XSQXQLEHRERSLQTLXDIQRBLX (SEQ ID NO: 89)
XSQXQLEHRERSLQTXRDIQRBXF (SEQ ID NO: 90)
XSQXQLEHRERSLQXLRDIQRXLF (SEQ ID NO: 91)

FIG. 15D

_Sequential i, i+4 staples:_
XSQEXLEHXERSXLQTLRDIQRBLF (SEQ ID NO: 92)
LXQEQXEHRXRSLQTLRDIQRBLF (SEQ ID NO: 93)
LSXEQLXHREXSLQTLRDIQRBLF (SEQ ID NO: 94)
LSQXQLEXRERXLQTLRDIQRBLF (SEQ ID NO: 95)
LSQEXLEHXERSXQTLRDIQRBLF (SEQ ID NO: 96)
LSQEQXEHRXRSLXTLRDIQRBLF (SEQ ID NO: 97)
LSQEQLXHREXSLQXLRDIQRBLF (SEQ ID NO: 98)
LSQEQLEXRERXLQTXRDIQRBLF (SEQ ID NO: 99)
LSQEQLEHXERSXQTLXDIQRBLF (SEQ ID NO: 100)
LSQEQLEHRXRSLXTLRXIQRBLF (SEQ ID NO: 101)
LSQEQLEHREXSLQXLRDXQRBLF (SEQ ID NO: 102)
LSQEQLEHRERXLQTXRDIXRBLF (SEQ ID NO: 103)
LSQEQLEHRERSXQTLXDIQXBLF (SEQ ID NO: 104)
LSQEQLEHRERSLXTLRXIQRXLF (SEQ ID NO: 105)
LSQEQLEHRERSLQXLRDXQRBXF (SEQ ID NO: 106)
LSQEQLEHRERSLQTXRDIXRBLX (SEQ ID NO: 107)

_Sequential i, i+3 staples:_
XSQXQLXHRERSLQTLRDIQRBLF (SEQ ID NO: 108)

_Sequential i, i+7 staples:_
XSQEQLEXRERSLQXLRDIQRBLF (SEQ ID NO: 109)

_Mixed sequential staples:_
XSQXQLEXRERSLQTLRDIQRBLF (SEQ ID NO: 110)

XSQXQLEHREXSLQTLRDIQRBLF (SEQ ID NO: 111)

XSQEXLEXRERSLQTLRDIQRBLF (SEQ ID NO: 112)

XSQEXLEHRERXLQTLRDIQRBLF (SEQ ID NO: 113)

XSQEQLEXREXSLQTLRDIQRBLF (SEQ ID NO: 114)

XSQEQLEXRERXLQTLRDIQRBLF (SEQ ID NO: 115)

FIG. 17A
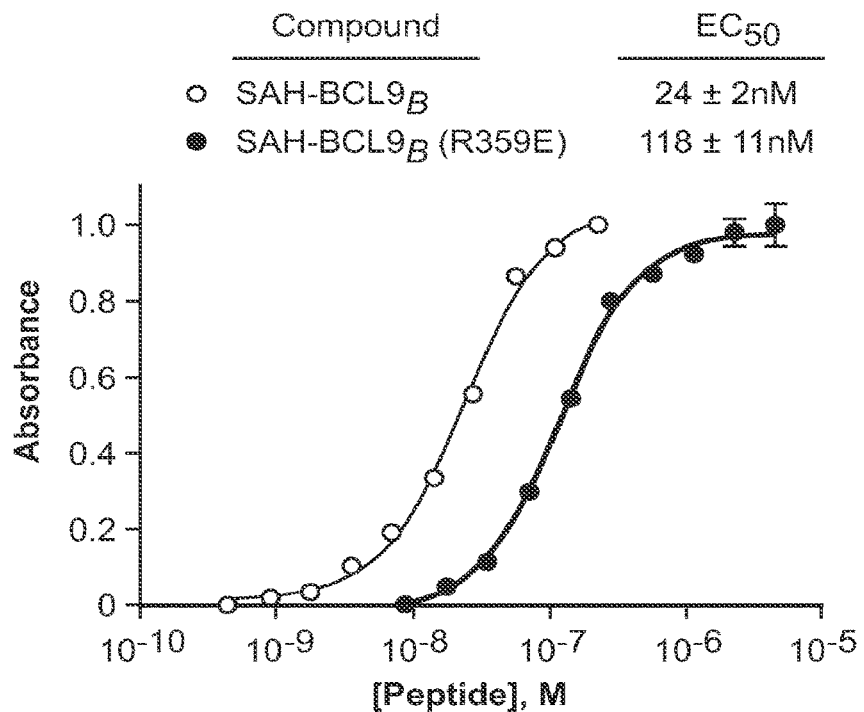
FIG. 17B
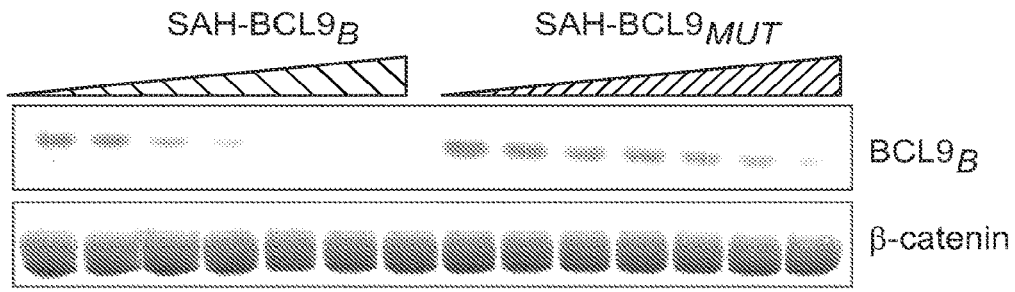
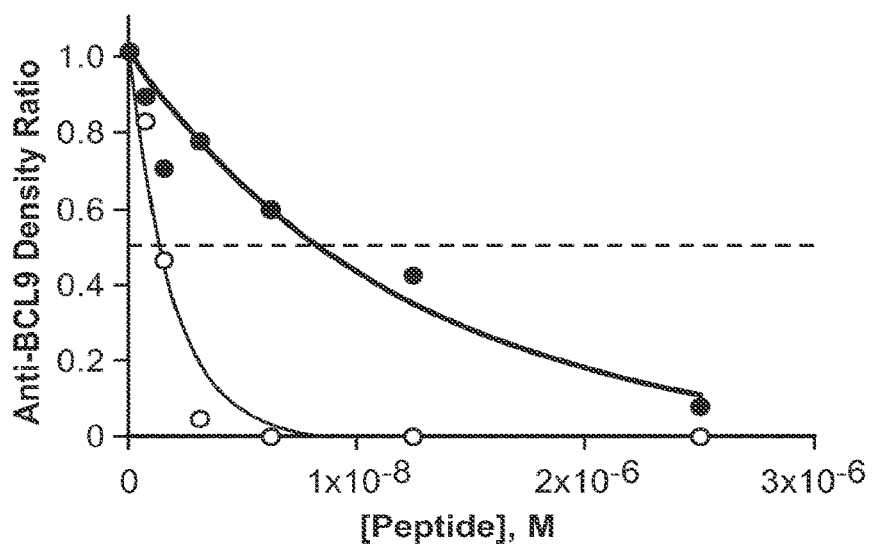

FIG. 18D Adenoma 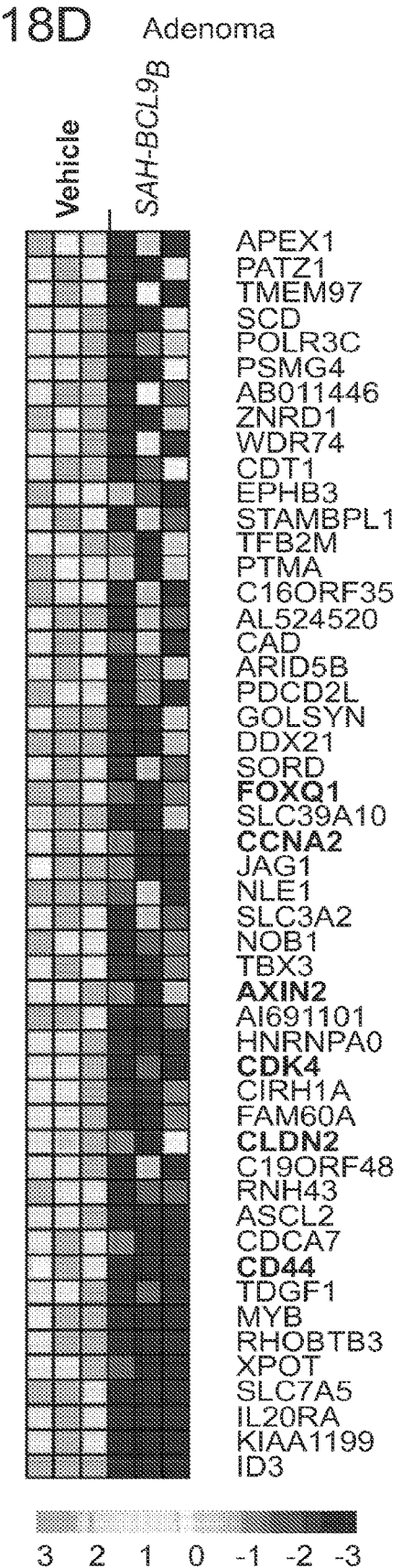 Carcinoma FIG. 18E 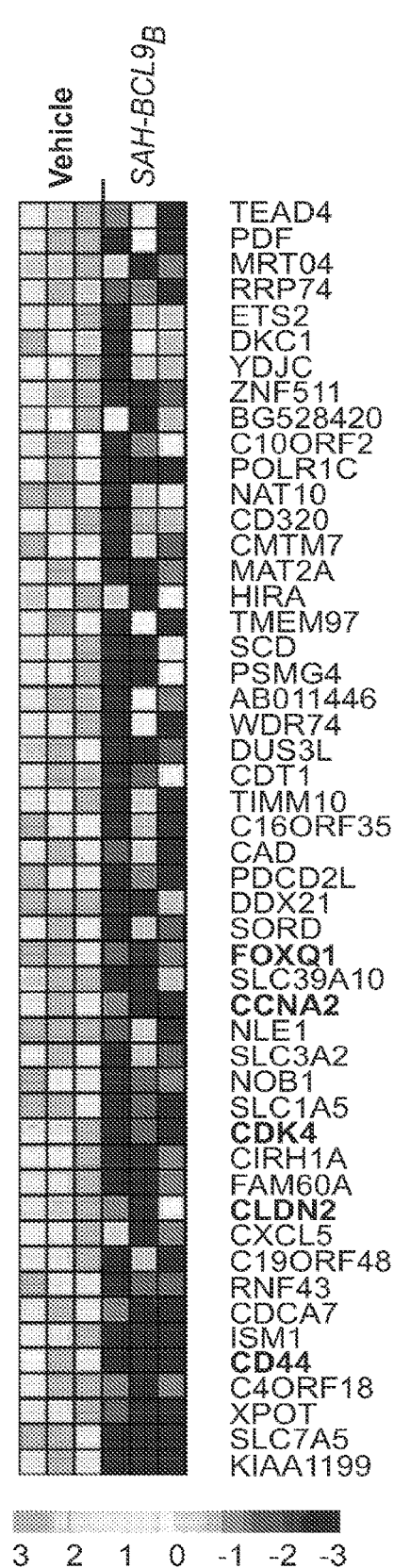

SEQUENCE LISTING

```
<160> NUMBER OF SEQ ID NOS: 141

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Ser Gln Glu Gln Leu Glu His Arg Glu Arg Ser Leu Gln Thr Leu
1               5                   10                  15

Arg Asp Ile Gln Arg Met Leu Phe
            20

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (22)..(22)
<223> OTHER INFORMATION: Xaa at this position is Nle

<400> SEQUENCE: 2

Leu Ser Gln Glu Gln Leu Glu His Arg Glu Arg Ser Leu Gln Thr Leu
1               5                   10                  15

Arg Asp Ile Gln Arg Xaa Leu Phe
            20

<210> SEQ ID NO 3
```

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 3

Leu Ser Gln Glu Gln Leu Glu His Arg Glu Arg Ser Leu Gln Thr Leu
1               5                   10                  15

Arg Xaa Ile Gln Arg Xaa Leu Phe
            20

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 4

Leu Ser Gln Glu Gln Leu Glu His Arg Glu Arg Ser Leu Xaa Thr Leu
1               5                   10                  15

Arg Xaa Ile Gln Arg Xaa Leu Phe
            20

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 5

Leu Ser Gln Glu Gln Leu Glu His Arg Glu Xaa Ser Leu Gln Xaa Leu
1               5                   10                  15

Arg Asp Ile Gln Arg Xaa Leu Phe
```

```
                  20

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 6

Leu Ser Gln Glu Gln Leu Glu Asp Arg Glu Arg Ser Leu Xaa Thr Leu
1               5                   10                  15

Arg Xaa Ile Gln Arg Xaa Leu Phe
            20

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 7

Leu Ser Gln Glu Gln Leu Glu His Glu Glu Arg Ser Leu Xaa Thr Leu
1               5                   10                  15

Arg Xaa Ile Gln Arg Xaa Leu Phe
            20

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (22)..(22)
```

```
<223> OTHER INFORMATION: Xaa at this position is Nle

<400> SEQUENCE: 8

Xaa Ser Gln Glu Xaa Leu Glu His Arg Glu Arg Ser Leu Gln Thr Leu
1               5                   10                  15

Arg Asp Ile Gln Arg Xaa Leu Phe
            20

<210> SEQ ID NO 9
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(2)
<223> OTHER INFORMATION: Xaa may be any amino acid
<220> FEATURE:
<221> NAME/KEY: misc_feature
<222> LOCATION: (6)..(6)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 9

Leu Xaa Gln Glu Gln Xaa Glu His Arg Glu Arg Ser Leu Gln Thr Leu
1               5                   10                  15

Arg Asp Ile Gln Arg Xaa Leu Phe
            20

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(3)
<223> OTHER INFORMATION: Xaa may be any amino acid
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 10

Leu Ser Xaa Glu Gln Leu Xaa His Arg Glu Arg Ser Leu Gln Thr Leu
1               5                   10                  15

Arg Asp Ile Gln Arg Xaa Leu Phe
            20

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(4)
```

```
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 11

Leu Ser Gln Xaa Gln Leu Glu Xaa Arg Glu Arg Ser Leu Gln Thr Leu
1               5                   10                  15

Arg Asp Ile Gln Arg Xaa Leu Phe
            20

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (9)..(9)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 12

Leu Ser Gln Glu Xaa Leu Glu His Xaa Glu Arg Ser Leu Gln Thr Leu
1               5                   10                  15

Arg Asp Ile Gln Arg Xaa Leu Phe
            20

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(6)
<223> OTHER INFORMATION: Xaa may be any amino acid
<220> FEATURE:
<221> NAME/KEY: misc_feature
<222> LOCATION: (10)..(10)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 13

Leu Ser Gln Glu Gln Xaa Glu His Arg Xaa Arg Ser Leu Gln Thr Leu
1               5                   10                  15

Arg Asp Ile Gln Arg Xaa Leu Phe
            20

<210> SEQ ID NO 14
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 14

Leu Ser Gln Glu Gln Leu Xaa His Arg Glu Xaa Ser Leu Gln Thr Leu
1               5                   10                  15

Arg Asp Ile Gln Arg Xaa Leu Phe
            20

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 15

Leu Ser Gln Glu Gln Leu Glu Xaa Arg Glu Arg Xaa Leu Gln Thr Leu
1               5                   10                  15

Arg Asp Ile Gln Arg Xaa Leu Phe
            20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (9)..(9)
<223> OTHER INFORMATION: Xaa may be any amino acid
<220> FEATURE:
<221> NAME/KEY: misc_feature
<222> LOCATION: (13)..(13)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 16

Leu Ser Gln Glu Gln Leu Glu His Xaa Glu Arg Ser Xaa Gln Thr Leu
```

```
              1               5                   10                  15
Arg Asp Ile Gln Arg Xaa Leu Phe
            20

<210> SEQ ID NO 17
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (10)..(10)
<223> OTHER INFORMATION: Xaa may be any amino acid
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 17

Leu Ser Gln Glu Gln Leu Glu His Arg Xaa Arg Ser Leu Xaa Thr Leu
1               5                   10                  15
Arg Asp Ile Gln Arg Xaa Leu Phe
            20

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 18

Leu Ser Gln Glu Gln Leu Glu His Arg Glu Xaa Ser Leu Gln Xaa Leu
1               5                   10                  15
Arg Asp Ile Gln Arg Xaa Leu Phe
            20

<210> SEQ ID NO 19
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (16)..(16)
<223> OTHER INFORMATION: Xaa may be any amino acid
```

```
<220> FEATURE:
<221> NAME/KEY: misc_feature
<222> LOCATION: (22)..(22)
<223> OTHER INFORMATION: Xaa at this position is Nle

<400> SEQUENCE: 19

Leu Ser Gln Glu Gln Leu Glu His Arg Glu Arg Xaa Leu Gln Thr Xaa
1               5                   10                  15

Arg Asp Ile Gln Arg Xaa Leu Phe
            20

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (13)..(13)
<223> OTHER INFORMATION: Xaa may be any amino acid
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 20

Leu Ser Gln Glu Gln Leu Glu His Arg Glu Arg Ser Xaa Gln Thr Leu
1               5                   10                  15

Xaa Asp Ile Gln Arg Xaa Leu Phe
            20

<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 21

Leu Ser Gln Glu Gln Leu Glu His Arg Glu Arg Ser Leu Xaa Thr Leu
1               5                   10                  15

Arg Xaa Ile Gln Arg Xaa Leu Phe
            20

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 22

Leu Ser Gln Glu Gln Leu Glu His Arg Glu Arg Ser Leu Gln Xaa Leu
1               5                   10                  15

Arg Asp Xaa Gln Arg Xaa Leu Phe
            20

<210> SEQ ID NO 23
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 23

Leu Ser Gln Glu Gln Leu Glu His Arg Glu Arg Ser Leu Gln Thr Xaa
1               5                   10                  15

Arg Asp Ile Xaa Arg Xaa Leu Phe
            20

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (21)..(21)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 24

Leu Ser Gln Glu Gln Leu Glu His Arg Glu Arg Ser Leu Gln Thr Leu
1               5                   10                  15

Xaa Asp Ile Gln Xaa Xaa Leu Phe
            20
```

```
<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 25

Leu Ser Gln Glu Gln Leu Glu His Arg Glu Arg Ser Leu Gln Thr Leu
1               5                   10                  15

Arg Xaa Ile Gln Arg Xaa Leu Phe
            20

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 26

Leu Ser Gln Glu Gln Leu Glu His Arg Glu Arg Ser Leu Gln Thr Leu
1               5                   10                  15

Arg Asp Xaa Gln Arg Xaa Xaa Phe
            20

<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 27

Leu Ser Gln Glu Gln Leu Glu His Arg Glu Arg Ser Leu Gln Thr Leu
1               5                   10                  15
```

```
Arg Asp Ile Xaa Arg Xaa Leu Xaa
            20

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 28

Xaa Ser Gln Glu Gln Leu Glu Xaa Arg Glu Arg Ser Leu Gln Thr Leu
1               5                   10                  15

Arg Asp Ile Gln Arg Xaa Leu Phe
            20

<210> SEQ ID NO 29
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(2)
<223> OTHER INFORMATION: Xaa may be any amino acid
<220> FEATURE:
<221> NAME/KEY: misc_feature
<222> LOCATION: (9)..(9)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 29

Leu Xaa Gln Glu Gln Leu Glu His Xaa Glu Arg Ser Leu Gln Thr Leu
1               5                   10                  15

Arg Asp Ile Gln Arg Xaa Leu Phe
            20

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(3)
<223> OTHER INFORMATION: Xaa may be any amino acid
<220> FEATURE:
<221> NAME/KEY: misc_feature
<222> LOCATION: (10)..(10)
<223> OTHER INFORMATION: Xaa may be any amino acid
<220> FEATURE:
```

```
<221> NAME/KEY: misc_feature
<222> LOCATION: (22)..(22)
<223> OTHER INFORMATION: Xaa at this position is Nle

<400> SEQUENCE: 30

Leu Ser Xaa Glu Gln Leu Glu His Arg Xaa Arg Ser Leu Gln Thr Leu
1               5                   10                  15

Arg Asp Ile Gln Arg Xaa Leu Phe
            20

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 31

Leu Ser Gln Xaa Gln Leu Glu His Arg Glu Xaa Ser Leu Gln Thr Leu
1               5                   10                  15

Arg Asp Ile Gln Arg Xaa Leu Phe
            20

<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 32

Leu Ser Gln Glu Xaa Leu Glu His Arg Glu Arg Xaa Leu Gln Thr Leu
1               5                   10                  15

Arg Asp Ile Gln Arg Xaa Leu Phe
            20

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: misc_feature
<222> LOCATION: (6)..(6)
<223> OTHER INFORMATION: Xaa may be any amino acid
<220> FEATURE:
<221> NAME/KEY: misc_feature
<222> LOCATION: (13)..(13)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 33

Leu Ser Gln Glu Gln Xaa Glu His Arg Glu Arg Ser Xaa Gln Thr Leu
1               5                   10                  15

Arg Asp Ile Gln Arg Xaa Leu Phe
            20

<210> SEQ ID NO 34
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 34

Leu Ser Gln Glu Gln Leu Xaa His Arg Glu Arg Ser Leu Xaa Thr Leu
1               5                   10                  15

Arg Asp Ile Gln Arg Xaa Leu Phe
            20

<210> SEQ ID NO 35
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 35

Leu Ser Gln Glu Gln Leu Glu Xaa Arg Glu Arg Ser Leu Gln Xaa Leu
1               5                   10                  15

Arg Asp Ile Gln Arg Xaa Leu Phe
            20
```

```
<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (9)..(9)
<223> OTHER INFORMATION: Xaa may be any amino acid
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 36

Leu Ser Gln Glu Gln Leu Glu His Xaa Glu Arg Ser Leu Gln Thr Xaa
1               5                   10                  15

Arg Asp Ile Gln Arg Xaa Leu Phe
            20

<210> SEQ ID NO 37
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (10)..(10)
<223> OTHER INFORMATION: Xaa may be any amino acid
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 37

Leu Ser Gln Glu Gln Leu Glu His Arg Xaa Arg Ser Leu Gln Thr Leu
1               5                   10                  15

Xaa Asp Ile Gln Arg Xaa Leu Phe
            20

<210> SEQ ID NO 38
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 38
```

```
Leu Ser Gln Glu Gln Leu Glu His Arg Glu Xaa Ser Leu Gln Thr Leu
1               5                   10                  15

Arg Xaa Ile Gln Arg Xaa Leu Phe
            20

<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 39

Leu Ser Gln Glu Gln Leu Glu His Arg Glu Arg Xaa Leu Gln Thr Leu
1               5                   10                  15

Arg Asp Xaa Gln Arg Xaa Leu Phe
            20

<210> SEQ ID NO 40
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (13)..(13)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 40

Leu Ser Gln Glu Gln Leu Glu His Arg Glu Arg Ser Xaa Gln Thr Leu
1               5                   10                  15

Arg Asp Ile Xaa Arg Xaa Leu Phe
            20

<210> SEQ ID NO 41
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
```

```
<222> LOCATION: (21)..(21)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 41

Leu Ser Gln Glu Gln Leu Glu His Arg Glu Arg Ser Leu Xaa Thr Leu
1               5                   10                  15

Arg Asp Ile Gln Xaa Xaa Leu Phe
            20

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 42

Leu Ser Gln Glu Gln Leu Glu His Arg Glu Arg Ser Leu Gln Xaa Leu
1               5                   10                  15

Arg Asp Ile Gln Arg Xaa Leu Phe
            20

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 43

Leu Ser Gln Glu Gln Leu Glu His Arg Glu Arg Ser Leu Gln Thr Xaa
1               5                   10                  15

Arg Asp Ile Gln Arg Xaa Xaa Phe
            20

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
```

```
<222> LOCATION: (17)..(17)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 44

Leu Ser Gln Glu Gln Leu Glu His Arg Glu Arg Ser Leu Gln Thr Leu
1               5                   10                  15

Xaa Asp Ile Gln Arg Xaa Leu Xaa
            20

<210> SEQ ID NO 45
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 45

Xaa Ser Gln Xaa Gln Leu Glu His Arg Glu Arg Ser Leu Gln Thr Leu
1               5                   10                  15

Arg Asp Ile Gln Arg Xaa Leu Phe
            20

<210> SEQ ID NO 46
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(2)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 46

Leu Xaa Gln Glu Xaa Leu Glu His Arg Glu Arg Ser Leu Gln Thr Leu
1               5                   10                  15

Arg Asp Ile Gln Arg Xaa Leu Phe
            20

<210> SEQ ID NO 47
```

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(3)
<223> OTHER INFORMATION: Xaa may be any amino acid
<220> FEATURE:
<221> NAME/KEY: misc_feature
<222> LOCATION: (6)..(6)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 47

Leu Ser Xaa Glu Gln Xaa Glu His Arg Glu Arg Ser Leu Gln Thr Leu
1               5                   10                  15

Arg Asp Ile Gln Arg Xaa Leu Phe
            20

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 48

Leu Ser Gln Glu Xaa Leu Glu Xaa Arg Glu Arg Ser Leu Gln Thr Leu
1               5                   10                  15

Arg Asp Ile Gln Arg Xaa Leu Phe
            20

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(6)
<223> OTHER INFORMATION: Xaa may be any amino acid
<220> FEATURE:
<221> NAME/KEY: misc_feature
<222> LOCATION: (9)..(9)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 49
```

Leu Ser Gln Glu Gln Xaa Glu His Xaa Glu Arg Ser Leu Gln Thr Leu
1               5                   10                  15

Arg Asp Ile Gln Arg Xaa Leu Phe
            20

<210> SEQ ID NO 50
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (10)..(10)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 50

Leu Ser Gln Glu Gln Leu Xaa His Arg Xaa Arg Ser Leu Gln Thr Leu
1               5                   10                  15

Arg Asp Ile Gln Arg Xaa Leu Phe
            20

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 51

Leu Ser Gln Glu Gln Leu Glu Xaa Arg Glu Xaa Ser Leu Gln Thr Leu
1               5                   10                  15

Arg Asp Ile Gln Arg Xaa Leu Phe
            20

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (9)..(9)
<223> OTHER INFORMATION: Xaa may be any amino acid
<220> FEATURE:
<221> NAME/KEY: misc_feature
<222> LOCATION: (12)..(12)

```
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 52

Leu Ser Gln Glu Gln Leu Glu His Xaa Glu Arg Xaa Leu Gln Thr Leu
1               5                   10                  15

Arg Asp Ile Gln Arg Xaa Leu Phe
            20

<210> SEQ ID NO 53
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (10)..(10)
<223> OTHER INFORMATION: Xaa may be any amino acid
<220> FEATURE:
<221> NAME/KEY: misc_feature
<222> LOCATION: (13)..(13)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 53

Leu Ser Gln Glu Gln Leu Glu His Arg Xaa Arg Ser Xaa Gln Thr Leu
1               5                   10                  15

Arg Asp Ile Gln Arg Xaa Leu Phe
            20

<210> SEQ ID NO 54
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 54

Leu Ser Gln Glu Gln Leu Glu His Arg Glu Xaa Ser Leu Xaa Thr Leu
1               5                   10                  15

Arg Asp Ile Gln Arg Xaa Leu Phe
            20

<210> SEQ ID NO 55
<211> LENGTH: 24
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 55

Leu Ser Gln Glu Gln Leu Glu His Arg Glu Arg Xaa Leu Gln Xaa Leu
1               5                   10                  15

Arg Asp Ile Gln Arg Xaa Leu Phe
            20

<210> SEQ ID NO 56
<211> LENGTH: 24
<212> TYPE: PRT
<213> ORGANISM: Artificial Sequence
<220> FEATURE:
<223> OTHER INFORMATION: Description of Artificial Sequence: Synthetic
            peptide
<220> FEATURE:
<221> NAME/KEY: misc_feature
<222> LOCATION: (13)..(13)
<223> OTHER INFORMATION: Xaa may be any amino acid
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 56

Leu Ser Gln Glu Gln Leu Glu His Arg Glu Arg Ser Xaa Gln Thr Xaa
1               5                   10                  15

Arg Asp Ile Gln Arg Xaa Leu Phe
            20

<210> SEQ ID NO 57
<211> LENGTH: 24
<212> TYPE: PRT
<213> ORGANISM: Artificial Sequence
<220> FEATURE:
<223> OTHER INFORMATION: Description of Artificial Sequence: Synthetic
            peptide
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 57

Leu Ser Gln Glu Gln Leu Glu His Arg Glu Arg Ser Leu Xaa Thr Leu
1               5                   10                  15

Xaa Asp Ile Gln Arg Xaa Leu Phe
            20
```

```
<210> SEQ ID NO 58
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 58

Leu Ser Gln Glu Gln Leu Glu His Arg Glu Arg Ser Leu Gln Xaa Leu
1               5                   10                  15

Arg Xaa Ile Gln Arg Xaa Leu Phe
            20

<210> SEQ ID NO 59
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 59

Leu Ser Gln Glu Gln Leu Glu His Arg Glu Arg Ser Leu Gln Thr Xaa
1               5                   10                  15

Arg Asp Xaa Gln Arg Xaa Leu Phe
            20

<210> SEQ ID NO 60
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
```

<400> SEQUENCE: 60

Leu Ser Gln Glu Gln Leu Glu His Arg Glu Arg Ser Leu Gln Thr Leu
1               5                   10                  15

Xaa Asp Ile Xaa Arg Xaa Leu Phe
            20

<210> SEQ ID NO 61
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (21)..(21)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 61

Leu Ser Gln Glu Gln Leu Glu His Arg Glu Arg Ser Leu Gln Thr Leu
1               5                   10                  15

Arg Xaa Ile Gln Xaa Xaa Leu Phe
            20

<210> SEQ ID NO 62
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 62

Leu Ser Gln Glu Gln Leu Glu His Arg Glu Arg Ser Leu Gln Thr Leu
1               5                   10                  15

Arg Asp Xaa Gln Arg Xaa Leu Phe
            20

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

```
<220> FEATURE:
<221> NAME/KEY: misc_feature
<222> LOCATION: (23)..(23)
<223> OTHER INFORMATION: Xaa may be any amino acid

<400> SEQUENCE: 63

Leu Ser Gln Glu Gln Leu Glu His Arg Glu Arg Ser Leu Gln Thr Leu
1               5                   10                  15

Arg Asp Ile Xaa Arg Xaa Xaa Phe
            20

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (21)..(21)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 64

Leu Ser Gln Glu Gln Leu Glu His Arg Glu Arg Ser Leu Gln Thr Leu
1               5                   10                  15

Arg Asp Ile Gln Xaa Xaa Leu Xaa
            20

<210> SEQ ID NO 65
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (21)..(21)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 65

Xaa Ser Gln Xaa Gln Leu Glu His Arg Glu Arg Ser Leu Gln Thr Leu
1               5                   10                  15

Arg Asp Ile Gln Xaa Xaa Leu Xaa
            20
```

```
<210> SEQ ID NO 66
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 66

Xaa Ser Gln Xaa Gln Leu Glu His Arg Glu Arg Ser Leu Gln Thr Leu
1               5                   10                  15

Arg Asp Ile Xaa Arg Xaa Xaa Phe
            20

<210> SEQ ID NO 67
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 67

Xaa Ser Gln Xaa Gln Leu Glu His Arg Glu Arg Ser Leu Gln Thr Leu
1               5                   10                  15

Arg Asp Xaa Gln Arg Xaa Xaa Phe
            20

<210> SEQ ID NO 68
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 68

Xaa Ser Gln Glu Xaa Leu Glu His Arg Glu Arg Ser Leu Gln Thr Leu
1               5                   10                  15

Arg Asp Ile Xaa Arg Xaa Leu Xaa
            20

<210> SEQ ID NO 69
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 69

Xaa Ser Gln Glu Xaa Leu Glu His Arg Glu Arg Ser Leu Gln Thr Leu
1               5                   10                  15

Arg Asp Xaa Gln Arg Xaa Xaa Phe
            20

<210> SEQ ID NO 70
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
```

```
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 70

Xaa Ser Gln Glu Xaa Leu Glu His Arg Glu Arg Ser Leu Gln Thr Leu
1               5                   10                  15

Xaa Asp Ile Gln Arg Xaa Leu Phe
            20

<210> SEQ ID NO 71
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 71

Xaa Ser Gln Glu Gln Leu Glu Xaa Arg Glu Arg Ser Leu Gln Thr Leu
1               5                   10                  15

Xaa Asp Ile Gln Arg Xaa Leu Xaa
            20

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (16)..(16)
```

```
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 72

Xaa Ser Gln Glu Gln Leu Glu Xaa Arg Glu Arg Ser Leu Gln Thr Xaa
1               5                   10                  15

Arg Asp Ile Gln Arg Xaa Xaa Phe
            20

<210> SEQ ID NO 73
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 73

Xaa Ser Gln Glu Gln Leu Glu Xaa Arg Glu Arg Ser Leu Gln Xaa Leu
1               5                   10                  15

Arg Asp Ile Gln Arg Xaa Leu Phe
            20

<210> SEQ ID NO 74
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid
```

```
<400> SEQUENCE: 74

Xaa Ser Gln Glu Xaa Leu Glu His Arg Glu Arg Ser Leu Gln Thr Leu
1               5                   10                  15

Xaa Asp Ile Gln Arg Xaa Leu Xaa
            20

<210> SEQ ID NO 75
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 75

Xaa Ser Gln Glu Xaa Leu Glu His Arg Glu Arg Ser Leu Gln Thr Xaa
1               5                   10                  15

Arg Asp Ile Gln Arg Xaa Xaa Phe
            20

<210> SEQ ID NO 76
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 76

Xaa Ser Gln Glu Xaa Leu Glu His Arg Glu Arg Ser Leu Gln Xaa Leu
1               5                   10                  15

Arg Asp Ile Gln Arg Xaa Leu Phe
            20
```

```
<210> SEQ ID NO 77
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (21)..(21)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 77

Xaa Ser Gln Glu Xaa Leu Glu His Arg Glu Arg Ser Leu Gln Thr Leu
1               5                   10                  15

Arg Asp Ile Gln Xaa Xaa Leu Xaa
            20

<210> SEQ ID NO 78
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 78

Xaa Ser Gln Glu Xaa Leu Glu His Arg Glu Arg Ser Leu Gln Thr Leu
1               5                   10                  15

Arg Asp Ile Xaa Arg Xaa Xaa Phe
            20

<210> SEQ ID NO 79
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 79

Xaa Ser Gln Glu Xaa Leu Glu His Arg Glu Arg Ser Leu Gln Thr Leu
1               5                   10                  15

Arg Asp Xaa Gln Arg Xaa Leu Phe
            20

<210> SEQ ID NO 80
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 80

Xaa Ser Gln Glu Gln Leu Glu Xaa Arg Glu Arg Ser Leu Gln Thr Leu
1               5                   10                  15

Arg Asp Ile Xaa Arg Xaa Leu Xaa
            20

<210> SEQ ID NO 81
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
```

```
<222> LOCATION: (8)..(8)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 81

Xaa Ser Gln Glu Gln Leu Glu Xaa Arg Glu Arg Ser Leu Gln Thr Leu
1               5                   10                  15

Arg Asp Xaa Gln Arg Xaa Xaa Phe
            20

<210> SEQ ID NO 82
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 82

Xaa Ser Gln Glu Gln Leu Glu Xaa Arg Glu Arg Ser Leu Gln Thr Leu
1               5                   10                  15

Arg Xaa Ile Gln Arg Xaa Leu Phe
            20

<210> SEQ ID NO 83
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (21)..(21)
<223> OTHER INFORMATION: Xaa may be any amino acid
<220> FEATURE:
<221> NAME/KEY: misc_feature
<222> LOCATION: (22)..(22)
```

```
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 83

Xaa Ser Gln Glu Gln Leu Glu Xaa Arg Glu Arg Ser Leu Gln Thr Leu
1               5                   10                  15

Arg Asp Ile Gln Xaa Xaa Leu Xaa
            20

<210> SEQ ID NO 84
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 84

Xaa Ser Gln Glu Gln Leu Glu Xaa Arg Glu Arg Ser Leu Gln Thr Leu
1               5                   10                  15

Arg Asp Ile Xaa Arg Xaa Xaa Phe
            20

<210> SEQ ID NO 85
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 85

Xaa Ser Gln Glu Gln Leu Glu Xaa Arg Glu Arg Ser Leu Gln Thr Leu
```

```
1               5                   10                  15
Arg Asp Xaa Gln Arg Xaa Leu Phe
            20

<210> SEQ ID NO 86
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 86

Xaa Ser Gln Xaa Gln Leu Glu His Arg Glu Arg Ser Leu Gln Thr Leu
1               5                   10                  15

Arg Asp Ile Xaa Arg Xaa Leu Xaa
            20

<210> SEQ ID NO 87
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 87

Xaa Ser Gln Xaa Gln Leu Glu His Arg Glu Arg Ser Leu Gln Thr Leu
1               5                   10                  15

Arg Asp Xaa Gln Arg Xaa Xaa Phe
            20
```

```
<210> SEQ ID NO 88
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 88

Xaa Ser Gln Xaa Gln Leu Glu His Arg Glu Arg Ser Leu Gln Thr Leu
1               5                   10                  15

Arg Xaa Ile Gln Arg Xaa Leu Phe
            20

<210> SEQ ID NO 89
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 89

Xaa Ser Gln Xaa Gln Leu Glu His Arg Glu Arg Ser Leu Gln Thr Leu
1               5                   10                  15

Xaa Asp Ile Gln Arg Xaa Leu Xaa
            20

<210> SEQ ID NO 90
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 90

Xaa Ser Gln Xaa Gln Leu Glu His Arg Glu Arg Ser Leu Gln Thr Xaa
1               5                   10                  15

Arg Asp Ile Gln Arg Xaa Xaa Phe
            20

<210> SEQ ID NO 91
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 91

Xaa Ser Gln Xaa Gln Leu Glu His Arg Glu Arg Ser Leu Gln Xaa Leu
1               5                   10                  15

Arg Asp Ile Gln Arg Xaa Leu Phe
            20

<210> SEQ ID NO 92
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
```

```
<222> LOCATION: (9)..(9)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 92

Xaa Ser Gln Glu Xaa Leu Glu His Xaa Glu Arg Ser Leu Gln Thr Leu
1               5                   10                  15

Arg Asp Ile Gln Arg Xaa Leu Phe
            20

<210> SEQ ID NO 93
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(2)
<223> OTHER INFORMATION: Xaa may be any amino acid
<220> FEATURE:
<221> NAME/KEY: misc_feature
<222> LOCATION: (6)..(6)
<223> OTHER INFORMATION: Xaa may be any amino acid
<220> FEATURE:
<221> NAME/KEY: misc_feature
<222> LOCATION: (10)..(10)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 93

Leu Xaa Gln Glu Gln Xaa Glu His Arg Xaa Arg Ser Leu Gln Thr Leu
1               5                   10                  15

Arg Asp Ile Gln Arg Xaa Leu Phe
            20

<210> SEQ ID NO 94
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(3)
<223> OTHER INFORMATION: Xaa may be any amino acid
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 94

Leu Ser Xaa Glu Gln Leu Xaa His Arg Glu Xaa Ser Leu Gln Thr Leu
1               5                   10                  15

Arg Asp Ile Gln Arg Xaa Leu Phe
```

20

<210> SEQ ID NO 95
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 95

Leu Ser Gln Xaa Gln Leu Glu Xaa Arg Glu Arg Xaa Leu Gln Thr Leu
1               5                   10                  15

Arg Asp Ile Gln Arg Xaa Leu Phe
            20

<210> SEQ ID NO 96
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (9)..(9)
<223> OTHER INFORMATION: Xaa may be any amino acid
<220> FEATURE:
<221> NAME/KEY: misc_feature
<222> LOCATION: (13)..(13)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 96

Leu Ser Gln Glu Xaa Leu Glu His Xaa Glu Arg Ser Xaa Gln Thr Leu
1               5                   10                  15

Arg Asp Ile Gln Arg Xaa Leu Phe
            20

<210> SEQ ID NO 97
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(6)

```
<223> OTHER INFORMATION: Xaa may be any amino acid
<220> FEATURE:
<221> NAME/KEY: misc_feature
<222> LOCATION: (10)..(10)
<223> OTHER INFORMATION: Xaa may be any amino acid
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 97

Leu Ser Gln Glu Gln Xaa Glu His Arg Xaa Arg Ser Leu Xaa Thr Leu
1               5                   10                  15

Arg Asp Ile Gln Arg Xaa Leu Phe
            20

<210> SEQ ID NO 98
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 98

Leu Ser Gln Glu Gln Leu Xaa His Arg Glu Xaa Ser Leu Gln Xaa Leu
1               5                   10                  15

Arg Asp Ile Gln Arg Xaa Leu Phe
            20

<210> SEQ ID NO 99
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
```

<400> SEQUENCE: 99

Leu Ser Gln Glu Gln Leu Glu Xaa Arg Glu Arg Xaa Leu Gln Thr Xaa
1               5                   10                  15

Arg Asp Ile Gln Arg Xaa Leu Phe
            20

<210> SEQ ID NO 100
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (9)..(9)
<223> OTHER INFORMATION: Xaa may be any amino acid
<220> FEATURE:
<221> NAME/KEY: misc_feature
<222> LOCATION: (13)..(13)
<223> OTHER INFORMATION: Xaa may be any amino acid
<220> FEATURE:
<221> NAME/KEY: misc_feature
<222> LOCATION: (17)..(17)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 100

Leu Ser Gln Glu Gln Leu Glu His Xaa Glu Arg Ser Xaa Gln Thr Leu
1               5                   10                  15

Xaa Asp Ile Gln Arg Xaa Leu Phe
            20

<210> SEQ ID NO 101
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (10)..(10)
<223> OTHER INFORMATION: Xaa may be any amino acid
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 101

Leu Ser Gln Glu Gln Leu Glu His Arg Xaa Arg Ser Leu Xaa Thr Leu
1               5                   10                  15

Arg Xaa Ile Gln Arg Xaa Leu Phe
            20

<210> SEQ ID NO 102
<211> LENGTH: 24
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 102

Leu Ser Gln Glu Gln Leu Glu His Arg Glu Xaa Ser Leu Gln Xaa Leu
1               5                   10                  15
Arg Asp Xaa Gln Arg Xaa Leu Phe
            20

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 103

Leu Ser Gln Glu Gln Leu Glu His Arg Glu Arg Xaa Leu Gln Thr Xaa
1               5                   10                  15
Arg Asp Ile Xaa Arg Xaa Leu Phe
            20

<210> SEQ ID NO 104
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (13)..(13)
<223> OTHER INFORMATION: Xaa may be any amino acid
<220> FEATURE:
<221> NAME/KEY: misc_feature
<222> LOCATION: (17)..(17)
<223> OTHER INFORMATION: Xaa may be any amino acid
<220> FEATURE:

```
<221> NAME/KEY: misc_feature
<222> LOCATION: (21)..(21)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 104

Leu Ser Gln Glu Gln Leu Glu His Arg Glu Arg Ser Xaa Gln Thr Leu
1               5                   10                  15

Xaa Asp Ile Gln Xaa Xaa Leu Phe
            20

<210> SEQ ID NO 105
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa may be any amino acid

<400> SEQUENCE: 105

Leu Ser Gln Glu Gln Leu Glu His Arg Glu Arg Ser Leu Xaa Thr Leu
1               5                   10                  15

Arg Xaa Ile Gln Arg Xaa Leu Phe
            20

<210> SEQ ID NO 106
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (19)..(19)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (23)..(23)
<223> OTHER INFORMATION: Xaa may be any amino acid

<400> SEQUENCE: 106

Leu Ser Gln Glu Gln Leu Glu His Arg Glu Arg Ser Leu Gln Xaa Leu
1               5                   10                  15

Arg Asp Xaa Gln Arg Xaa Xaa Phe
            20
```

```
<210> SEQ ID NO 107
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (16)..(16)
<223> OTHER INFORMATION: Xaa may be any amino acid
<220> FEATURE:
<221> NAME/KEY: misc_feature
<222> LOCATION: (20)..(20)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle
<220> FEATURE:
<221> NAME/KEY: misc_feature
<222> LOCATION: (24)..(24)
<223> OTHER INFORMATION: Xaa may be any amino acid

<400> SEQUENCE: 107

Leu Ser Gln Glu Gln Leu Glu His Arg Glu Arg Ser Leu Gln Thr Xaa
1               5                   10                  15

Arg Asp Ile Xaa Arg Xaa Leu Xaa
            20

<210> SEQ ID NO 108
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 108

Xaa Ser Gln Xaa Gln Leu Xaa His Arg Glu Arg Ser Leu Gln Thr Leu
1               5                   10                  15

Arg Asp Ile Gln Arg Xaa Leu Phe
            20

<210> SEQ ID NO 109
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
```

```
<222> LOCATION: (8)..(8)
<223> OTHER INFORMATION: Xaa may be any amino acid
<220> FEATURE:
<221> NAME/KEY: misc_feature
<222> LOCATION: (15)..(15)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 109

Xaa Ser Gln Glu Gln Leu Glu Xaa Arg Glu Arg Ser Leu Gln Xaa Leu
1               5                   10                  15

Arg Asp Ile Gln Arg Xaa Leu Phe
            20

<210> SEQ ID NO 110
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 110

Xaa Ser Gln Xaa Gln Leu Glu Xaa Arg Glu Arg Ser Leu Gln Thr Leu
1               5                   10                  15

Arg Asp Ile Gln Arg Xaa Leu Phe
            20

<210> SEQ ID NO 111
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (4)..(4)
<223> OTHER INFORMATION: Xaa may be any amino acid
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 111
```

Xaa Ser Gln Xaa Gln Leu Glu His Arg Glu Xaa Ser Leu Gln Thr Leu
1               5                   10                  15

Arg Asp Ile Gln Arg Xaa Leu Phe
            20

<210> SEQ ID NO 112
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 112

Xaa Ser Gln Glu Xaa Leu Glu Xaa Arg Glu Arg Ser Leu Gln Thr Leu
1               5                   10                  15

Arg Asp Ile Gln Arg Xaa Leu Phe
            20

<210> SEQ ID NO 113
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 113

Xaa Ser Gln Glu Xaa Leu Glu His Arg Glu Arg Xaa Leu Gln Thr Leu
1               5                   10                  15

Arg Asp Ile Gln Arg Xaa Leu Phe
            20

<210> SEQ ID NO 114
<211> LENGTH: 24
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (11)..(11)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 114

Xaa Ser Gln Glu Gln Leu Glu Xaa Arg Glu Xaa Ser Leu Gln Thr Leu
1               5                   10                  15

Arg Asp Ile Gln Arg Xaa Leu Phe
            20

<210> SEQ ID NO 115
<211> LENGTH: 24
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
<222> LOCATION: (8)..(8)
<223> OTHER INFORMATION: Xaa may be any amino acid
<220> FEATURE:
<221> NAME/KEY: misc_feature
<222> LOCATION: (12)..(12)
<223> OTHER INFORMATION: Xaa may be any amino acid
<220> FEATURE:
<221> NAME/KEY: misc_feature
<222> LOCATION: (22)..(22)
<223> OTHER INFORMATION: Xaa at this position is Nle

<400> SEQUENCE: 115

Xaa Ser Gln Glu Gln Leu Glu Xaa Arg Glu Arg Xaa Leu Gln Thr Leu
1               5                   10                  15

Arg Asp Ile Gln Arg Xaa Leu Phe
            20

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
        primer

<400> SEQUENCE: 116
gcgtgtctct ggacagagtt t                                           21

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 117
agcctcagcc cttccaca                                                 18

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gaggctatgc cagctgtagg                                               20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cccttttcct ccaactctcc                                               20

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
actcccccgg ctcggtccac aagc                                          24

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
cccaatttct cagccaggtt tcag                                          24

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cgcggacttt gcactttgaa                                               20

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 123
agctttaagg cacgtttgat ggag                                          24

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
atgttgtccg gctgatgga                                                19

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
caccagggtt accttgatct cc                                            22

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cggaaactgt tgacagtgga t                                             21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ggtgcaaaga catagccaga a                                             21

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
catgaacttt ctgctgtctt gg                                            22

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 129
atgattctgc cctcctcctt                                           20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ctcccaggtc tggtgtgttg                                           20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gtgaagacgc tgaggttgga                                           20

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tttttcgggt agtggaaaac c                                         21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gcagtagaaa tacggctgca c                                         21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tttgcattgc agtcaacagt c                                         21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgagtccact tggctttctg t                                           21

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
cggtgtggct aagtacaggc                                             20

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
caaagctcac gatggtggtc t                                           21

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
catcccttcc tcattccttc aac                                         23

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
aggcttccta aaaggtggtg g                                           21

<210> SEQ ID NO 140
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (14)..(14)
<223> OTHER INFORMATION: Xaa may be any amino acid
<220> FEATURE:
<221> NAME/KEY: misc_feature
<222> LOCATION: (18)..(18)
<223> OTHER INFORMATION: Xaa may be any amino acid

<400> SEQUENCE: 140

Leu Ser Gln Glu Gln Leu Glu His Arg Glu Arg Ser Leu Xaa Thr Leu
1               5                   10                  15

Arg Xaa Ile Gln Arg Met Leu Phe
            20

```
<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 141

His His His His His His
1               5
```

TARGETING DEREGULATED WNT SIGNALING IN CANCER USING STABILIZED ALPHA-HELICES OF BCL-9

This application is a divisional application of U.S. application Ser. No. 14/111,299, filed Dec. 6, 2013, now U.S. Pat. No. 10,703,785, which is a national stage application filed under 35 U.S.C. § 371 of International Application No. PCT/US2012/033822, filed Apr. 16, 2012, which claims the benefit of priority under 35 U.S.C. § 119(e) to U.S. Provisional Application No. 61/475,932, filed Apr. 15, 2011, each of which is incorporated herein by reference in its entirety.

STATEMENT OF RIGHTS TO INVENTIONS MADE UNDER FEDERALLY SPONSORED RESEARCH

This invention was made with government support under grant number R01 CA151391 awarded by The National Institutes of Health. The government has certain rights in the invention.

SEQUENCE LISTING

The instant application contains a Sequence Listing which has been submitted electronically in ASCHII format and is hereby incorporated by reference in its entirety. Said ASCII copy, created on Dec. 31, 2015 is named 48289-521N01US_SL.txt and is 80,031 bytes in size.

BACKGROUND

The canonical Wnt pathway regulates the constitutive level and intracellular localization of β-catenin, a key component of a tightly regulated receptor-mediated signal transduction network required for both embryonic development and adult tissue homeostasis. In unstimulated normal cells, β-catenin binds to adenomatous polyposis coli (APC), glycogen synthase kinase 3β (GSK3β), and Axin, which form a destruction complex that phosphorylates β-catenin, targeting it for proteosomal degradation. The binding of Wnt ligands to the frizzled and low-density lipoprotein receptors (LRP5 and LRP6) inhibits the activity of the GSK3β/APC/Axin complex, enabling non-phosphorylated β-catenin to undergo nuclear translocation to exert its transcriptional effects. Nuclear β-catenin associates with the lymphoid enhancer factor/T-cell factor (LEF/TCF) family of transcription factors to induce the expression of cell proliferation, migration, and survival genes, such as c-Myc and cyclin D1. Normally, this transcriptional pathway is turned off when Wnt ligands uncouple from their receptors. However, a variety of loss of function mutations in APC and Axin, and activating mutations in β-catenin itself, enable β-catenin to escape the destruction complex, persist in the nucleus, and drive oncogenic transcription.

In *Drosophila melanogaster*, the transcriptional activity of β-catenin further depends on two co-factors, BCL9 and Pygopus. The formation of a quaternary complex consisting of TCF, β-catenin, BCL9, and Pygopus enhances β-catenin-dependent Wnt transcriptional activity. The human BCL9 gene was first identified by cloning the t(1;14)(q21;q32) translocation from a patient with precursor B-cell acute lymphoblastic leukemia (ALL). Amplifications of the chromosome 1q21-locus in which the BCL9 gene resides is observed in a broad range of human cancer types and it has been associated with tumor progression, decreased survival and poor clinical outcome. Most recently, insertional mutagenesis by the PiggyBac transposon has identified a hit in BCL9. Whereas in colorectal cancer (CRC) established mutations in APC and β-catenin drive the oncogenic phenotype, in multiple myeloma (MM) no such mutations have been reported and Wnt activation is instead driven by BCL9, implicating this β-catenin co-factor as a bona-fide oncogene. BCL9 overexpression has since been identified in a large subgroup of human tumors, yet is not expressed in the normal cellular counterparts from which the tumors originate. BCL9-mediated enhancement of β-catenin's transcriptional activity increases cell proliferation, migration, invasion, and the metastatic potential of tumor cells by promoting the loss of an epithelial phenotype and gain of a mesenchyme-like functionality. shRNA-induced downregulation of BCL9 in vivo suppresses the expression of Wnt targets c-Myc, cyclin D1, CD44, and VEGF, and correspondingly increases the survival of xenograft mice with CRC and MM by reducing tumor load, metastasis, and the host angiogenesis response. The striking BCL9 dependence of these cancers and the expression of BCL9 in ~30% of epithelial tumors provides a compelling rationale for targeting the BCL9/β-catenin protein interaction. Importantly, Bcl9-null mice lack an overt disease phenotype, suggesting that pharmacologic blockade of the BCL9/β-catenin complex may be relatively non-toxic.

The Wnt pathway consists of a tightly regulated receptor-mediated signal transduction system required for both embryonic development and adult tissue homeostasis in vertebrates and invertebrates and involves canonical and non-canonical Wnt pathways. Several components of the canonical Wnt signaling cascade have been shown to function as either tumor suppressor genes (TSG) or as oncogenes in a wide range of common human cancers including colorectal, hepatocellular, breast, endometrial carcinomas and MM. Furthermore, the canonical Wnt pathway has been implicated in the regulation of normal (e.g., wound healing) as well as pathological processes (e.g., diabetes). These observations underscore the relevance of this pathway to oncogenesis and the need for further investigation of Wnt signaling components as potential targets for cancer therapy, wound healing, angiogenesis and diabetes.

It is an object of the invention to design and generate hydrocarbon-stapled peptides of the HD2 domain of BCL9 (stapled α-helices of BCL9 or SAH-BCL9) to block Wnt signaling. It is also an object to demonstrate that direct binding of stabilized α-helical peptides to β-catenin prevents β-catenin/BCL9 interaction, Wnt transcriptional activity, and expression of downstream targets. Such mechanisms would result in a method of treatment of cancer cells with SAH-BCL9 and result in inhibition of tumor cell proliferation, migration, tumor-induced angiogenesis, tumor load, de-differentiation (epithelial-mesenchymal transition [EMT]), and metastasis in Wnt/β-catenin-driven cancers.

SUMMARY OF THE INVENTION

The invention provides structurally-constrained, protease-resistant, and cell-permeable BCL9 α-helical peptides, and methods of use of those peptides as therapeutic and prophylactic agents. Such structurally-constrained peptides display excellent proteolytic, acid, and thermal stability, and possess superior pharmacokinetic properties compared to the corresponding unmodified peptides. The peptides of the invention are stabilized with at least one hydrocarbon staple, but could include two, three or more hydrocarbon staples. The inclusion of multiple hydrocarbon staples is particularly suited for alpha helical peptides that are 20 or more amino acids in length. The hydrocarbon staples allow for the amino acid residues on an interacting face to be properly oriented due to stabilization of the helical structure of the BCL9 HD2 domain.

In one aspect, the invention provides a structurally constrained peptide of an HD2 domain of BCL9 (BCL9-HD2), comprising at least one hydrocarbon staple or stitch.

In one embodiment, the peptide comprises an interacting face comprised of amino acids that interact with β-catenin.

In another embodiment, the interacting face comprises about 3 to about 20 amino acids.

In certain embodiments, the interacting face comprises 4-15 amino acids.

In various embodiments, the interacting face comprises 40% or greater identity to a helical face of BCL9 HD2 that binds β-catenin, wherein the interacting face comprises BCL9 residues Gln-355, His-358, Arg-359, Ser-362, Leu-363, Leu-366, Ile-369, Gln-370, Leu-373, and Phe-374, or conservative substitutions thereof.

In still other embodiments, the interacting face comprises 50% to 90% identity to the helical face of BCL9 HD2 that binds β-catenin, wherein the interacting face comprises BCL9 residues Gln-355, His-358, Arg-359, Ser-362, Leu-363, Leu-366, Ile-369, Gln-370, Leu-373, and Phe-374, or conservative substitutions thereof.

In another embodiment, the interacting face represents a single face of an α-helix.

In various embodiments, the single face of a helix comprises one, two, three, or four adjacent stacked columns of amino acids, wherein the stacked columns of amino acids are defined by positions a, d, and g; positions b and e; or positions c and f; in an alpha helix having 3.6 amino acids per turn wherein the amino acids are consecutively and serially assigned positions a-g; and positions a and d; positions b and e; or positions c and f in a $3_{10}$ helix having 3 amino acids per turn wherein the amino acids are consecutively and serially assigned positions a-f; or homologues thereof.

In other embodiments, the invention provides a structurally constrained peptide consisting of: between about 20% to 100% sequence homology to amino acids 351 to 374 of BCL9 HD2, SEQ ID NO: 1 (LSQEQLEHRERSLQTLRDIQRMLF), wherein the peptide comprises between one and five hydrocarbon staples.

In other embodiments, the invention provides a structurally constrained peptide consisting of: between about 50% to 100% sequence homology to amino acids 351 to 374 of BCL9 HD2, SEQ ID NO: 1 (LSQEQLEH-RERSLQTLRDIQRMLF), wherein the peptide comprises between one and five hydrocarbon staples.

In various embodiments, the hydrocarbon staple or stitch is between one or more natural or non-natural amino acids.

In certain embodiments, the hydrocarbon staple or stitch is formed by an olefin metathesis reaction.

In another embodiment, the non-natural amino acids are selected from the following:

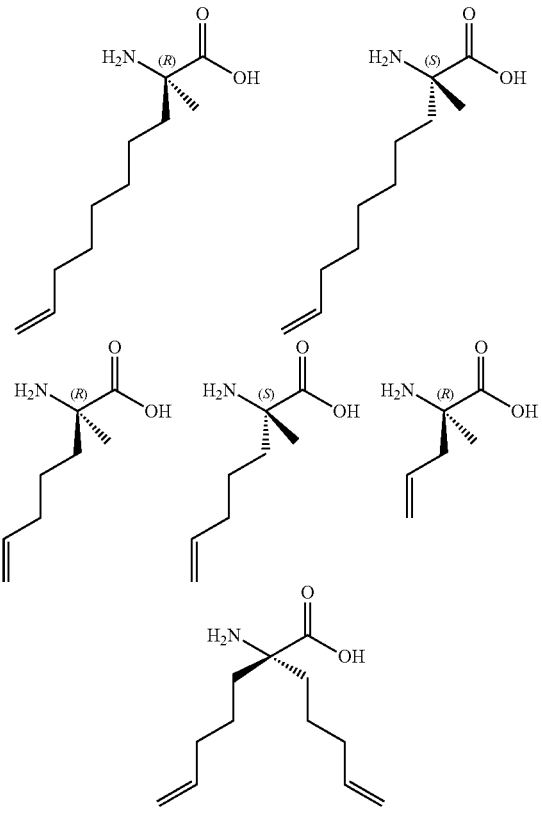

In various embodiments, the structurally constrained peptide comprises 1 to 5 staples or stitches within the BCL9 HD2 peptide.

In other embodiments, one staple or stitch is located at the following positions within the BCL9 HD2 peptide: a) i, i+4; b) i, i+7; and c) i, i+3.

In certain embodiments, another staple or stitch is located at the following positions within the BCL9 HD2 peptide: a) i, i+4; b) i, i+7; and c) i, i+3.

In various embodiments, any other staples or stitches are located at the following positions within the BCL9 HD2 peptide: a) i, i+4; b) i, i+7; and c) i, i+3.

In another embodiment, the invention provides a structurally constrained peptide, wherein one hydrocarbon staple is located at the following exemplary positions within the BCL9 HD2 peptide, and iterated by staple scanning:

```
BCL9-HD2 domain
                                  (SEQ ID NO: 2)
351 LSQEQLEHRERSLQTLRDIQRBLF 374
i, i + 4 single staples:
                                  (SEQ ID NO: 8)
XSQEXLEHRERSLQTLRDIQRBLF (SEQ ID NO: 9)
LXQEQXEHRERSLQTLRDIQRBLF (SEQ ID NO: 10)
LSXEQLXHRERSLQTLRDIQRBLF (SEQ ID NO: 11)
LSQXQLEXRERSLQTLRDIQRBLF
```

-continued (SEQ ID NO. 12)
LSQEXLEHXERSLQTLRDIQRBLF (SEQ ID NO. 13)
LSQEQXEHRXRSLQTLRDIQRBLF (SEQ ID NO. 14)
LSQEQLXHREXSLQTLRDIQRBLF (SEQ ID NO. 15)
LSQEQLEXRERXLQTLRDIQRBLF (SEQ ID NO. 16)
LSQEQLEHXERSXQTLRDIQRBLF (SEQ ID NO. 17)
LSQEQLEHRXRSLXTLRDIQRBLF (SEQ ID NO. 18)
LSQEQLEHREXSLQXLRDIQRBLF (SEQ ID NO. 19)
LSQEQLEHRERXLQTXRDIQRBLF (SEQ ID NO. 20)
LSQEQLEHRERSXQTLXDIQRBLF (SEQ ID NO. 21)
LSQEQLEHRERSLXTLRXIQRBLF (SEQ ID NO. 22)
LSQEQLEHRERSLQXLRDXQRBLF (SEQ ID NO. 23)
LSQEQLEHRERSLQTXRDIXRBLF (SEQ ID NO. 24)
LSQEQLEHRERSLQTLXDIQXBLF (SEQ ID NO. 25)
LSQEQLEHRERSLQTLRXIQRXLF (SEQ ID NO. 26)
LSQEQLEHRERSLQTLRDXQRBXF (SEQ ID NO. 27)
LSQEQLEHRERSLQTLRDIXRBLX i, i + 7 staples:

(SEQ ID NO. 28)
XSQEQLEXRERSLQTLRDIQRBLF (SEQ ID NO. 29)
LXQEQLEHXERSLQTLRDIQRBLF (SEQ ID NO. 30)
LSXEQLEHRXRSLQTLRDIQRBLF (SEQ ID NO. 31)
LSQXQLEHREXSLQTLRDIQRBLF (SEQ ID NO. 32)
LSQEXLEHRERXLQTLRDIQRBLF (SEQ ID NO. 33)
LSQEQXEHRERSXQTLRDIQRBLF (SEQ ID NO. 34)
LSQEQLXHRERSLXTLRDIQRBLF (SEQ ID NO. 35)
LSQEQLEXRERSLQXLRDIQRBLF (SEQ ID NO. 36)
LSQEQLEHXERSLQTXRDIQRBLF (SEQ ID NO. 37)
LSQEQLEHRXRSLQTLXDIQRBLF

-continued (SEQ ID NO. 38)
LSQEQLEHREXSLQTLRXIQRBLF (SEQ ID NO. 39)
LSQEQLEHRERXLQTLRDXQRBLF (SEQ ID NO. 40)
LSQEQLEHRERSXQTLRDIXRBLF (SEQ ID NO. 41)
LSQEQLEHRERSLXTLRDIQXBLF (SEQ ID NO. 42)
LSQEQLEHRERSLQXLRDIQRXLF (SEQ ID NO. 43)
LSQEQLEHRERSLQTXRDIQRBXF (SEQ ID NO. 44)
LSQEQLEHRERSLQTLXDIQRBLX i, i + 3 single staples:

(SEQ ID NO. 45)
XSQXQLEHRERSLQTLRDIQRBLF (SEQ ID NO. 46)
LXQEXLEHRERSLQTLRDIQRBLF (SEQ ID NO. 47)
LSXEQXEHRERSLQTLRDIQRBLF (SEQ ID NO. 48)
LSQEXLEXRERSLQTLRDIQRBLF (SEQ ID NO. 49)
LSQEQXEHXERSLQTLRDIQRBLF (SEQ ID NO. 50)
LSQEQLXHRXRSLQTLRDIQRBLF (SEQ ID NO. 51)
LSQEQLEXREXSLQTLRDIQRBLF (SEQ ID NO. 52)
LSQEQLEHXERXLQTLRDIQRBLF (SEQ ID NO. 53)
LSQEQLEHRXRSXQTLRDIQRBLF (SEQ ID NO. 54)
LSQEQLEHREXSLXTLRDIQRBLF (SEQ ID NO. 55)
LSQEQLEHRERXLQXLRDIQRBLF (SEQ ID NO. 56)
LSQEQLEHRERSXQTXRDIQRBLF (SEQ ID NO. 57)
LSQEQLEHRERSLXTLXDIQRBLF (SEQ ID NO. 58)
LSQEQLEHRERSLQXLRXIQRBLF (SEQ ID NO. 59)
LSQEQLEHRERSLQTXRDXQRBLF (SEQ ID NO. 60)
LSQEQLEHRERSLQTLXDIXRBLF (SEQ ID NO. 61)
LSQEQLEHRERSLQTLRXIQXBLF (SEQ ID NO. 62)
LSQEQLEHRERSLQTLRDXQRXLF (SEQ ID NO. 63)
LSQEQLEHRERSLQTLRDIXRBXF (SEQ ID NO. 64)
LSQEQLEHRERSLQTLRDIQXBLX.

In certain embodiments, the invention provides a structurally constrained peptide, wherein two hydrocarbon staples are located at the following exemplary positions within the BCL9 HD2 peptide, and iterated by staple scanning:

```
BCL9-HD2 domain
                                        (SEQ ID NO. 2)
351 LSQEQLEHRERSLQTLRDIQRBLF 374
i, i + 3 double staples:
                                        (SEQ ID NO. 65)
XSQXQLEHRERSLQTLRDIQXBLX (SEQ ID NO. 66)
XSQXQLEHRERSLQTLRDIXRBXF (SEQ ID NO. 67)
XSQXQLEHRERSLQTLRDXQRBXF i, i + 4 double staples:
                                        (SEQ ID NO. 68)
XSQEXLEHRERSLQTLRDIXRBLX (SEQ ID NO. 69)
XSQEXLEHRERSLQTLRDXQRBXF (SEQ ID NO. 70)
XSQEXLEHRERSLQTLXDIQRXLF i, i + 7 double staples:
                                        (SEQ ID NO. 71)
XSQEQLEXRERSLQTLXDIQRBLX (SEQ ID NO. 72)
XSQEQLEXRERSLQTXRDIQRBXF (SEQ ID NO. 73)
XSQEQLEXRERSLQXLRDIQRXLF.
```

In another embodiment, the invention provides a structurally constrained peptide, wherein the one or more hydrocarbon staples or stitches is located at any of the following exemplary positions within the BCL9 HD9 domain and iterated by staple scanning:

```
BCL9-HD2 domain
                                        (SEQ ID NO. 2)
351 LSQEQLEHRERSLQTLRDIQRBLF 374
Mixed i, i + 4; i, i + 3; and
i, i + 7 double staples:
                                        (SEQ ID NO. 74)
XSQEXLEHRERSLQTLXDIQRBLX (SEQ ID NO. 75)
XSQEXLEHRERSLQTXRDIQRBXF (SEQ ID NO. 76)
XSQEXLEHRERSLQXLRDIQRXLF (SEQ ID NO. 77)
XSQEXLEHRERSLQTLRDIQXBLX (SEQ ID NO. 78)
XSQEXLEHRERSLQTLRDIXRBXF (SEQ ID NO. 79)
XSQEXLEHRERSLQTLRDXQRXLF (SEQ ID NO. 80)
XSQEQLEXRERSLQTLRDIXRBLX (SEQ ID NO. 81)
XSQEQLEXRERSLQTLRDXQRBXF (SEQ ID NO. 82)
XSQEQLEXRERSLQTLRXIQRXLF (SEQ ID NO. 83)
XSQEQLEXRERSLQTLRDIQXBLX (SEQ ID NO. 84)
XSQEQLEXRERSLQTLRDIXRBXF (SEQ ID NO. 85)
XSQEQLEXRERSLQTLRDXQRXLF (SEQ ID NO. 86)
XSQXQLEHRERSLQTLRDIXRBLX (SEQ ID NO. 87)
XSQXQLEHRERSLQTLRDXQRBXF (SEQ ID NO. 88)
XSQXQLEHRERSLQTLRXIQRXLF (SEQ ID NO. 89)
XSQXQLEHRERSLQTLXDIQRBLX (SEQ ID NO. 90)
XSQXQLEHRERSLQTXRDIQRBXF (SEQ ID NO. 91)
XSQXQLEHRERSLQXLRDIQRXLF Sequential i, i + 4 staples:
                                        (SEQ ID NO. 92)
XSQEXLEHXERSLQTLRDIQRBLF (SEQ ID NO. 93)
LXQEQXEHRXRSLQTLRDIQRBLF (SEQ ID NO. 94)
LSXEQLXHREXSLQTLRDIQRBLF (SEQ ID NO. 95)
LSQXQLEXRERXLQTLRDIQRBLF (SEQ ID NO. 96)
LSQEXLEHXERSXQTLRDIQRBLF (SEQ ID NO. 97)
LSQEQXEHRXRSLXTLRDIQRBLF (SEQ ID NO. 98)
LSQEQLXEREXSLQXLRDIQRBLF (SEQ ID NO. 99)
LSQEQLEXRERXLQTXRDIQRBLF (SEQ ID NO. 100)
LSQEQLEHXERSXQTLXDIQRBLF (SEQ ID NO. 101)
LSQEQLEHRXRSLXTLRXIQRBLF (SEQ ID NO. 102)
LSQEQLEHREXSLQXLRDXQRBLF (SEQ ID NO. 103)
LSQEQLEHRERXLQTXRDIXRBLF (SEQ ID NO. 104)
LSQEQLEHRERSXQTLXDIQXBLF (SEQ ID NO. 105)
LSQEQLEHRERSLXTLRXIQRXLF (SEQ ID NO. 106)
LSQEQLEHRERSLQXLRDXQRBXF (SEQ ID NO. 107)
LSQEQLEHRERSLQTXRDIXRBLX Sequential i, i + 3 staples:
                                        (SEQ ID NO. 108)
XSQXQLXHRERSLQTLRDIQRBLF
```

```
Sequential i, i + 7 staples:
                                 (SEQ ID NO. 109)
XSQEQLEXRERSLQXLRDIQRBLF Mixed sequential staples:
                                 (SEQ ID NO. 110)
XSQXQLEXRERSLQTLRDIQRBLF (SEQ ID NO. 111)
XSQXQLEHREXSLQTLRDIQRBLF (SEQ ID NO. 112)
XSQEXLEXRERSLQTLRDIQRBLF (SEQ ID NO. 113)
XSQEXLEHRERXLQTLRDIQRBLF (SEQ ID NO. 114)
XSQEQLEXREXSLQTLRDIQRBLF (SEQ ID NO. 115)
XSQEQLEXRERXLQTLRDIQRBLF
```

In various embodiments, the invention provides a structurally constrained peptide, further comprising one to four additional hydrocarbon staples.

In other embodiments, the invention provides a structurally constrained peptide, wherein the additional hydrocarbon staples are located at any of the following exemplary positions within the BCL9 HD2 domain and iterated by staple scanning:

```
BCL9-HD2 domain
                                 (SEQ ID NO. 2)
351 LSQEQLEHRERSLQTLRDIQRBLF 374 i, i + 4 single staples:
                                 (SEQ ID NO. 8)
XSQEXLEHRERSLQTLRDIQRBLF (SEQ ID NO. 9)
LXQEQXEHRERSLQTLRDIQRBLF (SEQ ID NO. 10)
LSXEQLXERERSLQTLRDIQRBLF (SEQ ID NO. 11)
LSQXQLEXRERSLQTLRDIQRBLF (SEQ ID NO. 12)
LSQEXLEHXERSLQTLRDIQRBLF (SEQ ID NO. 13)
LSQEQXEHRXRSLQTLRDIQRBLF (SEQ ID NO. 14)
LSQEQLXHREXSLQTLRDIQRBLF (SEQ ID NO. 15)
LSQEQLEXRERXLQTLRDIQRBLF (SEQ ID NO. 16)
LSQEQLEHXERSXQTLRDIQRBLF (SEQ ID NO. 17)
LSQEQLEHRXRSLXTLRDIQRBLF (SEQ ID NO. 18)
LSQEQLEHREXSLQXLRDIQRBLF (SEQ ID NO. 19)
LSQEQLEHRERXLQTXRDIQRBLF (SEQ ID NO. 20)
LSQEQLEHRERSXQTLXDIQRBLF (SEQ ID NO. 21)
LSQEQLEHRERSLXTLRXIQRBLF (SEQ ID NO. 22)
LSQEQLEHRERSLQXLRDXQRBLF (SEQ ID NO. 23)
LSQEQLEHRERSLQTXRDIXRBLF (SEQ ID NO. 24)
LSQEQLEHRERSLQTLXDIQXBLF (SEQ ID NO. 25)
LSQEQLEHRERSLQTLRXIQRXLF (SEQ ID NO. 26)
LSQEQLEHRERSLQTLRDXQRBXF (SEQ ID NO. 27)
LSQEQLEHRERSLQTLRDIXRBLX i, i + 7 staples:
                                 (SEQ ID NO. 28)
XSQEQLEXRERSLQTLRDIQRBLF (SEQ ID NO. 29)
LXQEQLEHXERSLQTLRDIQRBLF (SEQ ID NO. 30)
LSXEQLEHRXRSLQTLRDIQRBLF (SEQ ID NO. 31)
LSQXQLEHREXSLQTLRDIQRBLF (SEQ ID NO. 32)
LSQEXLEHRERXLQTLRDIQRBLF (SEQ ID NO. 33)
LSQEQXEHRERSXQTLRDIQRBLF (SEQ ID NO. 34)
LSQEQLXHRERSLXTLRDIQRBLF (SEQ ID NO. 35)
LSQEQLEXRERSLQXLRDIQRBLF (SEQ ID NO. 36)
LSQEQLEHXERSLQTXRDIQRBLF (SEQ ID NO. 37)
LSQEQLEHRXRSLQTLXDIQRBLF (SEQ ID NO. 38)
LSQEQLEHREXSLQTLRXIQRBLF (SEQ ID NO. 39)
LSQEQLEHRERXLQTLRDXQRBLF (SEQ ID NO. 40)
LSQEQLEHRERSXQTLRDIXRBLF (SEQ ID NO. 41)
LSQEQLEHRERSLXTLRDIQXBLF (SEQ ID NO. 42)
LSQEQLEHRERSLQXLRDIQRXLF (SEQ ID NO. 43)
LSQEQLEHRERSLQTXRDIQRBXF (SEQ ID NO. 44)
LSQEQLEHRERSLQTLXDIQRBLX i, i + 3 single staples:
                                 (SEQ ID NO. 45)
XSQXQLEHRERSLQTLRDIQRBLF (SEQ ID NO. 46)
LXQEXLEHRERSLQTLRDIQRBLF (SEQ ID NO. 47)
LSXEQXEHRERSLQTLRDIQRBLF
```

-continued

LSQEXLEXRERSLQTLRDIQRBLF (SEQ ID NO. 48)

LSQEQXEHXERSLQTLRDIQRBLF (SEQ ID NO. 49)

LSQEQLXHRXRSLQTLRDIQRBLF (SEQ ID NO. 50)

LSQEQLEXREXSLQTLRDIQRBLF (SEQ ID NO. 51)

LSQEQLEHXERXLQTLRDIQRBLF (SEQ ID NO. 52)

LSQEQLEHRXRSXQTLRDIQRBLF (SEQ ID NO. 53)

LSQEQLEHREXSLXTLRDIQRBLF (SEQ ID NO. 54)

LSQEQLEHRERXLQXLRDIQRBLF (SEQ ID NO. 55)

LSQEQLEHRERSXQTXRDIQRBLF (SEQ ID NO. 56)

LSQEQLEHRERSLXTLXDIQRBLF (SEQ ID NO. 57)

LSQEQLEHRERSLQXLRXIQRBLF (SEQ ID NO. 58)

LSQEQLEHRERSLQTXRDXQRBLF (SEQ ID NO. 59)

LSQEQLEHRERSLQTLXDIXRBLF (SEQ ID NO. 60)

LSQEQLEHRERSLQTLRXIQXBLF (SEQ ID NO. 61)

LSQEQLEHRERSLQTLRDXQRXLF (SEQ ID NO. 62)

LSQEQLEHRERSLQTLRDIXRBXF (SEQ ID NO. 63)

LSQEQLEHRERSLQTLRDIQXBLX (SEQ ID NO. 64)

i, i + 3 double staples:

XSQXQLEHRERSLQTLRDIQXBLX (SEQ ID NO. 65)

XSQXQLEHRERSLQTLRDIXRBXF (SEQ ID NO. 66)

XSQXQLEHRERSLQTLRDXQRBXF (SEQ ID NO. 67)

i, i + 4 double staples:

XSQEXLEHRERSLQTLRDIXRBLX (SEQ ID NO. 68)

XSQEXLEHRERSLQTLRDXQRBXF (SEQ ID NO. 69)

XSQEXLEHRERSLQTLXDIQRXLF (SEQ ID NO. 70)

i, i + 7 double staples:

XSQEQLEXRERSLQTLXDIQRBLX (SEQ ID NO. 71)

XSQEQLEXRERSLQTXRDIQRBXF (SEQ ID NO. 72)

XSQEQLEXRERSLQXLRDIQRZLF. (SEQ ID NO. 73)

In certain of claim 2, wherein the amino acid sequence of positions 351 to 374 is selected from the following:

SEQ ID NO: 1: BCL9 HD2 domain:
LSQEQLEHRERSLQTLRDIQRMLF

SEQ ID NO: 2: BCL9 HD2 domain M372B
LSQEQLEHRERSLQTLRDIQRBLF

SEQ ID NO: 3 SAH-BCL9$_A$:
LSQEQLEHRERSLQTLRXIQRXLF

SEQ ID NO: 4: SAH-BCL9$_B$:
LSQEQLEHRERSLXTLRXIQRBLF

SEQ ID NO: 5: SAH-BCL9$_C$:
LSQEQLEHREXSLQXLRDIQRBLF

SEQ ID NO: 6: SAH-BCL9$_B$(H358D):
LSQEQLEDRERSLXTLRXIQRBLF

SEQ ID NO: 7: SAH-BCL9$_B$(R359E):
LSQEQLEHEERSLXTLRXIQRBLF

In another aspect, the invention provides a composition comprising the peptide as described above and a pharmaceutically acceptable carrier. The invention further provides a peptide of the invention in a pharmaceutical carrier in a unit dosage form.

In another aspect, the invention provides a method of inhibiting canonical Wnt/β-catenin signaling in a subject, comprising administering a peptide of the invention.

In another aspect, the invention provides a method of inhibiting binding of BCL9 to β-catenin in a subject, comprising administering a peptide of the invention.

In one embodiment, the inhibition of binding of BCL9 to β-catenin is caused by the structurally constrained peptide of the invention.

In another aspect, the invention provides a method of treating a disease or disorder mediated by BCL9/β-catenin binding in a subject, comprising administering to the subject a peptide of the invention.

In one embodiment, the subject has been identified as being in need of an inhibitor of the BCL9/β-catenin interaction or Wnt signaling.

In another embodiment, the disease is cancer, tumor cell proliferation, tumor cell de-differentiation and metastasis, tumor migration, tumor induced angiogenesis, cancer stem cell chemoresistance, and a proliferation disease; or involves wound healing, angiogenesis or diabetes.

The invention provides methods for the amelioration or treatment of cancer, for example in a subject, by administration of a structurally-constrained peptide of the invention to the subject in a therapeutically effective amount. The method can further include one or more of identifying a subject as being in need of amelioration or treatment of cancer, or monitoring the subject for the prevention, amelioration, or treatment of cancer. In certain embodiments, the invention provides methods of amelioration or treatment of cancer where in the subject is identified as being in need of BCL9/β-catenin modulation.

In a further embodiment, the disease is colorectal cancer, multiple myeloma, lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, and solid tumors.

In another aspect, the invention provides a method of treating cancer in a subject, comprising administering to the subject a peptide of the invention.

In one embodiment, the subject has been previously identified as in need of a canonical Wnt/β-catenin signaling inhibitor to treat the cancer.

In another embodiment, the disease involves wound healing, angiogenesis or diabetes.

In other embodiments, the subject is administered with an additional therapeutic agent, radiation or chemotherapy.

In a further embodiment, the additional therapeutic compound is an anti-cancer compound.

In another further embodiment, the compound and the additional therapeutic agent are administered simultaneously or sequentially.

In other embodiments, the compound and the additional therapeutic agent are linked together (ie. a bifunctional compound).

In certain embodiments, the subject is a human.

In another aspect, the invention provides a kit comprising a structurally constrained peptide of the invention and instructions for use in treating cancer.

In another aspect, the invention provides a method of identifying a compound that inhibits binding of BCL9 to β-catenin, comprising the steps of contacting the peptide of the invention with β-catenin and then screening for small molecules or compounds that disrupt the interaction between the peptide of the invention and β-catenin.

Other embodiments of the invention will be understood base on the disclosure provided infra.

BRIEF DESCRIPTION OF THE DRAWINGS

FIG. 1A shows the alpha-helical HD2 domain of BCL9, which directly engages a surface groove of β-catenin, provided the template for structural stabilization by hydrocarbon stapling. FIG. 1B shows that SAH-BCL9 A-C(SEQ ID NOS 3-5, respectively) were generated by replacing native residues on the non-interacting surface of the HD2 domain with olefinic non-natural amino acids, which when subjected to olefin metathesis yield the corresponding stapled peptides. An unmodified template peptide (BCL9 HD2 (SEQ ID NO: 1)) was also generated. FIG. 1C shows that CD analysis revealed marked alpha-helical stabilization of SAH-BCL9 peptides compared to the unmodified template peptide. FIG. 1D shows that FITC-SAH-BCL9$_B$ and β-catenin co-precipitated from the lysates of FITC-SAH-BCL9-treated Colo320 cells by both anti-FITC and anti-β-catenin pulldown assays. TCL, total cellular lysate. FIG. 1E shows that FITC-SAH-BCL9$_B$ and β-catenin preferentially localize to the nucleus of Colo320 cells as monitored by confocal microscopy. FIG. 1F shows that FITC-SAH-BCL9$_B$ and β-catenin preferentially localize to the nucleus of Colo320 cells as monitored by cellular fractionation analyses. FIG. 1G shows that H358D and R359E reverse polarity mutants of FITC-SAH-BCL9$_B$ exhibited similar high percent α-helicity compared to the wild-type SAH by CD analysis. FIG. 1H is a bot showing point mutagenesis impaired FITC-SAH-BCL9/β-catenin co-immunoprecipitation, with the R359E-derivative serving as the most effective negative control. FIG. 1I shows that FITC-SAH-BCL9$_B$ and its R359E control exhibit dose-equivalent cellular uptake by Colo320 cells.

FIG. 2A shows that SAH-BCL9$_B$ dose-responsively disrupted the association of β-catenin with BCL9 and B9L, whereas cellular treatment with SAH-BCL9$_B$(R359E) had no effect. Dissociation of β-catenin from BCL9/B9L correlated with the co-immuno-precipitation of β-catenin with FITC-SAH-BCL9$_B$. FIG. 2B shows that Colo320 cells were transfected with TOP-FLASH, incubated with vehicle or SAH-BCL9 peptides and assayed for luciferase activity, which was normalized to Renilla luciferase control. SAH-BCL9$_B$, but not SAH-BCL9$_B$(R359E), inhibited Wnt-dependent reporter activity. Error bars are mean+/−s.d. for assays performed in triplicate. *, P<0.01. FIG. 2C shows that qPCR analysis revealed repression of the Wnt target genes VEGF, c-Myc and Axing, but not GAPDH, in response to SAH-BCL9$_B$ treatment. Vehicle and SAH-BCL9$_B$(R359E) had no effect. Error bars are mean+/−s.d. for assays performed in quadruplicate. *, P<0.01.

FIG. 3A shows that SAH-BCL9$_B$ treatment reduced the growth of Colo320 and colorectal primary tumors (CCPT), as monitored by [$^3$H]-thymidine uptake at 24 h. *, P<0.01. FIG. 3C shows that SAH-BCL9$_B$, but not vehicle or SAH-BCL9$_B$(R359E), likewise impaired the growth of MM1S cells in the presence or absence of Wnt3A-conditioned medium (Wnt3A-CM) and multiple myeloma primary tumors (MMPT). *, P<0.01. FIG. 3D shows that SAH-BCL9$_B$, but not vehicle or SAH-BCL9$_B$(R359E), likewise impaired the growth of MM1S cells in the presence or absence of Wnt3A-conditioned medium (Wnt3A-CM) and multiple myeloma primary tumors (MMPT). *, P<0.01. FIG. 3E shows that SAH-BCL9$_B$ had no effect on the viability of Colo320 and MM1S cells as assessed by CellTiter-Glo at 72 h. FIG. 3F shows that correspondingly, SAH-BCL9$_B$ did not activate caspase-3 or PARP, as monitored by western analysis. FIG. 3G shows that SAH-BCL9$_B$ treatment decreased VEGF secretion by Colo320 and MM1S cells as measured by ELISA. *, P<0.001 FIG. 3H shows that HUVEC were cultured with supernatants collected from Colo320 or MM1S cells incubated with vehicle or SAH-BCL9$_B$ peptides and the number of tubes (black arrows) formed per high power field analyzed by microscopy at 5 h. SAH-BCL9$_B$ blocked in vitro capillary-like tube formation. *, P<0.01 (n=3) FIG. 3I shows that SAH-BCL9$_B$ blocked the migration of Colo320 cells as monitored using Matrigel Boyden chambers. Vehicle and SAH-BCL9$_B$(R359E) had no effect. *, P<0.01. Vehicle, 0.5% DMSO; SAH-BCL9 peptides, 5 µM. Error bars are mean+/−s.d. for experiments performed in triplicate.

FIG. 4A shows that cohorts (n=6) of NOD/SCID mice bearing intraperitoneal GFP-positive Colo320 cells were treated with vehicle (2.5% DMSO in D5W) or SAH-BCL9$_B$ peptides (20 mg/kg) administered intraperitoneally every other day for a total of six doses. Whole body imaging and necropsy revealed decreased tumor burden and liver metastases in SAH-BCL9$_B$-treated mice but not in vehicle- and SAH-BCL9$_B$(R359E)-treated animals. FIG. 4B shows that histologic analysis of the liver revealed decreased tumor invasion and CD44-positivity in SAH-BCL9$_B$-treated mice. FIG. 4C shows the total number of intraparenchymal nodules for each experimental group (n=6), as quantified by examining liver sections at 5 mm intervals, was markedly decreased in SAH-BCL9$_B$-treated mice. Error bars are mean+/−s.d. *, P<0.01. FIG. 4D shows that SAH-BCL9$_B$ treatment likewise inhibited angiogenesis as evaluated by tumor blood vessel quantitation and anti-CD34 immunostaining. Error bars are mean+/−s.d. *, P<0.0001 (n=6). FIG. 4E shows that SAH-BCL9$_B$ treatment likewise inhibited angiogenesis as evaluated by tumor blood vessel quantitation and anti-CD34 immunostaining. Error bars are mean+/−s.d. *, P<0.0001 (n=6). FIG. 4F shows that cohorts of SCID-hu mice (n=5) bearing human bone chips populated by GFP-positive INA-6 cells were injected locally with vehicle (2.5% DMSO in D5W) or SAH-BCL9$_B$ peptides (5 mg/kg) every other day for a total of ten doses. Tumor burden was evaluated by shuIL-6R serum levels at the indicated days after injection of tumor cells. FIG. 4G shows that the cohorts of SCID-hu mice (n=5) bearing human bone chips populated by GFP-positive INA-6 cells were injected locally with vehicle (2.5% DMSO in D5W) or SAH-BCL9$_B$ peptides (5 mg/kg) every other day for a total of ten doses. Tumor burden was evaluated by shuIL-6R serum levels at the indicated days after injection of tumor cells. SAH-BCL9$_B$ treatment significantly suppressed shuIL-6R production and tumor burden, as reflected by decreased bone chip fluorescence. FIG. 4H shows that the histologic analysis likewise demonstrated substantial reduction of INA-6 cells in the bone chips of SAH-BCL9$_B$-treated mice, with tumor cells confined to the bone. In vehicle- and SAH-BCL9$_B$(R359E)-treated mice, tumor cells migrated outside of the bone chip and invaded adjacent soft tissue (black arrows). FIG. 4I shows that intratumoral angiogenesis was suppressed in SAH-BCL9$_B$-treated mice, as monitored by blood vessel quantitation and anti-CD34 immunostaining.

FIG. 5 shows targeting Wnt transcriptional activity in cancer using Stabilized Alpha-Helices of BCL9. Deregulated Wnt signaling underlies the pathogenesis of a broad range of human cancers yet the development of targeted therapies to disrupt the pathway has remained a challenge. β-catenin is a central effector of the canonical Wnt pathway, activating the expression of genes such as c-Myc, cyclin D1, VEGF, and CD44 that are involved in cell proliferation, migration, and angiogenesis. BCL9 is an important co-activator for β-catenin-mediated transcription, and is highly expressed in tumors but not in the cells of origin, presenting an opportunity to selectively inhibit pathologic β-catenin activity. Guided by the structure of the BCL9/β-catenin complex, Stabilized Alpha-Helices of BCL9 (SAH-BCL9) were generated to block Wnt signaling in cancer through targeted disruption of the BCL9/β-catenin complex. SAH-BCL9 reduces Wnt transcriptional activity and the expression of Wnt/β-catenin transcriptional targets, impeding tumor cell proliferation, migration, invasion, and angiogenesis in vitro and in vivo.

FIG. 6A shows that immunohistochemical studies performed on tissue microarrays from colon (n=23), breast (n=22), lung (n=32), liver (n=29), and ovarian (n=32) carcinomas revealed high levels of BCL9 expression in a wide variety of tumors. Representative cases of tumors with high or low level BCL9 immunostaining are shown. FIG. 6B shows that blocking experiments using the immunizing BCL9 peptide (Abcam) were performed on human colorectal cancer specimens according to the manufacturer's protocol and documented BCL9 antibody specificity.

FIG. 7A shows that FITC-SAH-BCL9$_B$ and FITC-SAH-BCL9$_B$(R359E) peptides exhibit equivalent temperature-dependent uptake in Colo320 cells, consistent with the energy-dependent endocytic uptake mechanism previously documented for stapled peptides (Bernal, F., et al. J Am Chem Soc 129, 2456-7 (2007); Walensky, L. D. et al. Science 305, 1466-70 (2004)). FIG. 7B shows that FITC-SAH-BCL9$_B$ and FITC-SAH-BCL9$_B$ (R359E) peptides exhibit equivalent cellular uptake by Colo320 and MM1S cells.

FIG. 8A shows that importantly, β-catenin targeting by FITC-SAH-BCL9$_B$ is selective for disruption of the BCL9/β-catenin complex and does not affect anti-β-catenin co-immunoprecipitation of E-cadherin from MCF7 cell lysates. FIG. 8B shows that treatment of MCF7 cells with FITC-SAH-BCL9$_B$ followed by anti-FITC pulldown performed on cellular lysates revealed the selective interaction between FITC-SAH-BCL9$_B$ and β-catenin, and no coimmunoprecipitation of unrelated proteins such as IxBα and actin. Single R359E point mutagenesis of the SAH-BCL9 binding interface abrogates co-immunoprecipitation of β-catenin, further confirming the specificity of the SAH-BCL9$_B$ peptide. MCF7 cells were employed in this assay as they contain readily detectable levels of E-cadherin protein for monitoring the β-catenin/E-cadherin interaction.

FIG. 11A shows that chromatin immunoprecipitation analysis (ChIP) of Colo320 cells using anti-TCF-4, β-catenin, and BCL9 antibodies documented that, like c-Myc, the VEGF promoter is a target of the Wnt/β-catenin/BCL9 transcriptional complex. Negative controls included ChIP with IgG and the use of primers to a non-specific, upstream region of the VEGF promoter. FIG. 11B shows that Colo320 cells lentivirally transduced with control shRNA or BCL9 shRNA vector were transfected with VEGF promoter-luciferase reporter plasmids. Reporter activity was assayed using the dual luciferase assay system and results normalized to Renilla values for each sample. BCL9 knockdown effectively decreased transcriptional activity at the VEGF promoter. *, P<0.001.

FIG. 13A shows that expression of BCL9 and β-catenin proteins in MM1S and INA-6 cells, as detected by western analysis. FIB. 13B shows that INA-6 cells exposed to SAH-BCL9$_B$ (5 µM) for 24 h displayed significantly reduced growth compared to vehicle- and SAH-BCL9$_B$(R359E)-treated cells, as measured by thymidine incorporation. *, P<0.001. Error bars are mean+/−s.d. for assays performed in triplicate.

FIG. 15A-FIG. 15D show examples of singly-, doubly-, and sequentially stapled BCL9 HD2 peptides. X, stapling amino acid; B, norleucine. A staple scan readily enables iterative production and testing of distinct staple compositions and their differential positions along the peptide sequence to identify optimally stabilized alpha-helix of BCL9 HD2 constructs. FIG. 15A-FIG. 15D discloses SEQ ID NO: 2, residues 2-6 of SEQ ID NO:2 and SEQ ID NOS 8-115, respectively, in order of appearance.

FIG. 16 discloses residues 1-4 of SEQ ID NO: 140.

FIG. 17A-FIG. 17B show that SAH-BCL9$_B$ disrupts β-catenin-BCL9/B9L complexes. FIG. 17 A shows that differential binding affinities of SAH-BCL9$_B$ and SAH-BCL9$_B$(R359E) for recombinant β-catenin. FIG. 17B shows that SAH-BCL9$_B$ dose-responsively dissociated recombinant β-catenin/BCL9 complexes as demonstrated by GST-pull-down assay. R359E point mutagenesis reduced SAH-BCL9$_B$ activity by 6-fold.

FIG. 18A-FIG. 18F show that SAH-BCL9$_B$ selectively blocks Wnt transcription. FIG. 18A shows that qRT-PCR analysis revealed dose-dependent repression of Wnt target genes in response to SAH-BCL9$_B$ treatment of Colo320 cells. Error bars are mean+/−s.d. for assays performed in quadruplicate. * p<0.01. FIG. 18B shows quantitative comparison of genes down-regulated by SAH-BCL9$_B$ and dominantnegative TCF1/TCF4 expression in DLDI cells across adenoma signatures. FIG. 18C is a schematic showing quantitative comparison of genes down-regulated by SAH-BCL9$_B$ and dominant-negative TCF1/TCF4 expression in DLDI cells across carcmoma signatures. FIG. 18D shows heat map representation of the 50 most down regulated genes (p<0.001) of the leading edge—the genes contributing most to the correlation between SAH-BCL9$_B$ and dominant-negative TCF1/TCF4, for the adenoma signatures. FIG. 18E is a schematic heat map representation of the 50 most down regulated genes (p<0.001) of the leading edge—the genes contributing most to the correlation between SAH-BCL9$_B$ and dominant-negative TCF1/TCF4, for the carcinoma signatures. FIG. 18F shows qRT-PCR validation of key Wnt target genes in DLD1 cells treated with SAH-BCL9$_B$.

FIG. 19A shows that qRT-PCR analysis revealed repression of Wnt target genes in response to SAH-BCL9$_B$ treatment of MM1S cells at 10 μM. Error bars are mean+/−s.d. for assays performed in quadruplicate. * p<0.01. FIG. 19B shows that Affymetrix gene expression profiling analysis of VEGF-A in DLD1 cells.

FIG. 20A shows that SAH-BCL9$_B$, but not vehicle or SAH-BCL9$_{MUT}$, significantly reduced the proliferation of CRC cell lines. SAH-BCL9$_B$-susceptible cancer cells express BCL9, whereas the LS174T cell line that does not express BCL9 showed no response, linking the inhibitory effect of SAH-BCL9$_B$ with BCL9 expression. As further cellular controls for SAH-BCL9$_B$'s specificity-of-action, HCT116 cells and its two derivative cell lines, HCT116DO20 and HCT116KO58, whose proliferative capacity does not depend on Wnt/β-catenin activity (T. A. Chan et al., Proc Natl Acad Sci USA 99, 8265 (2002)), showed no sensitivity to SAH-BCL9$_B$. FIG. 20B shows the expression of BCL9, B9L, and β-catenin in CRC cell lines, as evaluated by western blot.

FIG. 21A shows that Colo320 cells were co-cultured with vehicle, SAH-BCL9$_B$, or SAH-BCL9$_{MUT}$ and increasing concentrations of 5-fluorouracil (5-FU), and evaluated for cellular proliferation using $^3$H-thymidine incorporation. FIG. 21B shows that MM1S cells were co-cultured with vehicle, SAH-BCL9$_B$, or SAH-BCL9$_{MUT}$ and increasing concentrations of doxorubicin (Dox), and evaluated for cellular proliferation using $^3$H-thymidine incorporation. SAH-BCL9$_B$ but not SAH-BCL9$_{MUT}$ or vehicle significantly enhanced the anti-tumor activity of the conventional agents.

FIG. 23A shows that INA-6 cells were lentivirally transduced with empty vector (Mock) or a vector expressing a dominant negative form of TCF4 (EdTP) and proliferation was measured by $^3$H-thymidine incorporation. FIG. 23B shows tumor tissue sections from NOD/SCID mice bone chips bearing INA-6 cells were evaluated for apoptosis induction using TUNEL assay (brown). SAH-BCL9$_B$, but not vehicle or SAH-BCL9$_{MUT}$, notably increased TUNEL positivity. Three representative 40× power fields are shown, including quantitation of TUNEL positivity in 6 high power fields. * p<0.001.

DETAILED DESCRIPTION

Recent studies have revealed that high Wnt signaling activity is functionally ascribed to the colon cancer stem cell (CSC) population, which is resistant to conventional chemotherapy and believed to be responsible for tumor recurrence (Vermeulen L, et al. Nat Cell Biol. 12:468, 2010). Thus, blocking Wnt signaling pathway may be most potent against these cells. Furthermore canonical Wnt pathway has been implicated in physiological an pathological angiogenesis (Dejana E. Circulation Research. 107:943 2010), underscoring the relevance of this pathway for target drug discovery and therapeutic development (Barker, N., & Clevers, H. Nat Rev Drug Discov 5:997, 2006).

Figure 1A:
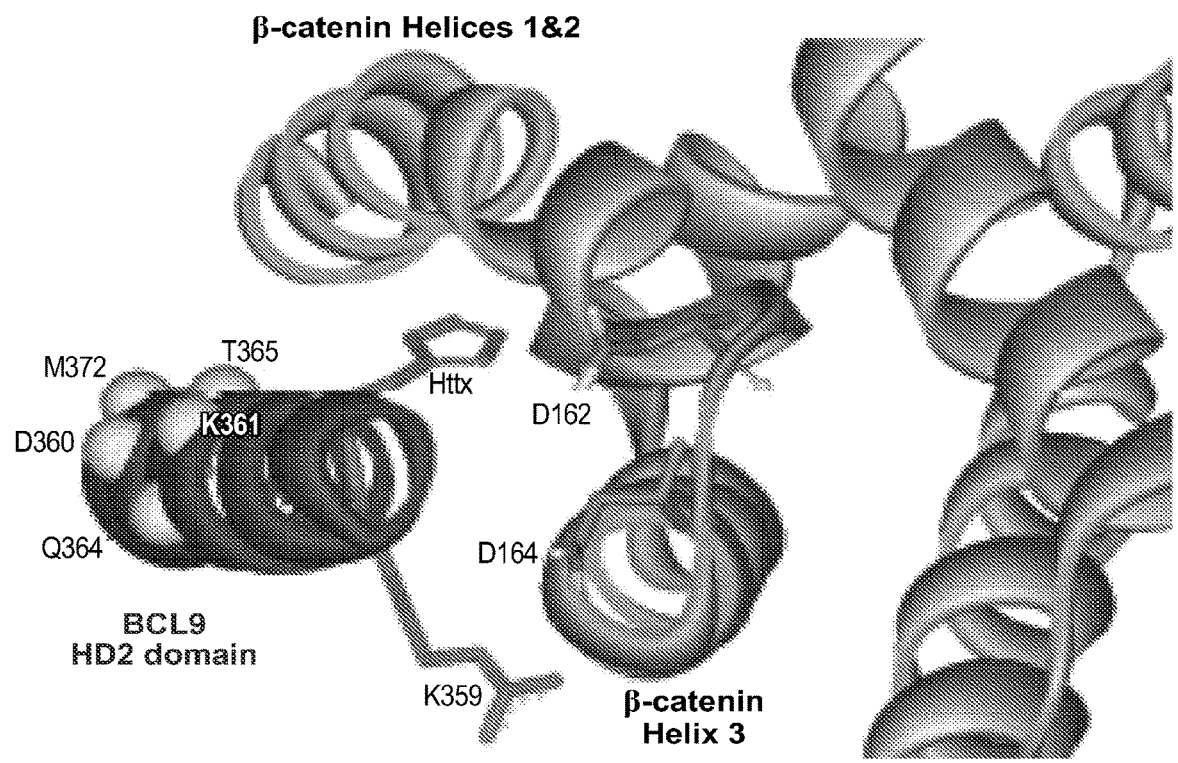
FIG. 1A-FIG. 1I show the design, synthesis, and characterization of SAH-BCL9 peptides.
Figure 1B:
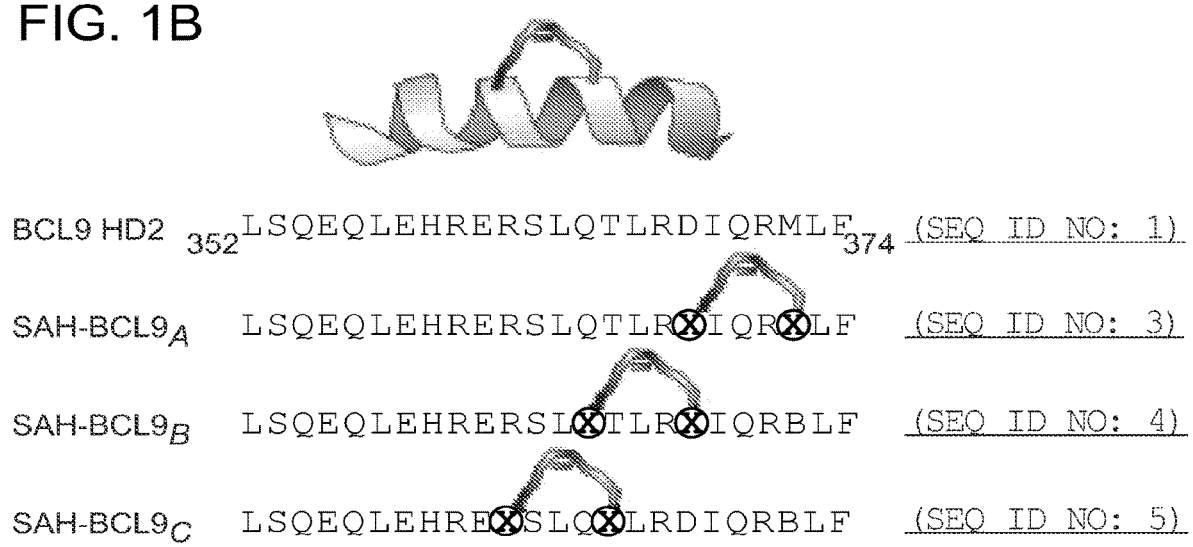
Figure 1C:
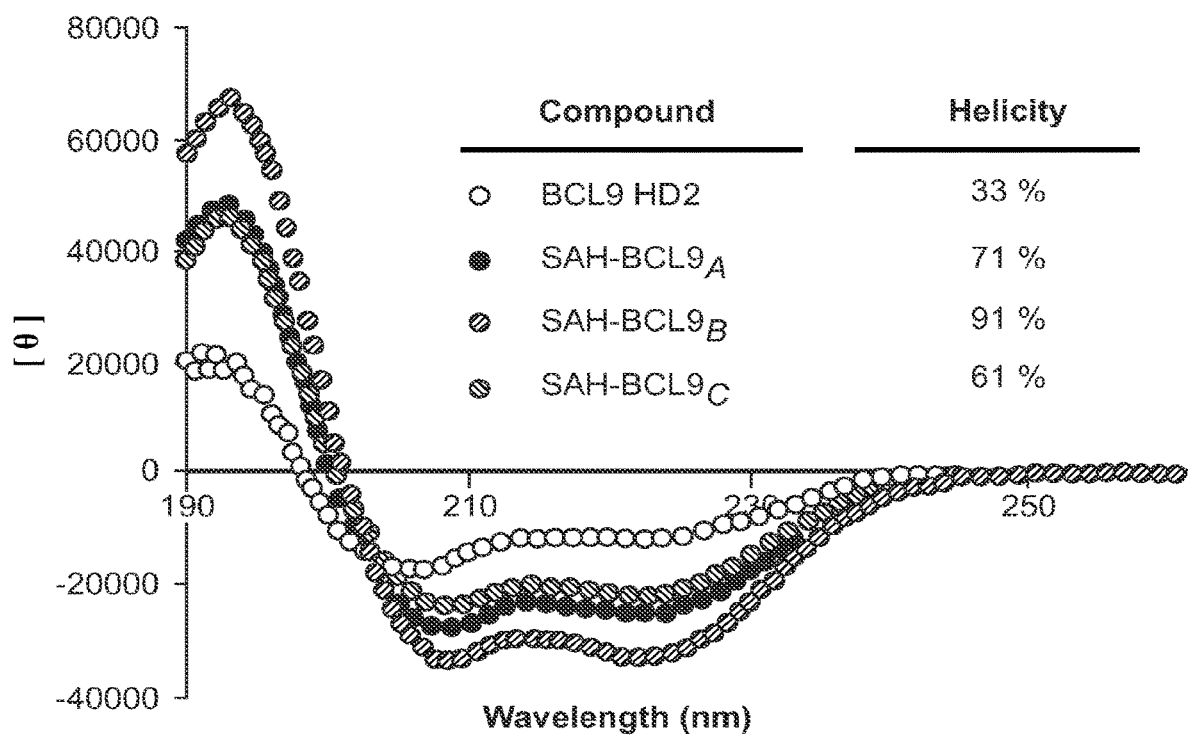
Figure 1D:
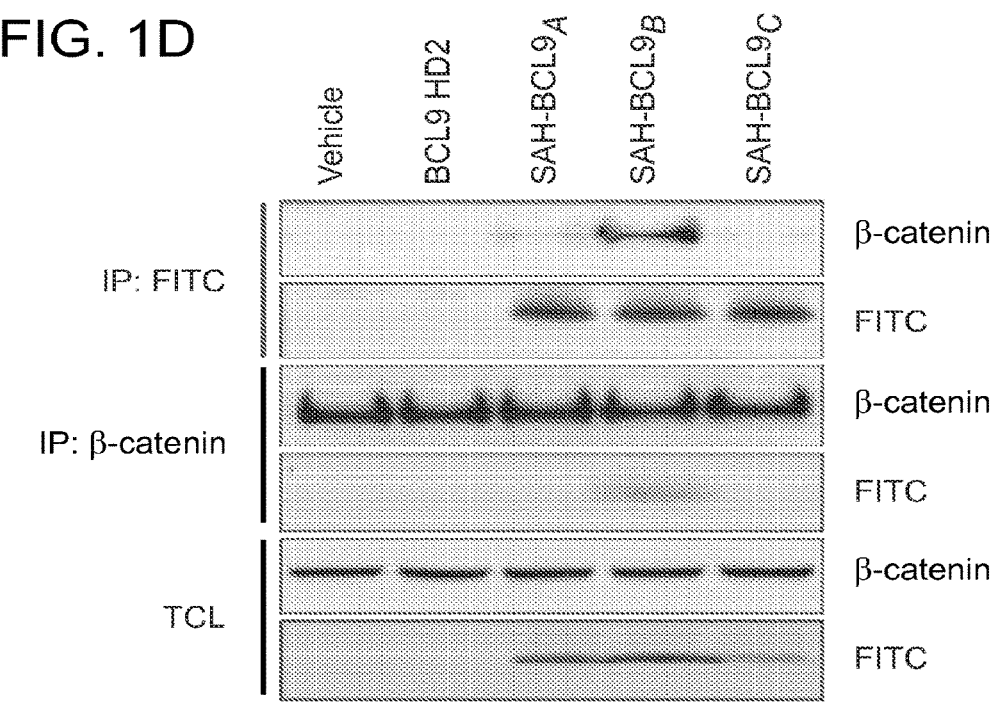
Figure 1E:
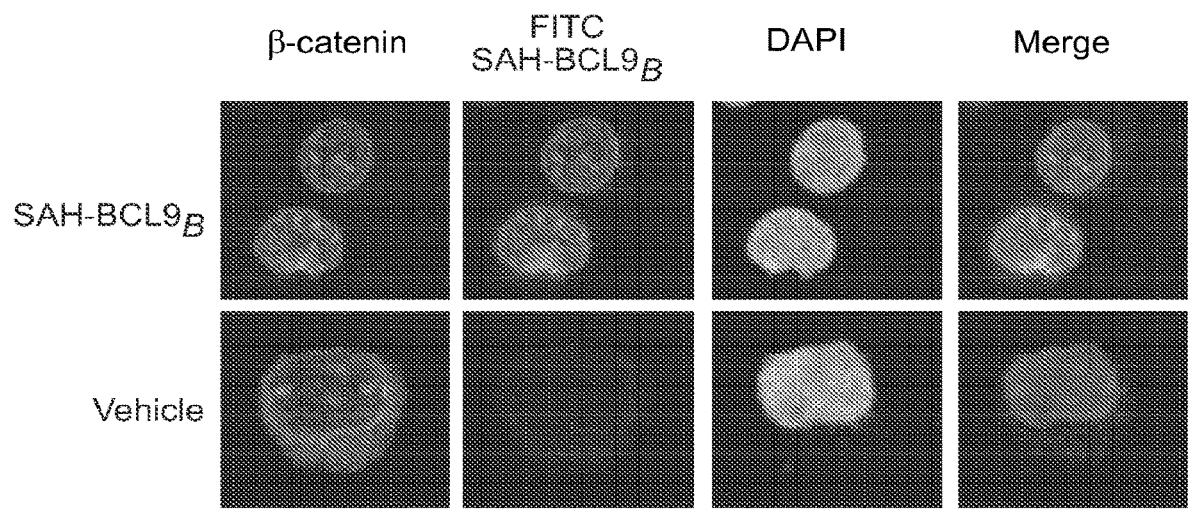
Figure 1F:
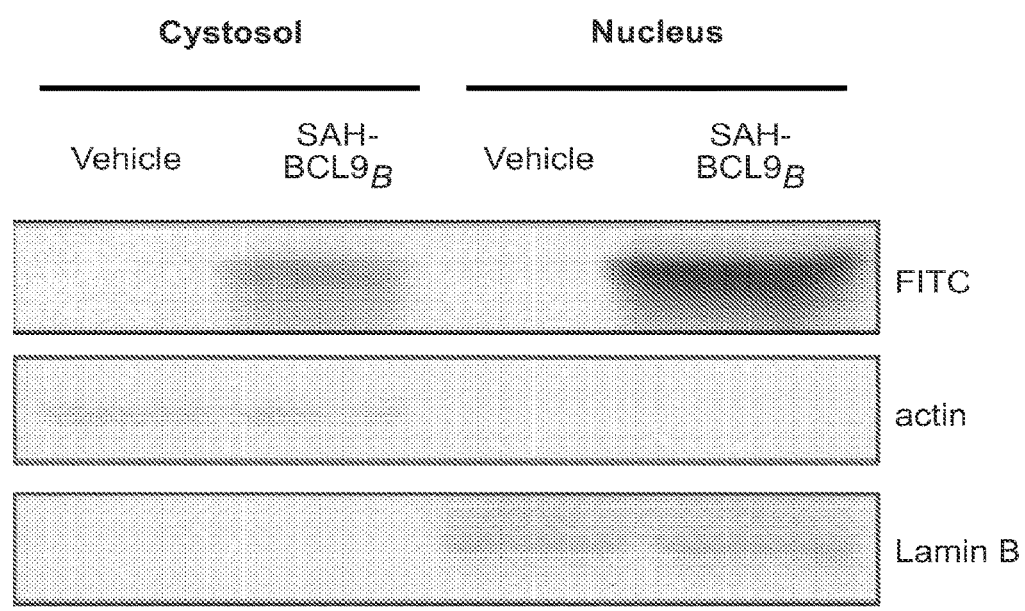
Figure 1G:
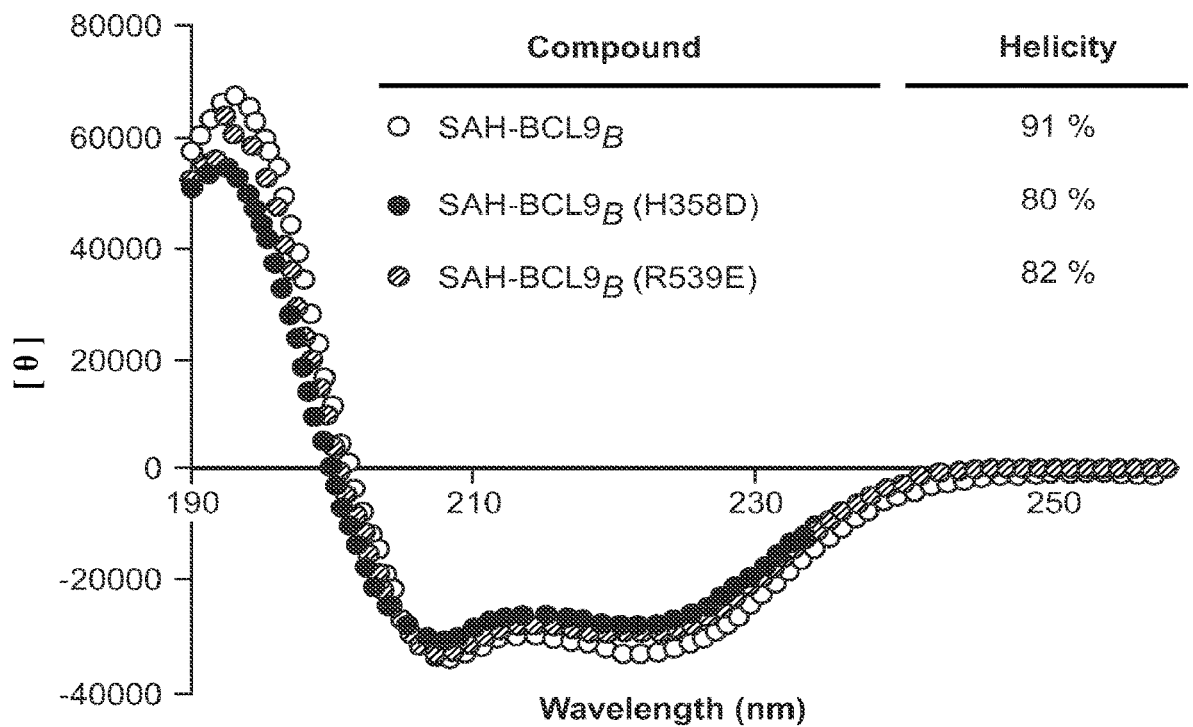
Figure 1H:
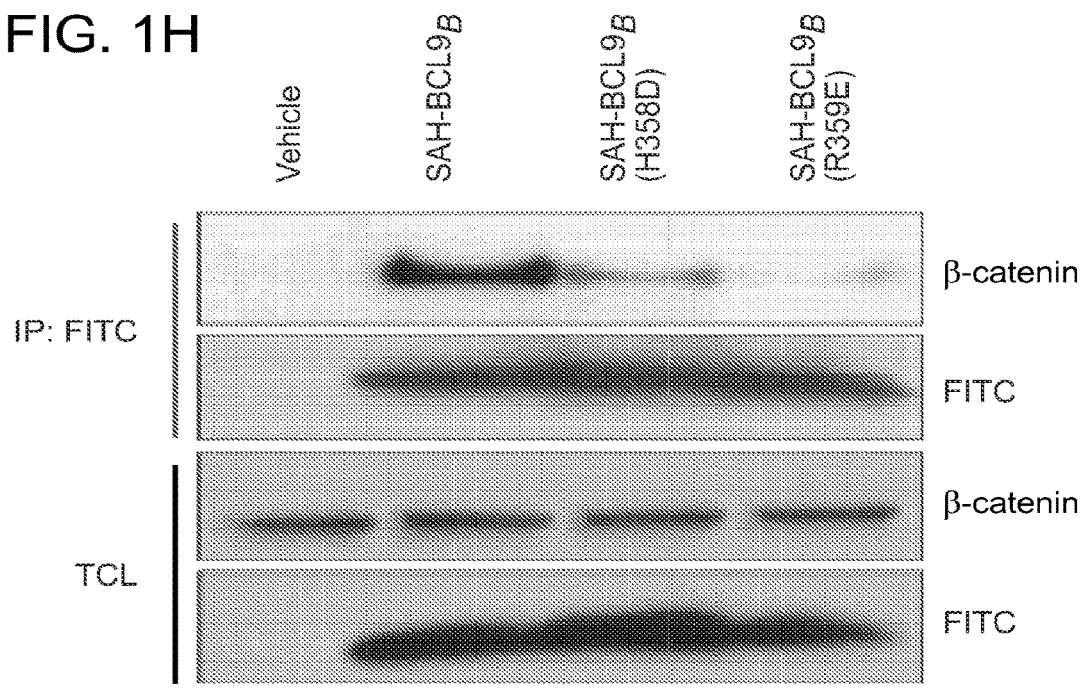
Figure 1I:
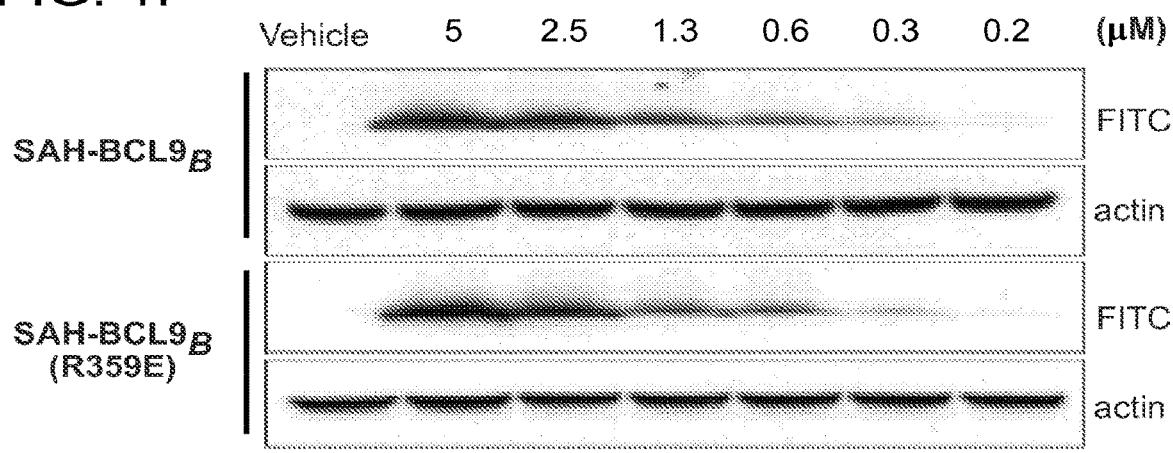

The crystal structure of the β-catenin/BCL9/TCF-4 complex revealed that the BCL9 binding site on β-catenin is distinct from other binding partners in that the α-helical HD2 domain of BCL9 (residues 352-374) binds a surface groove formed by α-helices 2 and 3 of the armadillo repeat 1 of β-catenin (FIG. 1A) (Sampietro, J. et al. Mol Cell 24, 293-300 (2006)). Importantly, alanine mutagenesis of key residues at the BCL9 binding interface, such as H358A or R359A, blocked the ability of BCL9 to bind β-catenin, abrogating transactivation. To harness this natural binding motif to target β-catenin, hydrocarbon stapling was applied (Schafmeister, C., Po, J. & Verdine, G. J Am Chem Soc 122, 5891-5892 (2000); Walensky, L. D. et al. Science 305, 1466-70 (2004)) to generate structurally-reinforced α-helical peptides based on the BCL9 HD2 domain. Non-natural amino acids with olefinic side chains were substituted at (i, 1+4) positions followed by ruthenium-catalyzed olefin metathesis to yield SAH-BCL9 peptides A-C (FIG. 1B). Circular dichroism (CD) analysis confirmed that hydrocarbon stapling consistently enhanced peptide α-helicity compared to the corresponding unmodified peptide (BCL9 HD2) (FIG. 1C). Cells treated with fluorescent derivatives of the peptides, followed by washing, trypsinization, and extraction, contained FITC-SAH-BCL9 A-C but not the corresponding unmodified FITC-peptide in the lysates, documenting the cellular uptake of SAH peptides (FIG. 1D). Both FITC and β-catenin immunoprecipitation identified SAH-BCL9$_B$ as the most effective β-catenin interactor in situ (FIG. 1D). Immunofluorescence confocal microscopy demonstrated a predominant nuclear localization of β-catenin and SAH-BCL9$_B$ in the nucleus (FIG. 1E), with the nuclear enrichment of SAH-BCL9$_B$ confirmed by cellular fractionation (FIG. 1F). To develop a negative control SAH-BCL9$_B$ peptide for biological studies, SAH-BCL9$_B$ (H358D) and SAH-BCL9$_B$(R359E) were generated and contain single reverse polarity point mutants of key binding interface residues (FIG. 1A). Compared to SAH-BCL9$_B$, both mutants displayed similar α-helical enhancement (FIG. 1G) and cellular uptake (FIG. 1H), yet demonstrated impaired β-catenin interaction by co-immunoprecipitation analysis (FIG. 1H), with R359E mutagenesis causing the most deleterious effect. Thus, SAH-BCL9$_B$ and its corresponding R359E mutant were selected for functional studies in the β-catenin/BCL9-dependent cell lines Colo320 and MM1S (Mani, M. et al. Cancer Res 69, 7577-86 (2009); Ilyas, M., et al. Proc Natl Acad Sci USA 94, 10330-4 (1997)), which display dose-equivalent uptake of the two peptides (FIG. 1I).

Figure 2A:
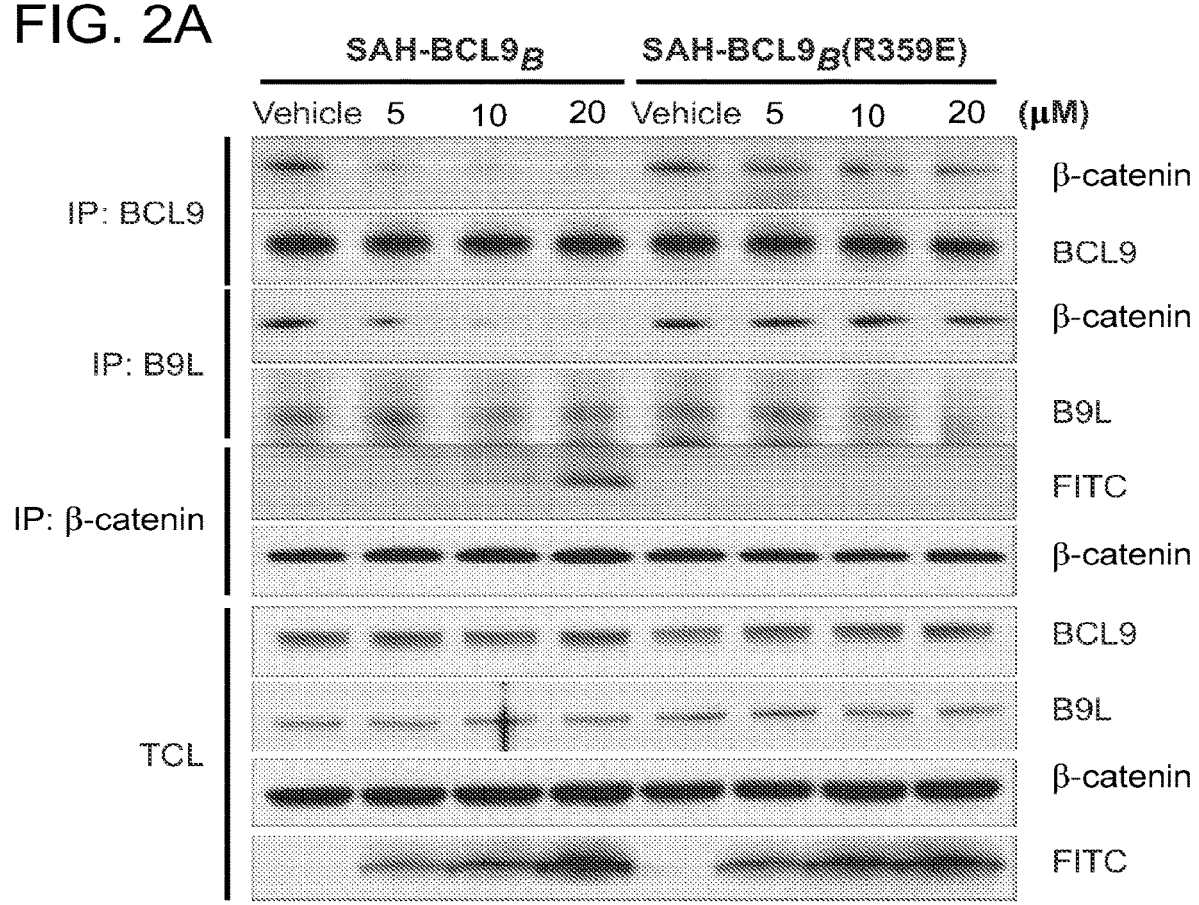
FIG. 2A-FIG. 2C show that SAH-BCL9$_B$ disrupts native β-catenin-BCL9/B9L complexes and represses Wnt/β-catenin/BCL9-driven transcription.

A series of co-immunoprecipitation analyses was performed to determine if I-catenin targeting by SAH-BCL9$_B$ disrupted the endogenous interactions of β-catenin with BCL9 and its close homologue B9L (Brembeck, F. H. et al. Genes Dev 18, 2225-30 (2004)), which contains an identical HD2 domain (Sampietro, J. et al. Mol Cell 24, 293-300 (2006)). Strikingly, SAH-BCL9$_B$, but not its R359E derivative, caused dose-responsive disruption of the β-catenin-BCL9/B9L complexes in anti-BCL9 and B9L co-immunoprecipitation studies (FIG. 2A). Correspondingly, FITC-SAH-BCL9$_B$, but not SAH-BCL9$_B$(R359E), dose-responsively co-immunoprecipitated with β-catenin (FIG. 2A), linking β-catenin targeting by SAH-BCL9$_B$ with disengagement of the I-catenin-BCL9/B9L complexes. Given the documented toxicities associated with agents that target β-catenin and broadly disrupt its protein interactions, it was confirmed that FITC-SAH-BCL9$_B$ had no effect on β-catenin's homeostatic interaction with E-cadherin, consistent with the distinct, non-overlapping location of the BCL9/β-catenin binding site. The target-based selectivity of FITC-SAH-BCL9$_B$ was further documented by anti-FITC pulldown, which co-precipitates β-catenin but not other unrelated cellular proteins such as IxBα and actin.

Figure 2B:
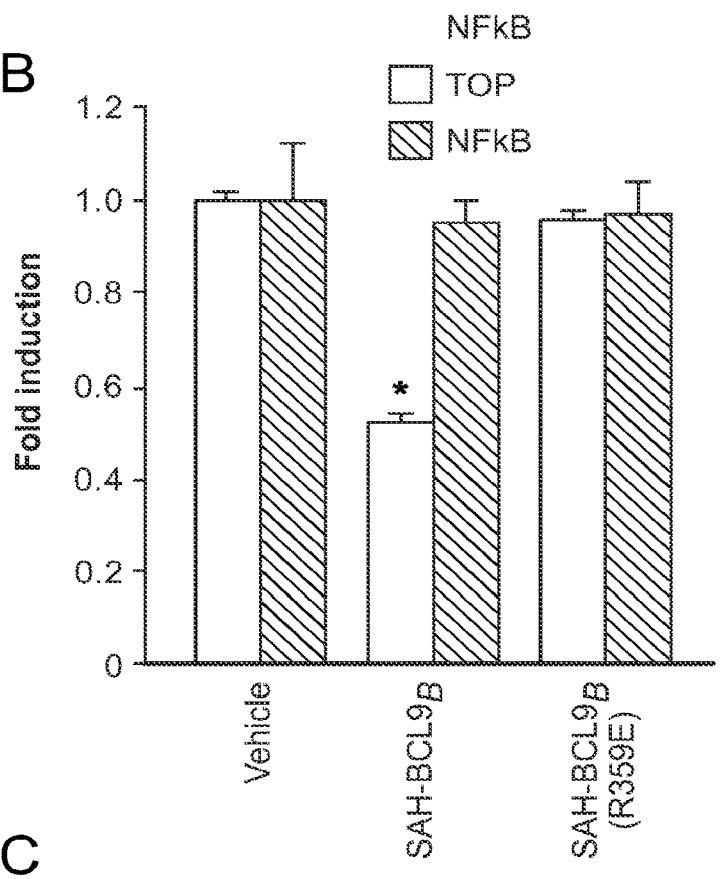
Figure 2C:
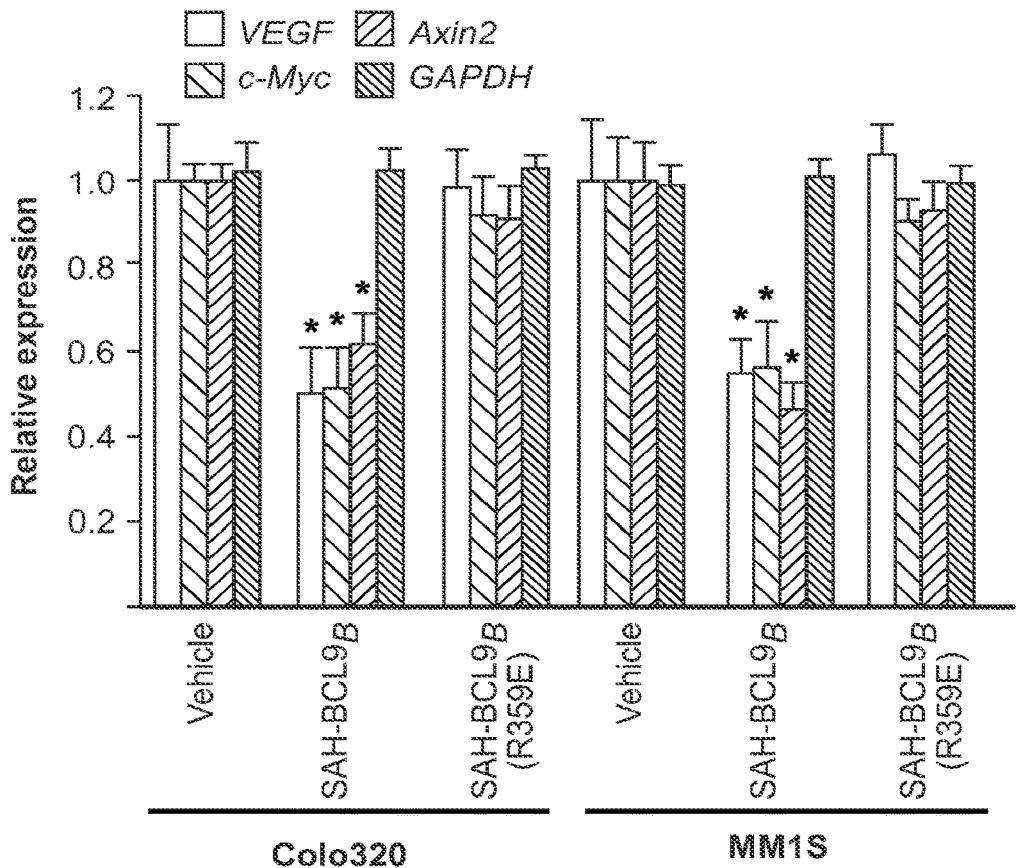

To examine the functional consequences of SAH-BCL9$_B$-mediated complex disruption, the effects of SAH-BCL9$_B$ and SAH-BCL9$_B$(R359E) in a Wnt-specific TCF reporter gene transcriptional assay were evaluated (Mani, M. et al., Cancer Res 69, 7577-86 (2009); Sustmann, C., et al. Mol Cell Biol 28, 3526-37 (2008)). Whereas SAH-BCL9$_B$ treatment reduced reporter activity by nearly 50%, vehicle and SAH-BCL9$_B$(R359E) showed no effect (FIG. 2B). Importantly, the specificity of the effect of SAH-BCL9 was documented by showing that the inhibitory effect of SAH-BCL9 was selectively abrogated by transfection with increasing amounts of pcDNA-BCL9, and that SAH-BCL9$_B$ had no effect on an NFκB reporter gene transcriptional assay (FIG. 2B). In a second Wnt-specific reporter assay that monitors dGFP, which is under the transcriptional control of TCF regulatory sequences, SAH-BCL9$_B$, but not vehicle or SAH-BCL9$_B$(R359E), dose-responsively blocked dGFP expression. Quantitative PCR (qPCR) analysis was employed to measure the effects of vehicle, SAH-BCL9$_B$, and SAH-BCL9$_B$(R359E) on the expression of β-catenin/BCL9 target genes, including VEGF. SAH-BCL9$_B$, but not vehicle or SAH-BCL9$_B$(R359E), significantly reduced mRNA levels of VEGF, c-Myc, and Axing, but not GAPDH, a non-Wnt pathway target gene (FIG. 2C).

Figure 3A:
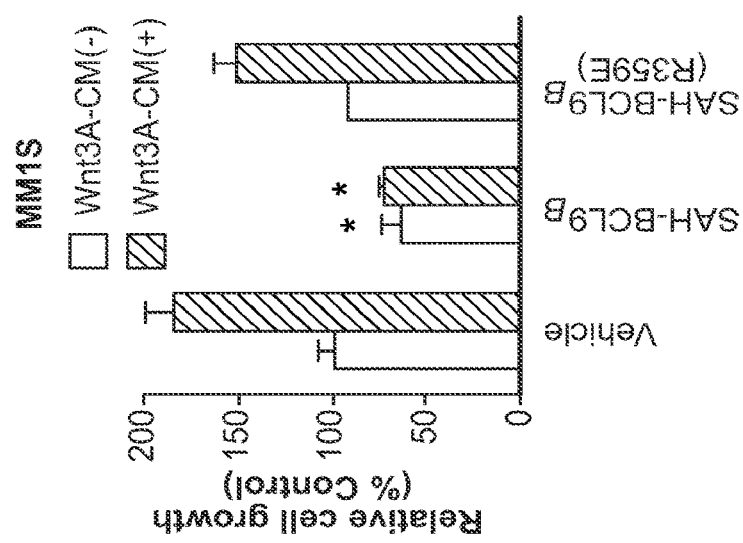
FIG. 3A-FIG. 3I show that SAH-BCL9$_B$ blocks cellular proliferation, angiogenesis, and migration.
Figure 3B:
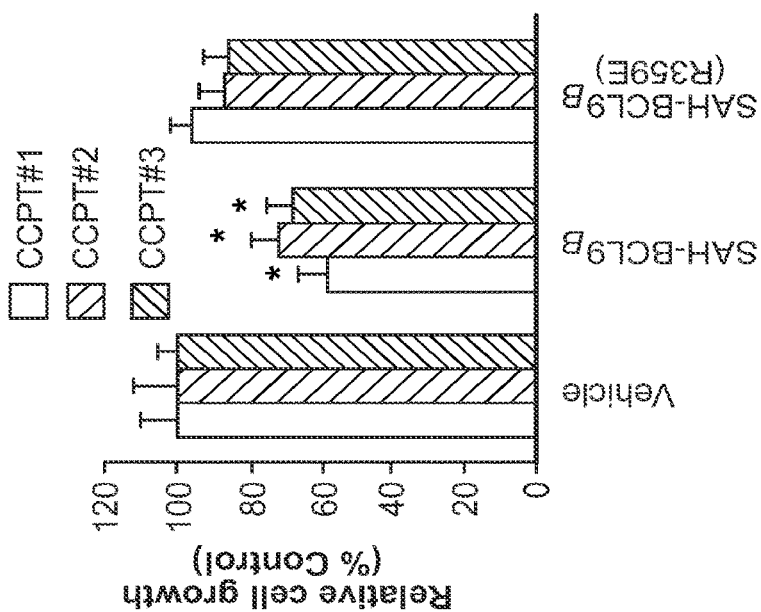
Figure 3C:
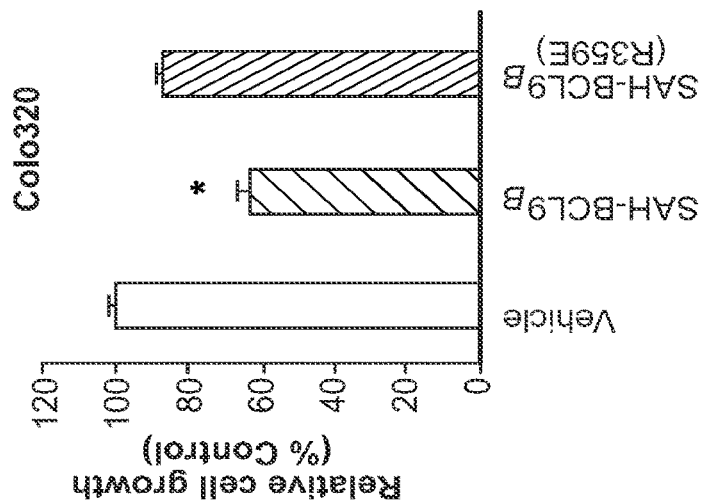
Figure 3E:
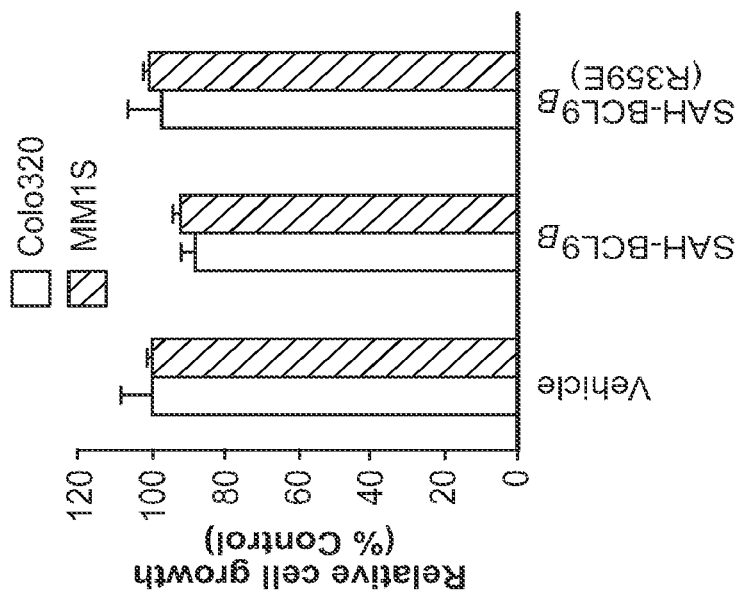
Figure 3D:
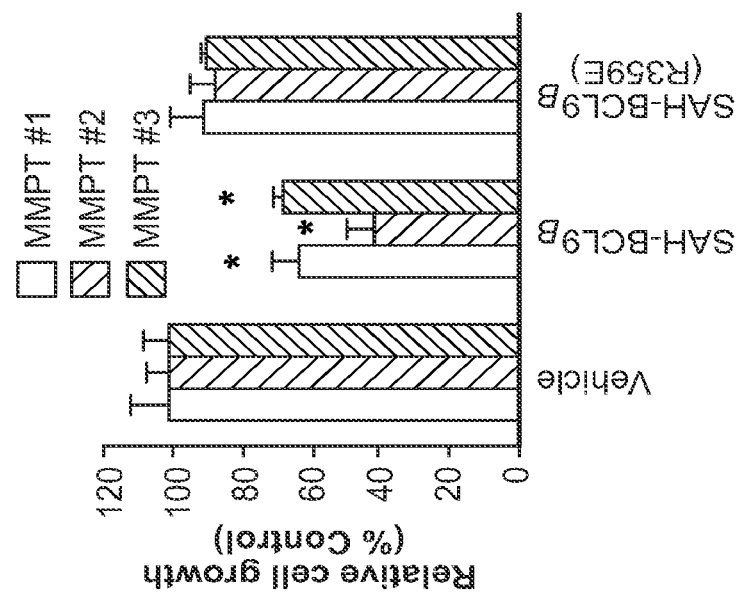
Figure 3F:
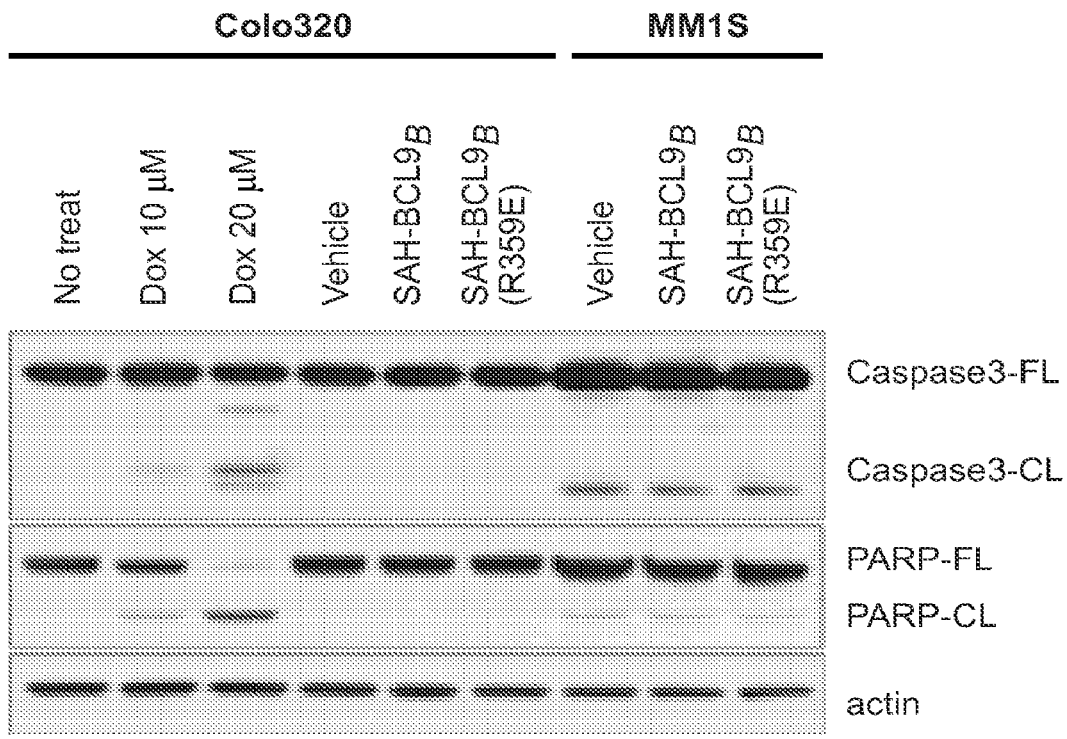
Figure 3G:
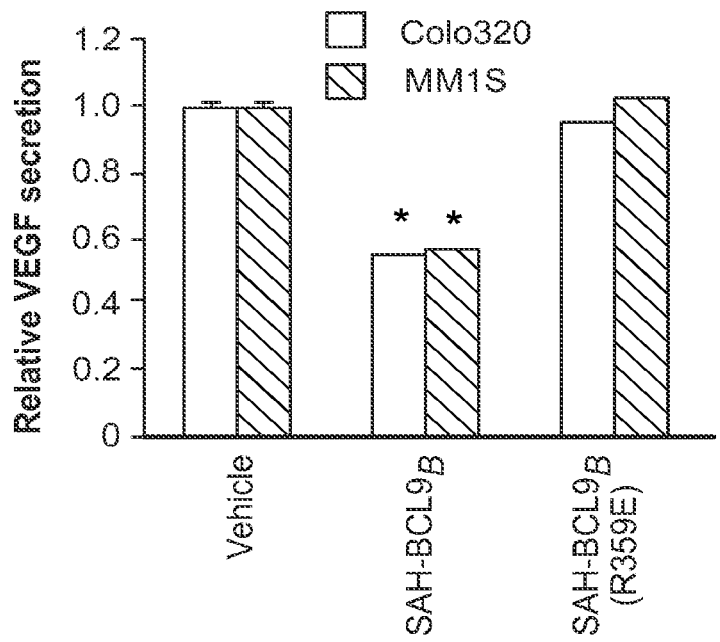
Figure 3I:
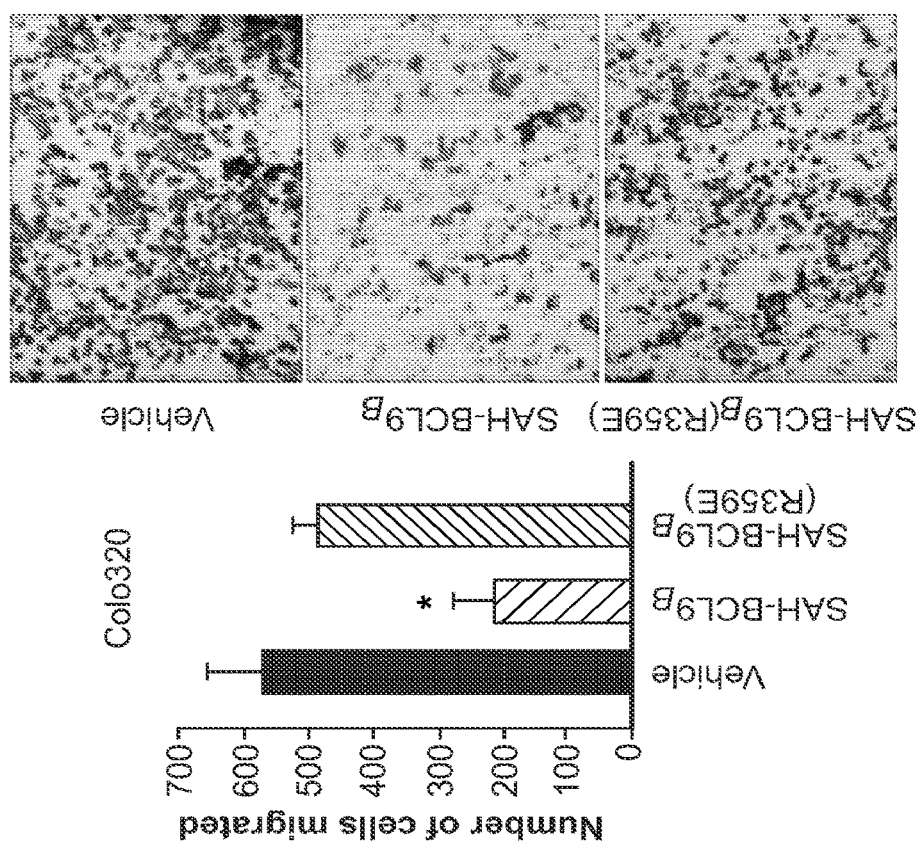
Figure 3H:
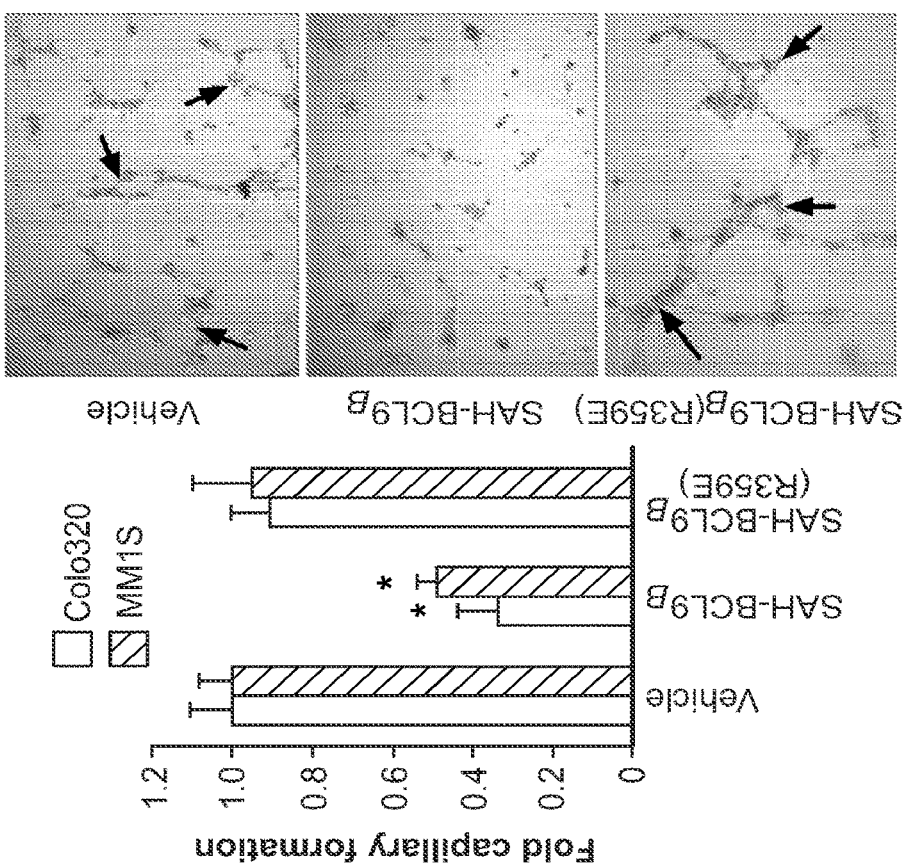

To examine the phenotypic consequences of pharmacologic disruption of the β-catenin/BCL9 complex, cellular proliferation, angiogenesis, and migration assays were conducted. A consistent pattern emerged whereby SAH-BCL9$_B$, but not vehicle or SAH-BCL9$_B$(R359E), reduced the proliferation of Colo320, MM1S, and primary CRC and MM cells (FIG. 3A-FIG. 3D). Of note, SAH-BCL9$_B$ treatment did not induce cell death, as evaluated by viability assays and western analysis for caspase-3 and PARP activation (FIG. 3E-FIG. 3F). To determine the effect of SAH-BCL9$_B$ on tumor cell-induced angiogenesis, Colo320 and MM1S cells were treated with vehicle and SAH-BCL9$_B$ peptides and then VEGF levels were quantitated in the media. Consistent with the qPCR analysis, only SAH-BCL9$_B$ reduced the level of secreted VEGF (FIG. 3G). In an in vitro angiogenesis assay, human umbilical vein endothelial cells (HUVEC) were cultured with supernatants from treated Colo320 or MM1S cells and then scored for the formation of capillary tube-like formations by microscopy. HUVEC cells exposed to the supernatant from SAH-BCL9$_B$-treated cells showed reduced capillary tube formation compared to the vehicle- and SAH-BCL9$_B$(R359E)-treated controls (FIG. 3H). SAH-BCL9$_B$ also decreased the adhesive and invasive potential of Colo320 cells, as reflected by a significant reduction in the capacity of SAH-BCL9$_B$-treated cells to pass thorough the extracellular matrix, as evaluated using Matrigel-coated invasion chambers (FIG. 3I). Taken together, these data demonstrate that SAH-BCL9$_B$ specifically disrupts a series of physiologic processes regulated by the BCL9/β-catenin transcriptional complex.

Figure 4B:
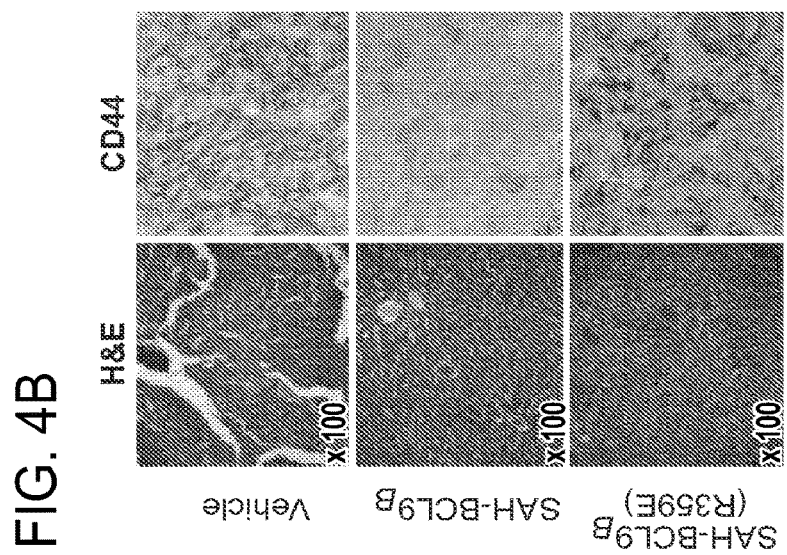
FIG. 4A-FIG. 4I show that SAH-BCL9$_B$ inhibits tumor growth, angiogenesis, and metastasis in vivo.
Figure 4A:
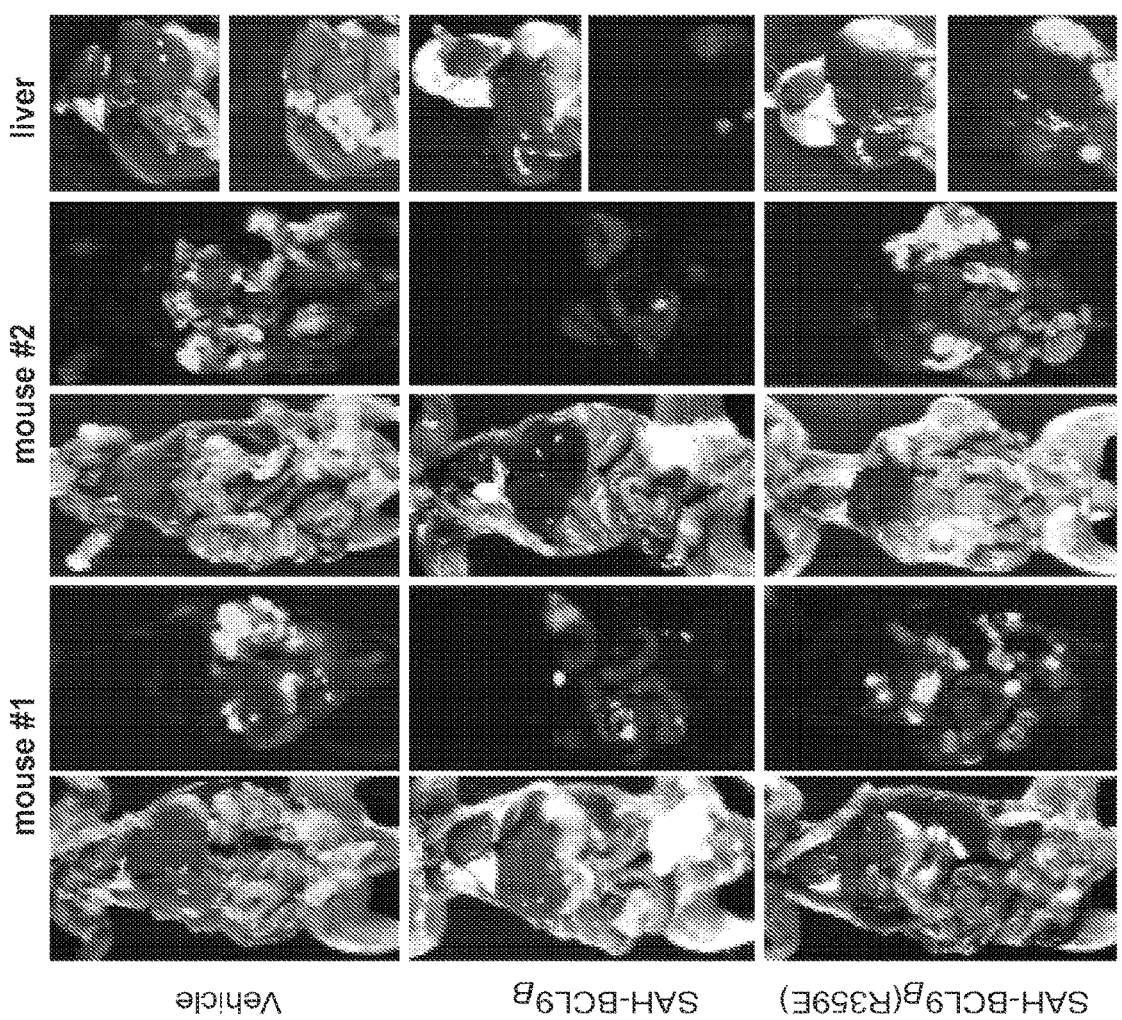
Figure 4C:
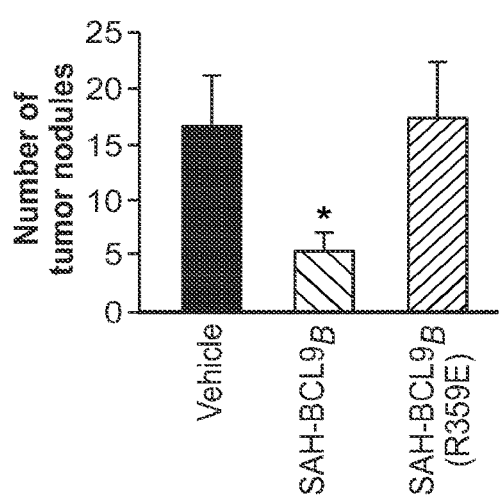
Figure 4D:
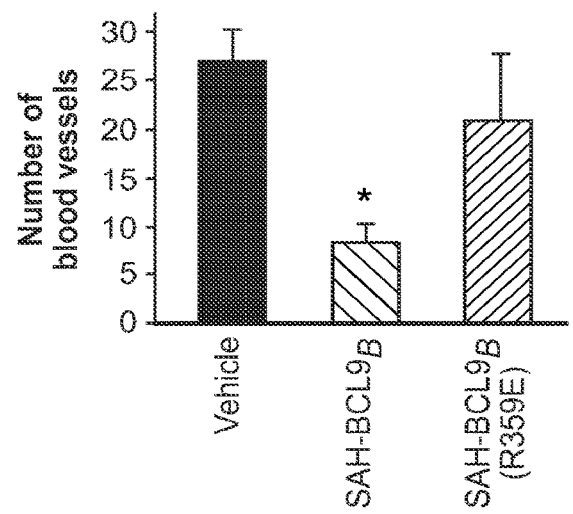
Figure 4E:
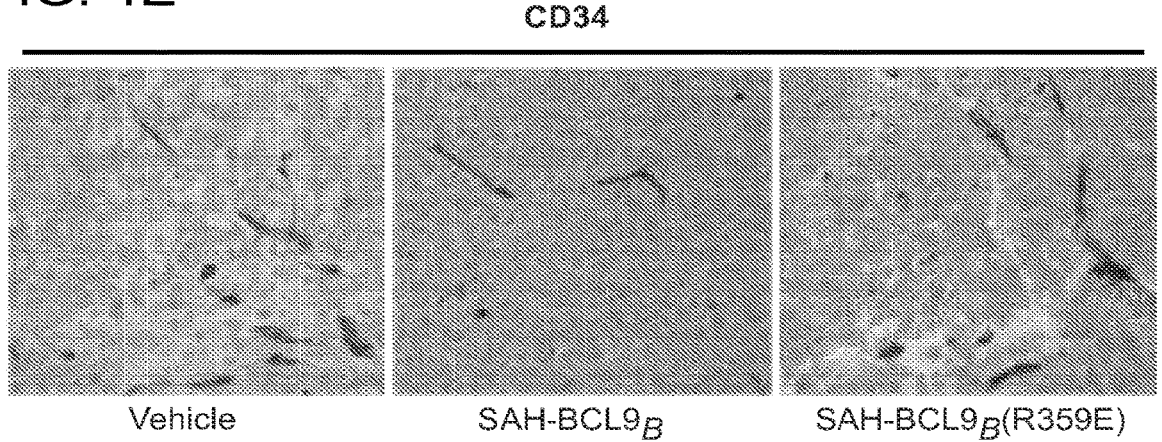

To explore the therapeutic potential of targeting the BCL9/β-catenin interaction, the capacity of SAH-BCL9$_B$ to suppress tumor growth was examined in vivo. GFP-expressing Colo320 cells ($1 \times 10^6$) were injected into the peritoneum of sublethally irradiated NOD/SCID mice. Two days after cellular injection, mouse cohorts (n=6) were treated with vehicle (2.5% DMSO in D5W), SAH-BCL9$_B$, or SAH-BCL9$_B$(R359E) peptides (20 mg/kg) for a total of 6 doses administered intraperitoneally every other day. On day 40 of the experiment, mice were sacrificed and evaluated for tumor burden and metastasis by whole body imaging and histologic examination of harvested GFP-positive tissues. Overall tissue fluorescence was markedly reduced in mice treated with SAH-BCL9$_B$ compared to vehicle and SAH-BCL9$_B$(R359E)-treated animals (FIG. 4A). These data were consistent with an overall reduction of metastatic tumor nodules observed in the livers of SAH-BCL9$_B$-treated mice (FIG. 4B-FIG. 4C). Interestingly, tumor tissue from SAH-BCL9$_B$-treated mice also showed decreased tumor cell CD44 immunoreactivity (FIG. 4B), a reduction in the number of intratumoral blood vessels (FIG. 4D), and less intense capillary CD34 immunoreactivity (FIG. 4E), suggesting that SAH-BCL9$_B$-mediated suppression of tumor growth and metastasis may derive at least in part from reduction of cell migration and angiogenesis. Importantly, no histologic changes in normal murine tissues were observed across the treatment groups upon necropsy.

Figure 4F:
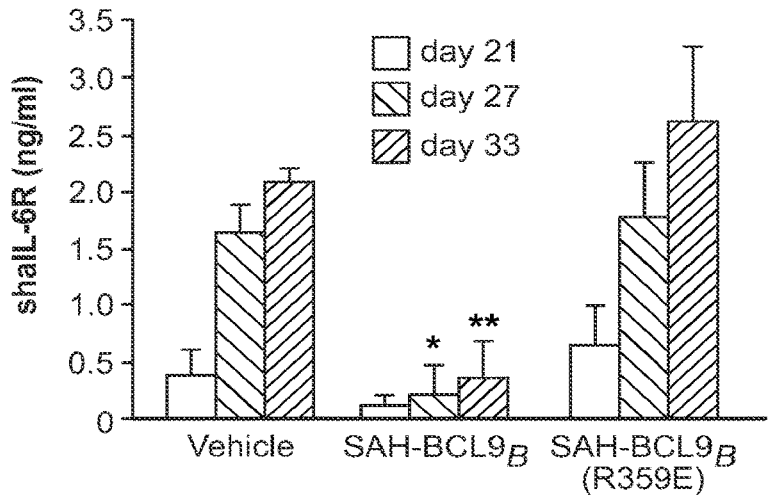
Figure 4G:
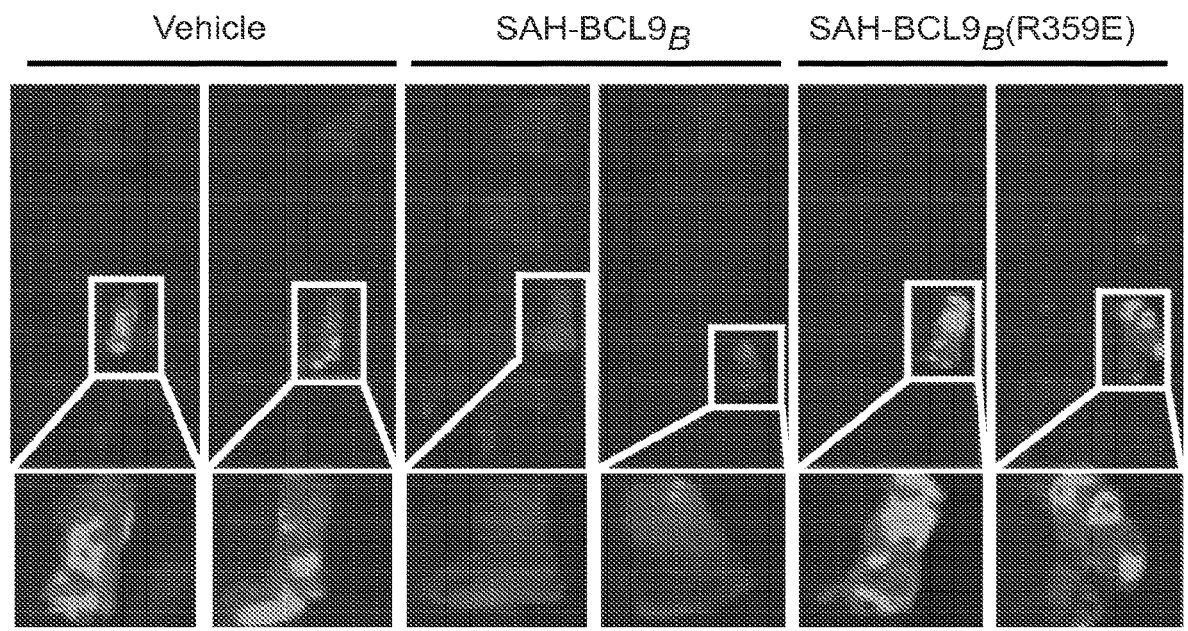
Figure 4H:
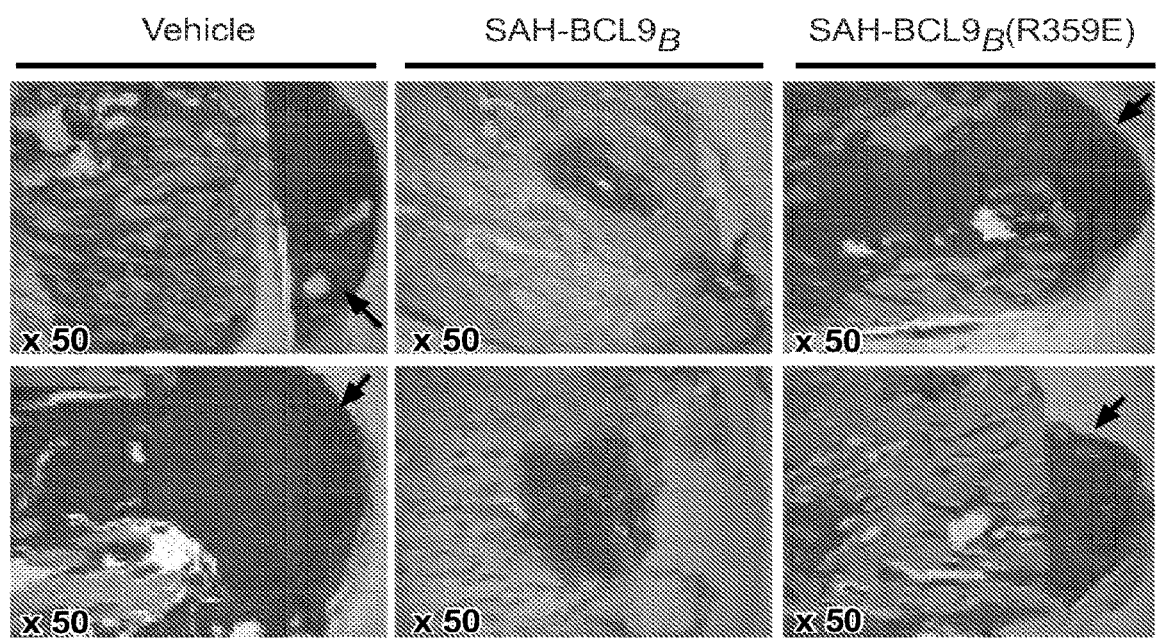
Figure 4I:
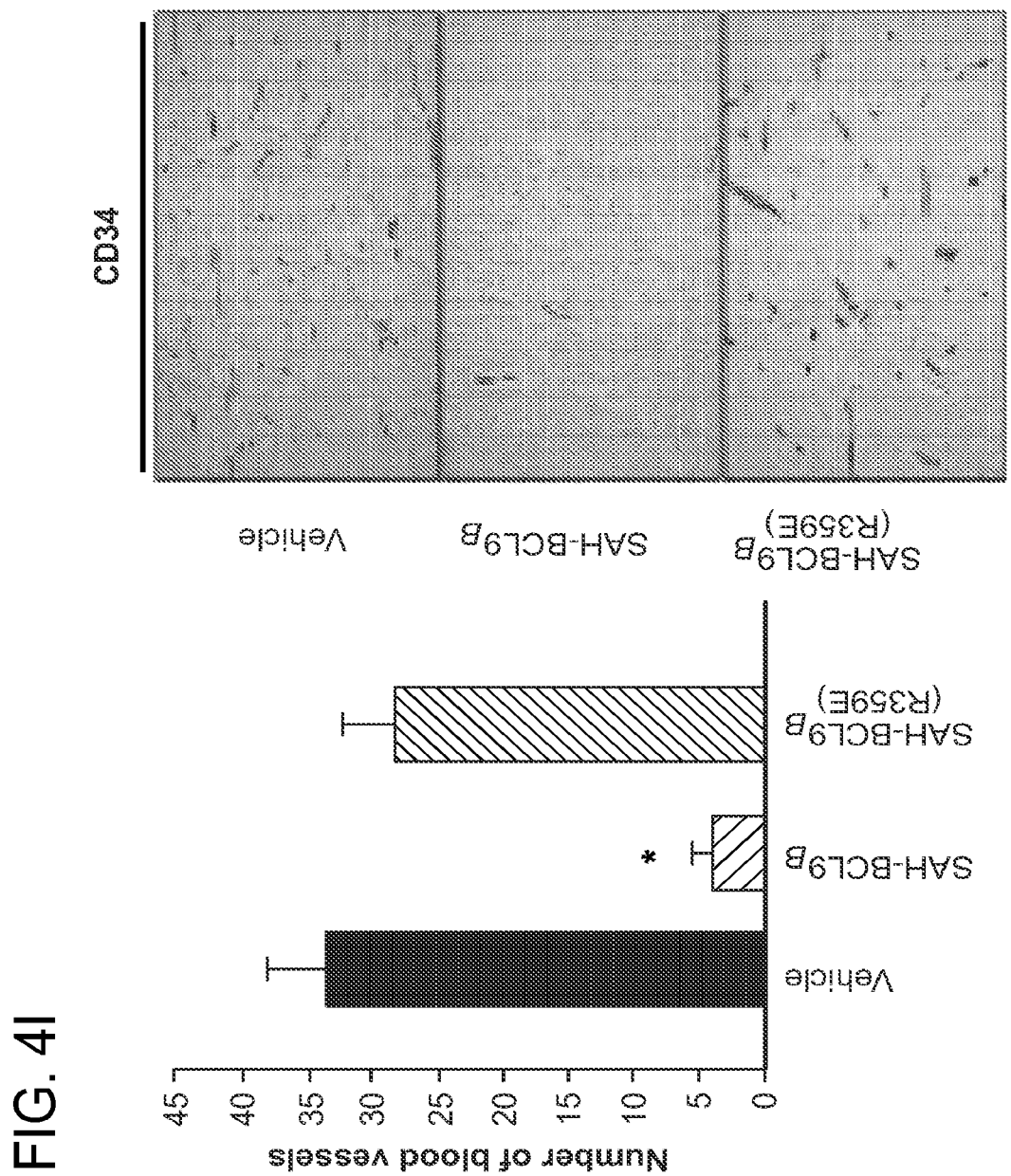
Figure 6A:
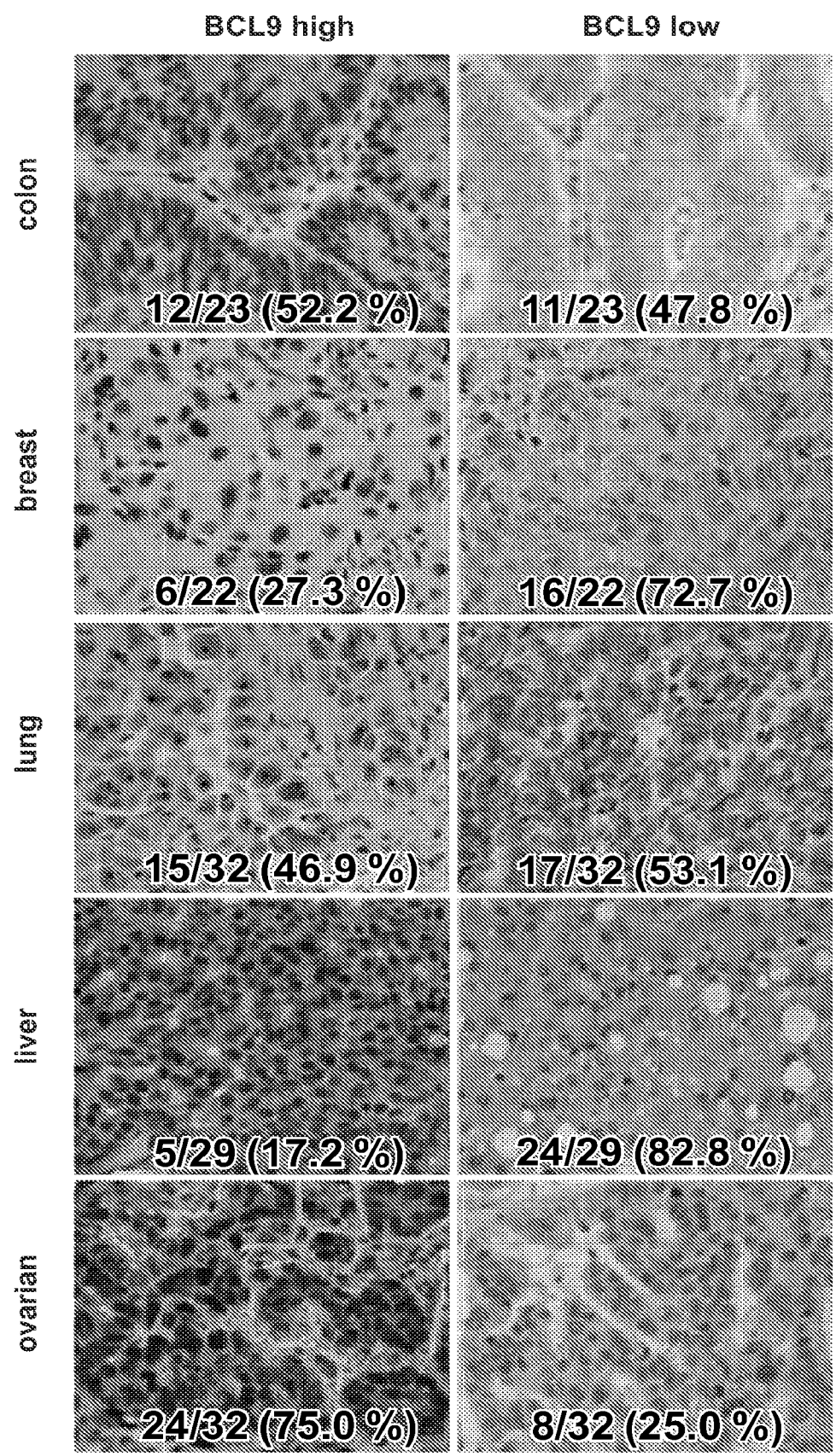
FIG. 6A-FIG. 6B show that BCL9 is overexpressed in a broad range of tumors.
Figure 6B:
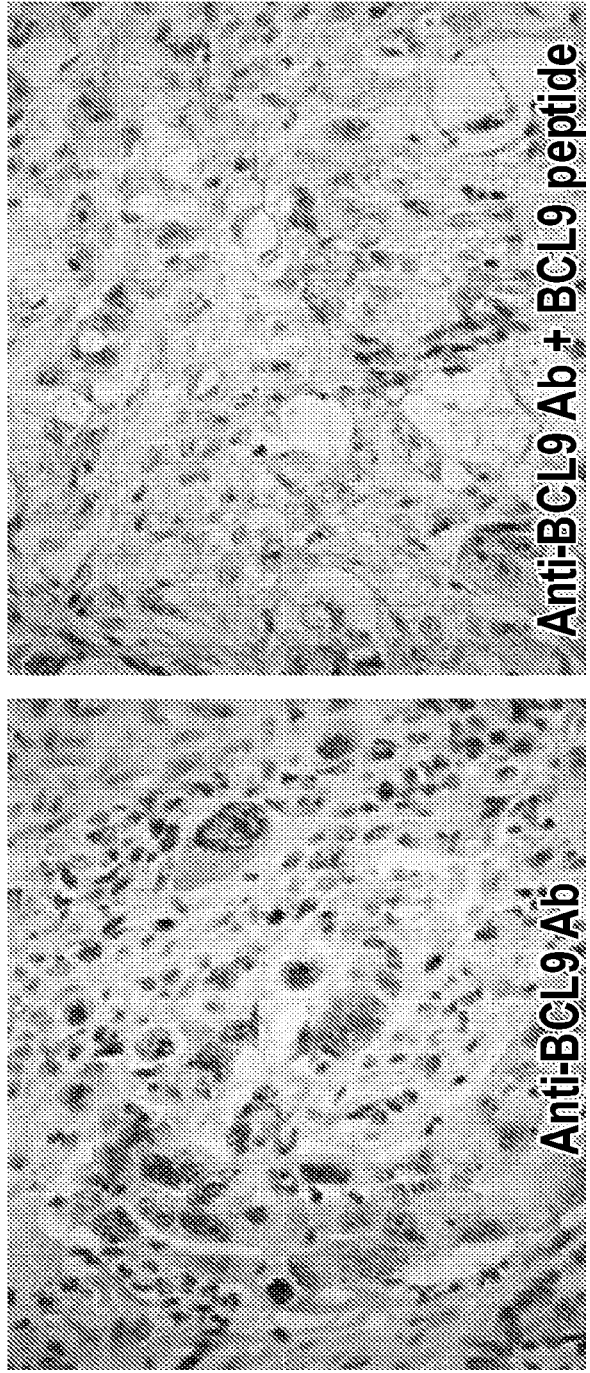

In a second in vivo model, the impact of SAH-BCL9$_B$ treatment on the growth of INA-6 MM cells within a human bone graft implanted in the flank of SCID-hu mice was examined (Tassone, P. et al. Blood 106, 713-6 (2005)). GFP-labeled INA-6 cells ($5 \times 10^6$), which express both BCL9 and β-catenin and are suppressed by SAH-BCL9$_B$ in vitro were injected into bone grafts four weeks after implantation. Two days later, cohorts of mice (n=5) were treated by local injection with vehicle (2.5% DMSO in D5W), SAH-BCL9$_B$, or SAH-BCL9$_B$(R359E) peptides (5 mg/kg) for a total of 10 doses administered every other day. To monitor tumor burden, the serum level of soluble human interleukin-6 receptor (shuIL-6R) was measured, which is first detectable 3-4 weeks after INA-6 tumor engraftment. Whereas mice treated with vehicle- and SAH-BCL9$_B$(R359E) showed a progressive increase in shuIL-6R levels reflective of tumor growth, SAH-BCL9$_B$-treated mice maintained low to undetectable levels throughout the evaluation period (FIG. 4F). Mice were sacrificed 33 days after INA-6 cell injection and evaluated for MM tumor burden by fluorescence imaging, histologic analysis, and anti-CD34 staining. Consistent with the measured levels of shuIL-6R, tumor burden within the bone chip was significantly reduced in SAH-BCL9$_B$-treated mice (FIG. 4G-FIG. 4H). Interestingly, the tumor cells present in SAH-BCL9$_B$-treated mice resided within the confines of the bone chip, whereas vehicle- and SAH-BCL9$_B$(R359E)-treated mice demonstrated invasion into the surrounding soft tissue (FIG. 4H, black arrows). Similar to the CRC model, local angiogenesis was suppressed in SAH-BCL9$_B$-treated SCID-hu mice, as monitored by anti-CD34 staining and blood vessel quantitation (FIG. 4I). Thus, in two distinct mouse models of Wnt-driven cancer, SAH-BCL9 effectively suppressed tumor growth, invasion, and angiogenesis in a sequence-specific manner.

The β-catenin transcriptional complex is a high priority pharmacologic target due to its pathologic role in a broad range of cancers. Because β-catenin participates in a variety of homeostatic functions and engages the majority of its interaction partners using the same binding surface (Barker, N. & Clevers, H. Nat Rev Drug Discov 5, 997-1014 (2006)), achieving anti-cancer activity and selectivity remains a pressing challenge. For example, PKF115-584, a small molecule identified by high-throughput screening for inhibitors of the β-catenin/TCF interaction, blocked Wnt-specific transcriptional activity and reduced the growth of colon cancer cells (Lepourcelet, M. et al. Cancer Cell 5, 91-102 (2004)), but induced severe bone marrow hypoplasia, anemia, and generalized wasting of treated mice (Sukhdeo, K. et al. Proc Natl Acad Sci USA 104, 7516-21 (2007)). Targeting the β-catenin-BCL9 interface as an alternate strategy is appealing because BCL9 (1) drives pathologic I-catenin transcriptional activity, (2) engages β-catenin at a unique binding site (Sampietro, J. et al. Mol Cell 24, 293-300 (2006)), and (3) is predominantly found in tumor tissue rather than the cells of origin (Mani, M. et al. Cancer Res 69, 7577-86 (2009)). Importantly, eliminating the BCL9/β-catenin interaction through genetic deletion of Bcl9 in a mouse model had no overt phenotypic consequences (Deka, J. et al. Cancer Res 70, 6619-28). Thus, hydrocarbon stapling was applied to structurally-stabilize BCL9's α-helical HD2 domain that directly engages β-catenin. In doing so, it was determined that SAH-BCL9$_B$ targets β-catenin in situ and selectively disrupts β-catenin-BCL9/B9L complexes. Pharmacologic blockade of these interactions coincided with inhibition of β-catenin-dependent transcriptional activity and target gene expression, and the suppression of tumor cell growth, angiogenesis, and metastasis without overt damage to normal tissues. Thus, these proof-of-principle experiments document that selective targeting of the β-catenin-BCL9 interface in cancer is a promising strategy for interrogating and combating oncogenic Wnt signaling.

The invention is based, at least in part, on the results provided herein, as well as PCT/US2009/000438 (WO 2009/108261; filed Jan. 23, 2009) demonstrating that stabilized alpha helical peptides have excellent structural, proteolytic, acid, and thermal stability. It has also been determined that stabilized alpha helical peptides are highly effective in interfering with Wnt/β-catenin signaling, indicating that the peptide can be used for the treatment of cancer. Further, the stabilized alpha-helical peptides have superior pharmacologic properties in vivo compared to their unmodified counterparts, reducing the frequency and quantity of stabilized alpha-helical peptide that needs to be administered as compared to a native peptide sequence, and ensuring that exposure is sustained.

From this point on, the term "stabilizing crosslink" or derivation thereof, shall refer to its namesake or other covalent, or ionic, crosslink such as, but not limited to, a disulfide, amide, ester, 1,2,3-triazole, or other bioconjugate or biocompatible crosslink. From this point on, the term "hydrocarbon-staple" or "hydrocarbon-crosslink" or derivation thereof, shall refer to its namesake or other hydrocarbon covalent, or ionic, bioconjugate or biocompatible crosslinks.

In the peptides provided herein, the alpha helix HD2 domain is stabilized with at least one molecular tether, e.g., hydrocarbon staple, but may include two, three or more hydrocarbon staples. The inclusion of multiple hydrocarbon staples is particularly suited for alpha helical peptides that are 16 or more amino acids in length. The inclusion of more than one (e.g., 2, 3, 4, 5, depending on the length of the peptide) hydrocarbon staples provides for exceptional proteolytic, structural, acid and thermal stability of the modified polypeptides, yielding bioactive peptides with strikingly enhanced pharmacologic properties in vivo (ref Bird et al, PNAS, 2010).

In the compounds provided herein, the HD2 domain is structurally constrained by one or more modifications of the native sequence. The alpha-helix of the HD2 domain can be stabilized using a molecular tether such as a hydrocarbon staple. Alternatively, or in addition, amino acid substitutions can be made in or adjacent to the region to include natural or non-natural amino acids to promote the desired structure of the peptide, to promote or maintain the desired angle between the two helices or to orient the helices relative to each other, or to improve the pharmacologic properties. In an embodiment, at least one of the helices of the HD2 domain includes a molecular tether such as a hydrocarbon staple to promote or maintain the helical nature of the domain. In another embodiment, both of the helices of the HD2 domain include a molecular tether(s) such as hydrocarbon staple(s) to promote or maintain the helical nature of the domain.

Hydrocarbon Stapling of Polypeptides

Preferably the alpha helix or HD2 domain is stabilized with at least one hydrocarbon staple. Hydrocarbon staples suitable for use with any of the modified polypeptides are described herein and in U.S. Publication Nos. 2005/0250680, 2010/0234563, 2007/0197772, 2006/0008848, 2006/0014675; U.S. Pat. Nos. 7,723,469, 7,192,713, and 7,084,244; International Publication Nos. WO 2009/108261) and WO 2010/148335; and Kawamoto, S. A. et al., J. Med. Chem. 55, 1137-1146 (2012); Mahon, A. B. and Arora, P. S., Chem. Commun. 48, 1416-1418 (2012); and Chapman, R. N. et al., J. Am. Chem. Soc. 126, 12252-3 (2004), which are incorporated by reference in their entirety. Hydrocarbon stapling allows a polypeptide, predisposed to have a helical secondary structure, to maintain its native helical conformation and increase its stability and efficacy. In one embodiment, the modified polypeptide has at least 10%, 20%, 30%, 35%, 40%, 45%, 50%, 60%, 70%, 80%, or 90% or more helicity in an aqueous solution as determined by circular dichroism. Assays for determining circular dichroism are known in the art and described herein.

The hydrocarbon stapled polypeptides include a tether (linkage) between two amino acids, in which the tether significantly enhances the helical secondary structure of the polypeptide. Generally, the tether extends across the length of one or two helical turns (i.e., 3, 4 or 7 amino acids). Accordingly, amino acids positioned at i and i+3; i and i+4; or i and i+7 are ideal candidates for chemical modification and cross-linking. Thus, any of the amino acid residues of the modified polypeptides of the invention may be tethered (e.g., cross-linked) in conformity with the above. Suitable tethers are described herein and in U.S. Publication Nos. 2005/0250680, 2010/0234563, 2007/0197772, 2006/0008848, 2006/0014675; U.S. Pat. Nos. 7,723,469, 7,192,713, and 7,084,244; International Publication Nos. WO 2009/108261) and WO 2010/148335; and Kawamoto, S. A. et al., J. Med. Chem. 55, 1137-1146 (2012); Mahon, A. B. and Arora, P. S., Chem. Commun. 48, 1416-1418 (2012); and Chapman, R. N. et al., J. Am. Chem. Soc. 126, 12252-3 (2004). It is understood that tethers such as hydrocarbon staples can be positioned at other intervals to promote helical variants (e.g., with different pitches, angles, or residues and fractions thereof per turn) or structures other than helices.

In a further embodiment, the hydrocarbon staple(s) is positioned so as to link a first amino acid (i) and a second amino acid (i+3) which is 3 amino acids downstream of the first amino acid. In another embodiment, the hydrocarbon staple links a first amino acid (i) and a second amino acid (i+4) which is 4 amino acids downstream of the first amino acid. In yet another embodiment, the hydrocarbon staple links a first amino acid (i) and a second amino acid (i+7) which is 7 amino acids downstream of the first amino acid.

The modified polypeptides of the invention will generally include the structure of Formula (I), (II) or (III) provided below.

Any of the modified polypeptides described herein can be present in a composition (e.g., pharmaceutical composition) or kit. In some embodiments of the invention, the composition or kit comprises two or more modified polypeptides.

SAH-BCL9 Peptides

The modified polypeptides of the invention include the HD-2 peptides amino acids 352 to 374 of the following

```
SEQ ID NO: 1: BCL9 HD2 domain:
LSQEQLEHRERSLQTLRDIQRMLF

SEQ ID NO: 2: BCL9 HD2 domain M372B:
LSQEQLEHRERSLQTLRDIQRBLF
```

```
-continued
SEQ ID NO: 3: SAH-BCL9_A:
LSQEQLEHRERSLQTLRXIQRXLF

SEQ ID NO: 4: SAH-BCL9_B:
LSQEQLEHRERSLXTLRXIQRBLF

SEQ ID NO: 5: SAH-BCL9_C:
LSQEQLEHREXSLQXLRDIQRBLF

SEQ ID NO: 6: SAH-BCL9_B(H358D):
LSQEQLEDRERSLXTLRXIQRBLF

SEQ ID NO: 7: SAH-BCL9_B(R359E):
LSQEQLEHEERSLXTLRXIQRBLF
```

Peptides corresponding to analogs of the full-length and truncated HD2 domain or BCL9 peptides, described, above, may be contemplated by the invention. The term "HD2 domain analogs", as used herein, refers to a peptide that is recognized or identified as having a repeat-analog domain or BCL9 domain. Methods for repeat-analog polypeptides are known in the art, for example, bioinformatics programs based on pairwise residue correlations (e.g., on the world wide web at: ch.embnet.org/software/COILS_form.html), which have the ability to recognize coils from protein sequences and model their structures (See Lupas, A., et al. Science 1991. 252: 1162-1164, which is incorporated herein by reference). Further, such modified peptides exhibit anti-cancer activity. Methods for identifying BCL9 HD2 and other BCL9 homologues are known in the art and can be performed using the criteria set forth herein.

Mutations, Truncations, and Extensions of HD2 Domain and BCL9 Peptides

The amino acid substitutions may be of a conserved or non-conserved nature. Conserved amino acid substitutions consist of replacing one or more amino acids of the HD2 peptide sequence with amino acids of similar charge, size, and/or hydrophobicity characteristics. Non-conserved substitutions consist of replacing one or more amino acids of the HD2 domain sequence with amino acids possessing dissimilar charge, size, and/or hydrophobicity characteristics. Substitutions can include the use of conserved or non-conserved non-natural amino acids.

Amino acid insertions may consist of single amino acid residues or stretches of residues. The insertions may be made at the carboxy or amino terminal end of the full-length or truncated HD2 domain or BCL9 peptide, as well as at a position internal to the peptide. Such insertions will generally range from 2 to 15 amino acids in length. It is contemplated that insertions made at either the carboxy or amino terminus of the peptide of interest may be of a broader size range, with about 2 to about 50 amino acids being preferred. One or more such insertions may be introduced into full-length or truncated HD2 domain or BCL9 peptide, as long as such insertions result in modified peptides which may still exhibit anti-cancer activity.

Deletions of full-length or truncated HD2 domain or BCL9 peptide are also within the scope of the invention. Such deletions consist of the removal of one or more amino acids from the HD2 domain or BCL9 peptide; or HD2 domain or BCL9 peptide-like peptide sequence, with the lower limit length of the resulting peptide sequence being 4, 5, or 6 amino acids. Such deletions may involve a single contiguous or greater than one discrete portion of the peptide sequences. One or more such deletions may be introduced into full-length or truncated HD2 domain or BCL9 peptide, as long as such deletions result in peptides which may still exhibit anti-cancer activity.

Additionally, one skilled in the art would recognize that the interaction between the hydrocarbon-stapled peptide and its target protein form a complex in which, on the peptide there can be defined, an interacting face and a non-interacting face. Mutations along the non-interacting face can be made facilely, whilst mutations on the interacting face are not tolerated, such that the residues on the interacting face are the main component of the complex and as such should be conserved and maintained in designed hydrocarbon-stapled peptides. As such, greater than 10%, 20%, 30%, 40%, 50%, 60%, 70%, 80%, or 90% of the residues on the interacting face of BCL9 HD2 domain in the β-catenin/BCL9 complex should unchanged or changed to a structurally or chemically similar amino acid residue.

Stabilization of HD2 Domain and BCL9 Peptides

The modified polypeptides of the present invention are structurally constrained (e.g., stabilized, stapled) helical and/or include one or more amino acid sequence modifications as compared to the native (i.e., wild type or otherwise naturally occurring) sequence to incorporate natural and/or non-natural amino acids to limit the structural flexibility of the peptide as compared to the native sequence, which loses bioactive shape when taken out of physiologic context. Preferably, the polypeptides include at least one molecular tether such as a hydrocarbon staple. Hydrocarbon stapling is described in U.S. Publication Nos. 2005/0250680, 2010/0234563, 2007/0197772, 2006/0008848, 2006/0014675; U.S. Pat. Nos. 7,723,469, 7,192,713, and 7,084,244; International Publication Nos. WO 2009/108261) and WO 2010/148335; and Kawamoto, S. A. et al., J. Med. Chem. 55, 1137-1146 (2012); Mahon, A. B. and Arora, P. S., Chem. Commun. 48, 1416-1418 (2012); and Chapman, R. N. et al., J. Am. Chem. Soc. 126, 12252-3 (2004), which are incorporated herein by reference in their entirety.

The peptide α-helix participates in critically important protein interactions by presenting specific amino acid residues in an ordered and precise arrangement over a relatively large contact surface area (Chittenden, T., et al., *Embo Journal*, 1995. 14(22): p. 5589-5596; Kussie, P. H., et al. Science, 1996. 274(5289): p. 948-953; Ellenberger, T. E., et al., *Cell*, 1992. 71(7): p. 1223-1237). Alpha-helical domains and other protein structural features are frequently stabilized by scaffold sequences in the remainder of the protein, which facilitate the formation and/or maintenance of a helical structure, e.g., an α-helical structure. When taken out of context, α-helical peptide motifs can unfold, leading to loss of biological activity. Critical challenges in developing α-helical peptides include promoting and/or maintaining their natural α-helical structure and preparing peptides that can resist proteolytic, acid and thermal degradation, and thereby remain intact in vivo.

Hydrocarbon stapling refers to a process for stably cross-linking a polypeptide via at least two substituted amino acids (or a non-native linkage, e.g., carbon-carbon, from two natural amino acids) that helps to conformationally bestow the native secondary structure of that polypeptide. Hydrocarbon stapling promotes and maintains an alpha-helical secondary structure in peptides that thermodynamically favor an alpha-helical structure. This secondary structure increases resistance of the polypeptide to proteolytic cleavage and heat, and also may increase hydrophobicity. Accordingly, the hydrocarbon stapled (structurally constrained, e.g., crosslinked) polypeptides described herein have improved biological activity relative to a corresponding non-hydrocarbon stapled (not structurally constrained) polypeptide. The cross-linked polypeptides described herein can be used therapeutically, e.g., to treat cancer.

The hydrocarbon stapled polypeptides include a tether (linkage) between two amino acids, which tether significantly enhances the helical secondary structure of the polypeptide. Generally, the tether extends across the length of one or two helical turns (i.e., about 3-3.6 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful as are cross-links between X2 and X5, or between X2 and X6, or between X2 and X9, etc. The use of multiple cross-links (e.g., 2, 3, 4 or more) has also been achieved, compounding the benefits of individual stapled adducts (e.g., improved helicity and activity; improved helicity and thermal stability; improved helicity and acid stability; improved helicity and pharmacologic properties). The use of "stitched" cross-links has also been achieved whereby double linkages are made from a common origin (e.g., X1, X5, and X9, where X5 is the anchor point for both staples). Thus, the invention encompasses the incorporation of one or more crosslinks within the polypeptide sequence to either further stabilize the sequence or facilitate the structural stabilization, proteolytic resistance, thermal stability, acid stability, pharmacologic properties, and biological activity enhancement of longer polypeptide stretches.

In some embodiments of the invention, the tethers, e.g., hydrocarbon staples are used to stabilize structures other than helices. In such cases, the ends of the tethers can be placed at intervals other than at i, i+3, i+4, and i+7.

In one embodiment, the modified polypeptides of the invention have the formula (I),

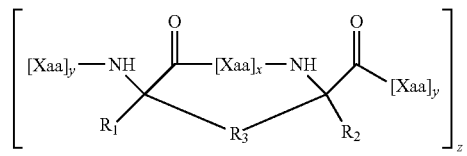

wherein;
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;
$R_3$ is alkyl, alkenyl, alkynyl; $[R_4—K—R_4]_n$; each of which is substituted with 0-6 $R_5$;
$R_4$ is alkyl, alkenyl, or alkynyl;
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;
K is O, S, SO, $SO_2$, CO, $CO_2$, $CONR_6$, or

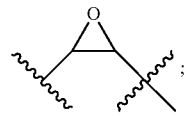 [SMILES: *C1OC1*]

$R_6$ is H, alkyl, or a therapeutic agent;
n is an integer from 1-4;
x is an integer from 2-10;
each y is independently an integer from 0-100;
z is an integer from 1-10 (e.g., 1, 2, 3, 4, 5, 6, 7, 8, 9, 10); and
each Xaa is independently an amino acid.

The modified polypeptides may include an amino acid sequence which forms an alpha-helix and is 30% or more identical to, an amino acid sequence of SEQ ID NO: 1-7; wherein X is any amino acid and further identifies the amino acid residues which are linked by a hydrocarbon staple, and B is norleucine.

The tether can include an alkyl, alkenyl, or alkynyl moiety (e.g., $C_5$, $C_8$ or $C_{11}$ alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl).

In some instances, x is 2, 3, or 6.

In some instances, each y is independently an integer between 3 and 15.

In some instances each y is independently an integer between 1 and 15.

In some instances, $R_1$ and $R_2$ are each independently H or $C_1$-$C_6$ alkyl.

In some instances, $R_1$ and $R_2$ are each independently $C_1$-$C_3$ alkyl.

In some instances, at least one of $R_1$ and $R_2$ are methyl. For example $R_1$ and $R_2$ are both methyl.

In some instances $R_3$ is alkyl (e.g., $C_8$ alkyl) and x is 3.

In some instances, $R_3$ is $C_{11}$ alkyl and x is 6.

In some instances, $R_3$ is alkenyl (e.g., $C_8$ alkenyl) and x is 3.

In some instances x is 6 and $R_3$ is $C_{11}$ alkenyl.

In some instances, $R_3$ is a straight chain alkyl, alkenyl, or alkynyl.

In some instances $R_3$ is —$CH_2$—$CH_2$—$CH_2$—CH=CH—$CH_2$—$CH_2$—$CH_2$—.

In certain embodiments the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as

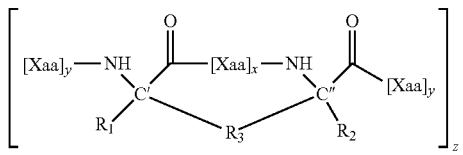

the C' and C" disubstituted stereocenters can both be in the R configuration or they can both be in the S configuration, for example when X is 3. When x is 6, the C' disubstituted stereocenter is in the R configuration and the C" disubstituted stereocenter is in the S configuration. The $R_3$ double bond may be in the E or Z stereochemical configuration.

In some instances $R_3$ is $[R_4—K—R_4]_n$; and $R_4$ is a straight chain alkyl, alkenyl, or alkynyl.

In some embodiments the modified polypeptide comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more amino acids of a repeat or repeat like domain, e.g., a BCL9 HD2 domain. Each $[Xaa]_y$ is a peptide that can independently comprise at least 5, 6, 7, 8, 9, 10, 11, 12, 13, 14, 15, 16, 17, 18, 19, 20, 25 or more amino acids of a repeat or repeat like domain, e.g., a HD2 domain. $[Xaa]_x$ is a peptide that can comprise 3 or 6 amino acids of a repeat or repeat like domain.

The modified polypeptide can comprise 3, 4, 5, 6, 7, 8, 9, 10, 11, 12, 13, 14, 15, 16, 17, 18, 19, 20, 25, 30, 35, 40, 45, 50 or more amino acids of a repeat or repeat like domain, e.g., a HD2 domain, e.g., a polypeptide having the amino acid sequence of SEQ ID NO: 1-7, wherein two amino acids that are separated by two, three, or six amino acids are replaced by amino acid substitutes that are linked via $R_3$. Thus, at least two amino acids can be replaced by tethered amino acids or tethered amino acid substitutes. Thus, where formula (I) is depicted as

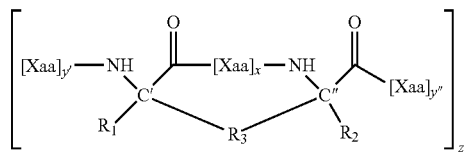

$[Xaa]_{y'}$ and $[Xaa]_{y''}$ can each comprise polypeptide sequences from the same or different heptad repeat or heptad repeat like domains.

The invention features cross-linked polypeptides comprising 10 (11, 12, 13, 14, 15, 16, 17, 18, 19, 20, 21, 22, 23, 24, 25, 30, 35, 40, 45, 50 or more) amino acids of a repeat or repeat like domain, e.g., a HD2 domain e.g., a polypeptide having the amino acid sequence of SEQ ID NO: 1-7 wherein the alpha carbons of two amino acids that are separated by two, three, or six amino acids are linked via $R_3$, one of the two alpha carbons is substituted by $R_1$ and the other is substituted by $R_2$ and each is linked via peptide bonds to additional amino acids.

In another embodiment, the modified polypeptides of the invention have the formula (II),

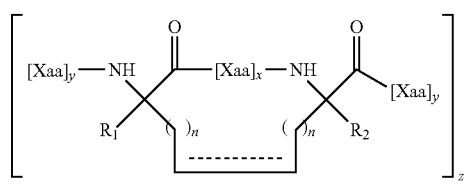

wherein
each $R_1$ and $R_2$ are independently H, alkyl, alkenyl, alkynyl, arylalkyl, cycloalkylalkyl; heteroarylalkyl; or heterocyclylalkyl;
each n is independently an integer from 1-15;
x is 2, 3, or 6
each y is independently an integer from 0-100;
z is an integer from 1-10 (e.g., 1, 2, 3, 4, 5, 6, 7, 8, 9, 10);
each Xaa is independently an amino acid.

In still another embodiment, the modified polypeptides of the invention have the formula (III),

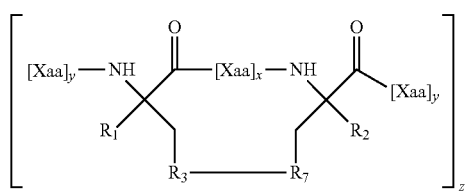

wherein;
each $R_1$ and $R_2$ are independently H, alkyl, alkenyl, alkynyl, arylalkyl, cycloalkylalkyl, heteroarylalkyl, or heterocyclylalkyl;
$R_3$ is alkyl, alkenyl, alkynyl; $[R_4—K—R_4]_n$ or a naturally occurring amino acid side chain; each of which is substituted with 0-6 $R_5$;

$R_4$ is alkyl, alkenyl, or alkynyl;
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;
K is O, S, SO, $SO_2$, CO, $CO_2$, $CONR_6$, or

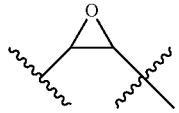 [SMILES: *C1OC1*]

$R_6$ is H, alkyl, or a therapeutic agent;
$R_7$ is alkyl, alkenyl, alkynyl; $[R_4—K—R_4]_n$ or an naturally occurring amino acid side chain; each of which is substituted with 0-6 $R_5$;
n is an integer from 1-4;
x is an integer from 2-10;
each y is independently an integer from 0-100;
z is an integer from 1-10 (e.g., 1, 2, 3, 4, 5, 6, 7, 8, 9, 10); and
each Xaa is independently an amino acid.

Also contemplated by the invention are the stitched peptides which are disclosed at least at PCT/US2008/058575 (WO 2008/121767), the contents of which are incorporated herein by reference.

The modified polypeptides may include an amino acid sequence that forms an alpha-helix and is 20% or more identical to, or contain at least 7 amino acids from an amino acid sequence, or at least two amino acids from a face of a helix formed by a peptide having the sequence of SEQ ID NO: 1-7; wherein X is any amino acid and further identifies the amino acid residues which are linked by a hydrocarbon staple, and B is norleucine. In certain embodiments, modified polypeptides may include an amino acid sequence that forms an alpha-helix and is 30% or more identical to a peptide having the sequence of SEQ ID NO: 1-7. In certain embodiments, the amino acid sequence in the alpha-helix is 40%, 50%, 60%, 70%, 80%, 90%, or 95% or greater identical to a peptide having the sequence of SEQ ID NO: 1-7.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary structure, whereas, in some instances, it is desirable to provide less constraint on the secondary structure, and thus a longer tether may be desired. It is further understood that the insertion of the tether at a site or in an amino acid sequence when the amino acid sequence has no tendency to form a helix will not result in helix formation.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids to promote and/or maintain the structures other than alpha helices.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The specific method of synthesis of the peptides is not a limitation of the invention.

Synthesis of Peptides

The peptides of this invention can be made by chemical synthesis methods, which are well known to the skilled artisan and described herein. See, for example, Fields et al., Chapter 3 in *Synthetic Peptides: A User's Guide*, ed. Grant, W. H. Freeman & Co., New York, N.Y., 1992, p. 77; and Bird, G. H., et al., Methods Enzymol 446, 369-86 (2008). Hence, peptides can be synthesized using the automated Merrifield techniques of solid phase synthesis with the alpha-$NH_2$ protected by either t-Boc or Fmoc chemistry using side chain protected amino acids on, for example, an Applied Biosystems Peptide Synthesizer Model 430A or 431 or the AAPPTEC multichannel synthesizer APEX 396.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides can also be made by conjoining individual synthetic peptides using native chemical ligation. Alternatively, longer synthetic peptides can be synthesized by well known recombinant DNA techniques. Such techniques are provided in well-known standard manuals with detailed protocols. To construct a coding sequence encoding a peptide of this invention, the amino acid sequence is reverse translated to obtain a nucleic acid sequence encoding the amino acid sequence, preferably with codons that are optimum for the organism in which the gene is to be expressed. Next, a coding sequence is made, typically by synthesizing oligonucleotides which encode the peptide and any regulatory elements, if necessary. The coding sequence is inserted in a suitable cloning vector and transfected into a host cell. Furthermore, the host cell is engineered so as to be able to incorporate the non-natural amino acids for the hydrocarbon staple. The peptide is then expressed under suitable conditions appropriate for the selected expression system and host. See Liu et al. *Proc. Nat. Acad. Sci* (USA), 94:10092-10097 (1997). The peptide is purified and characterized by standard methods.

The peptides can be made in a high-throughput, combinatorial fashion, e.g., using a high-throughput multichannel combinatorial synthesizer such as that available from Advanced Chemtech/APPTTEC, Thuramed or CEM.

Definitions

An "agent" is understood herein to include a therapeutically active compound or a potentially therapeutic active compound. An agent can be a previously known or unknown compound. As used herein, an agent is typically a non-cell based compound, however, an agent can include a biological therapeutic agent, e.g., peptide or nucleic acid therapeutic, cytokine, etc.

As used herein "amelioration" or "treatment" is understood as meaning to lessen or decrease at least one sign, symptom, indication, or effect of a specific disease or condition. Amelioration and treatment can require the administration of more than one dose of an agent, either alone or in conjunction with other therapeutic agents and interventions. Amelioration or treatment do not require that the disease or condition be cured.

The term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and non-naturally occurring amino acids including beta-amino acids and $\alpha,\alpha$ disubstituted amino acids, prepared by organic synthesis or other metabolic routes and that can be applied for specialized uses such as increasing chemical diversity, functionality, binding capacity, structural mimesis, and stability.

The term "amino acid side chain" or "amino acid R group" refers to a moiety attached to the $\alpha$-carbon in an amino acid. For example, the amino acid side chain or R group for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an alpha, alpha di-substituted amino acid, a beta-amino acid).

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism or a substance produced by a reporter construct (e.g., β-galactosidase or luciferase). Depending on the method used for detection the amount and measurement of the change can vary. Determination of statistical significance is within the ability of those skilled in the art.

"Co-administration" as used herein is understood as administration of one or more agents to a subject such that the agents are present and active in the subject at the same time. Co-administration does not require a preparation of an admixture of the agents or simultaneous administration of the agents.

A "conservative amino acid substitution" is one in which the amino acid residue is replaced with an amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Other conserved amino acid substitutions can also occur across amino acid side chain families, such as when substituting an asparagine for aspartic acid in order to modify the charge of a peptide. Thus, a predicted amino acid residue in a HD2 domain peptide, for example, is preferably replaced with another amino acid residue from the same side chain family or homologues across families (e.g., asparagine for aspartic acid, glutamine for glutamic acid). Conservative changes can further include substitution of chemically homologous non-natural amino acids (i.e., a synthetic non-natural hydrophobic amino acid in place of leucine, a synthetic non-natural aromatic amino acid in place of tryptophan).

"Contacting a cell" is understood herein as providing an agent to a test cell e.g., a cell to be treated in culture or in an animal, such that the agent or isolated cell can interact with the test cell or cell to be treated, potentially be taken up by the test cell or cell to be treated, and have an effect on the test cell or cell to be treated. The agent or isolated cell can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "detecting", "detection" and the like are understood that an assay performed for identification of a specific analyte in a sample, a product from a reporter construct in a sample, or an activity of an agent in a sample.

By "diagnosing" as used herein refers to a clinical or other assessment of the condition of a subject based on observation, testing, or circumstances for identifying a subject having a disease, disorder, or condition based on the presence of at least one sign or symptom of the disease, disorder, or condition. Typically, diagnosing using the method of the invention includes the observation of the subject for other signs or symptoms of the disease, disorder, or condition.

The terms "effective amount," or "effective dose" refers to that amount of an agent to produce the intended pharmacological, therapeutic or preventive result. The pharmacologically effective amount results in the amelioration of one or more signs or symptoms of a disorder provided herein, or prevents the spread of the disorder. For example, a therapeutically effective amount preferably refers to the amount of a therapeutic agent that decreases the rate of cancer spread, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject. More than one dose of an agent may be required to provide an effective dose.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease signs or symptoms, extension of life, improvement in quality of life, or other effect generally recognized as positive by medical doctors familiar with treating the particular type of disease or condition.

As use herein, the "face" of a helix, for example, an alpha-helix or a $3_{10}$ helix, is understood as the amino acids that are "stacked" in a helix of a protein so that when the helix is positioned vertically, the amino acids in a single face are depicted as being one on top of the other. For example, an alpha-helix has about 3.6 amino acids per turn. Therefore, when a peptide having a sequence abcdefga'b'c'd'e'f'g' forms an alpha helix, the fourth and fifth amino acids (i+3 and i+4), i.e., amino acids d and e, will "stack" over the first amino acid (position 1+~3. 6 amino acids), and the eighth amino acid, amino acid a' (i+7), will stack over amino acid a to form a face of the helix and starting a new turn with amino acid a'. In an alpha-helix, amino acid b, the second amino acid, will "stack" with the fifth and sixth amino acids, i.e., amino acids e and fat the +3 and +4 positions, and with amino acid b' at the +7 position to form a face of the helix. Faces on helices starting with amino acid c, d, e, f, and g can be readily determined based on the above disclosure. Furthermore, a face of a helix can include two adjacent, three adjacent, or four adjacent columns of "stacked" residues.

An example of a "face" of a helix includes the "interacting face" of the helix. An "interacting face" amino acid residue is a residue that makes contact with one or more helices in the helix bundle, results in abolishing or substantially abolishing the polypeptide functional activity. Substantially abolishing is understood as reducing the functional activity of a BCL9 peptide to less than about 50%, less than about 40%, less than about 30% of the wild-type peptide in an appropriate assay. The interacting face amino acid residues of the BCL9 peptides can readily be determined by methods well known in the art and are described herein. In one embodiment, an essential amino acid residue is in the "a" or "d" position of a BCL9 HD2 domain, while non-essential amino acids may occur in a "b", "c", "e", "f" or "g" position. The term "interacting face" amino acid residue as used herein, includes conservative substitutions of the interacting face amino acids that do not disrupt function of the sequence. Generally, the "interacting face" amino acid residues are found at the interacting face of the alpha helix.

The BLC9, BCL9-like, and HD2 domain and HD2 domain analogs are readily identifiable by those possessing ordinary skill in the art by sequence based homology, structural homology and/or functional homology. Such methods are well known in the art and include bioinformatics programs based on pairwise residue correlations (e.g., ch.embnet.org/software/COILS_form.html), which have the ability to recognize coils from protein sequences and model their structures (See Lupas, A., et al. Science 1991. 252 (5009); p. 1162-1164).

In one embodiment, the modified polypeptide of the invention is 20% or more similar at the interacting face to the amino acid sequence of SEQ ID NO:1-7. In another embodiment, the modified polypeptide of the invention is 30% or more similar at the interacting face to the amino acid sequence of SEQ ID NO:1-7. In another embodiment, the modified polypeptide of the invention is 40% or more similar at the interacting face to the amino acid sequence of SEQ ID NO:1-7. In another embodiment, the modified polypeptide of the invention is 50% or more similar at the interacting face to the amino acid sequence of SEQ ID NO:1-7. In another embodiment, the modified polypeptide of the invention is 60% or more similar at the interacting face to the amino acid sequence of SEQ ID NO:1-7. In another embodiment, the modified polypeptide of the invention is 70% or more similar at the interacting face to the amino acid sequence of SEQ ID NO:1-7. In another embodiment, the modified polypeptide of the invention is 80% or more similar at the interacting face to the amino acid sequence of SEQ ID NO:1-7. In another embodiment, the modified polypeptide of the invention is 90% or more similar at the interacting face to the amino acid sequence of SEQ ID NO:1-7. The interacting face of BCL9 peptide can be the β-catenin interacting face. The "interacting face" of the alpha helix includes those amino acid residues which interact with other amino acid residues on other proteins and/or in other helices. Methods for identifying repeats and the interacting face residues are well known in the art and described herein.

As used herein, the term "hydrocarbon stapling", refers to a process for stably cross-linking a polypeptide having at least two amino acids that helps to conformationally bestow the native secondary structure of that polypeptide. Hydrocarbon stapling promotes or maintains a helical secondary structure in a peptide predisposed to have a helical secondary structure, e.g., alpha-helical secondary structure, to attain or maintain its native alpha-helical conformation. This secondary structure increases resistance of the polypeptide to proteolytic cleavage and heat, and also may increase hydrophobicity.

The hydrocarbon stapled polypeptides include one or more tethers (linkages) between two non-natural amino acids (or a non-native linkage, e.g., carbon-carbon, from two natural amino acids), which tether significantly enhances the helical secondary structure of the polypeptide. Generally, to promote a helical structure, the tether extends across the length of one or two helical turns (i.e., about 3, 4, or 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , and the amino acid X is independently selected for each position, cross-links between X1 and X4, or between X1 and X5, or between X1 and X8 are useful as are cross-links between X2 and X5, or between X2 and X6, or between X2 and X9, etc. The use of multiple cross-links (e.g., 2, 3, 4 or more) is also contemplated. The use of multiple cross-links is effective at stabilizing and optimizing the peptide, especially with increasing peptide length. The use of "stitched" cross-links has also been achieved whereby double linkages are made from a common origin (e.g., X1, X5, and X9, where X5 is the anchor point for both staples).

Thus, the invention encompasses the incorporation of one or more crosslinks within the polypeptide sequence. The use of multiple cross-links is effective at stabilizing and optimizing the peptide, especially with increasing peptide length. Thus, the invention encompasses the incorporation of one or more crosslinks within a polypeptide sequence, including stitched crosslinks in which two staples arise from a common origin.

As used herein, the term "staple scan" refers to the synthesis of a library of stapled peptides whereby the location of the i and i+3; i and i+4; and i and i+7 single and multiple staple, or stitches, are positioned sequentially down the length of the peptide sequence, sampling all possible positions, to identify desired or optimal properties and activities for the stapled or stitched constructs.

As used herein, the terms "identity" or "percent identity", refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. The identity between two sequences is a direct function of the number of matching or identical positions. Thus, if a portion of the reference sequence is deleted in a particular peptide, that deleted section is not counted for purposes of calculating sequence identity. Identity is often measured using sequence analysis software e.g., BLASTN or BLASTP (available at (www.ncbi.nih.gov/BLAST). The default parameters for comparing two sequences (e.g., "Blast"-ing two sequences against each other), by BLASTN (for nucleotide sequences) are reward for match=1, penalty for mismatch=−2, open gap=5, extension gap=2. When using BLASTP for protein sequences, the default parameters are reward for match=0, penalty for mismatch=0, open gap=11, and extension gap=1. Additional, computer programs for determining identity are known in the art.

As used herein, "isolated" or "purified" when used in reference to a polypeptide means that a natural polypeptide or protein has been removed from its normal physiological environment (e.g., protein isolated from plasma or tissue) or is synthesized in a non-natural environment (e.g., artificially synthesized in an in vitro translation system or using chemical synthesis). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition.

As used herein, "kits" are understood to contain at least one non-standard laboratory reagent for use in the methods of the invention. For example, a kit can include at least one of, preferably at least two of at least one peptide, and instructions for use, all in appropriate packaging. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

A "non-essential" amino acid residue is a residue that can be altered from the wild-type sequence of a polypeptide without abolishing or substantially altering its activity/secondary structure (alpha-helical structure).

"Obtaining" is understood herein as manufacturing, purchasing, or otherwise coming into possession of.

As used herein, "operably linked" is understood as joined, preferably by a covalent linkage, e.g., joining an amino-terminus of one peptide to a carboxy terminus of another peptide, in a manner that the two or more components that are operably linked either retain their original activity, or gain an activity upon joining such that the activity of the operably linked portions can be assayed and have detectable activity using at least one of the methods provided in the examples.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperitoneal, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments).

A "sample" as used herein refers to a biological material that is isolated from its environment (e.g., blood or tissue from an animal, cells, or conditioned media from tissue culture) and is suspected of containing, or known to contain an analyte, such as a virus, an antibody, or a product from a reporter construct. A sample can also be a partially purified fraction of a tissue or bodily fluid. A reference sample can be a "normal" sample, from a donor not having the disease or condition fluid, or from a normal tissue in a subject having the disease or condition (e.g., non-infected tissue vs. a infected tissue). A reference sample can also be from an untreated donor or cell culture not treated with an active agent (e.g., no treatment or administration of vehicle only). A reference sample can also be taken at a "zero time point" prior to contacting the cell or subject with the agent to be tested.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection.

The term "stable" or "stabilized", as used herein with reference to a polypeptide, refers to polypeptides which have been hydrocarbon-stapled to promote and/or maintain helical structure and/or improve protease resistance and/or improve acid stability and/or improve thermal stability and/or improve pharmacologic properties. Stabilized polypeptides are a type of structurally constrained polypeptides.

As used herein, "structurally constrained peptides" and the like are understood to include modified peptides having any (i.e., at least one) chemical modification, e.g., mutation of the original or native sequence with a natural or non-natural amino acid; chemical modification to incorporate a molecular tether; chemical modification to promote the formation of a disulfide bridge; etc. such that the structurally constrained peptide adopts a more limited number of structures than the unmodified peptide. A structurally constrained peptide can include 1, 2, 3, 4, 5, 6, 7, 8, 9, 10, 11, 12, or more mutations as compared to the native, wild-type sequence. For example, molecular tethers can include hydrocarbon staples to promote the formation of stable helical structures, especially alpha-helical and $3_{10}$ structures, or kinks depending on the positions of the ends of the tethers and the lengths of the tethers. Natural or non-natural amino acids can be employed to promote kinks (e.g., bends in the structure as defined by the variable angles between the two adjoining structures) or other preferred confirmations. For example, the natural amino acid proline can induce a kink in a peptide due to the structure of the amino acid R group and the lack of a hydrogen-bond donor. Non-natural amino acids, particularly those having large and/or charged R groups, or N-methylated amides, N-substituted glycines, cyclic alpha, alpha-disubstitution, cyclic N,N-disubstitution, and beta-amino acids can promote specific, desired confirmations. It is understood that a population of "structurally constrained" peptides in solution may not all have the desired confirmation all of the time. Instead, in a population of structurally constrained peptides in solution, the desired confirmation is present at least about 30%, 40%, 50%, 60%, 70%, 80%, 90%, 100%, or more of the time than the native or original peptide sequence in solution prior to chemical modification. The structure of a population of peptides in solution can be determined by various methods known to those of skill in the art including, but not limited to, circular dichroism and NMR spectroscopy. X-ray crystallography can be applied to determine the structure of a constrained peptide when packed in the form of a crystal.

"Small molecule" as used herein is understood as a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

An agent, polypeptide, nucleic acid, or other compound "specifically binds" a target molecule, e.g., antigen, polypeptide, nucleic acid, or other compound, when the target molecule is bound with at least 100-fold, preferably at least 500-fold, preferably at least 1000-fold, preferably at least a 5000-fold, preferably at least a 10,000-fold preference as compared to a non-specific compounds, or a pool of non-specific compounds. Specifically binds can be used in relation to binding one of two or more related compounds that have physically related structures. Binding preferences and affinities, absolute or relative, can be determined, for example by determining the affinity for each pair separately or by the use of competition assays or other methods well known to those of skill in the art.

A "subject" as used herein refers to living organisms. In certain embodiments, the living organism is an animal. In certain preferred embodiments, the subject is a mammal. In certain embodiments, the subject is a domesticated mammal. Examples of subjects include humans, monkeys, dogs, cats, mice, rats, cows, horses, goats, and sheep. A human subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome.

"Therapeutically effective amount," as used herein refers to an amount of an agent which is effective, upon single or multiple dose administration to the cell or subject, in prolonging the survivability of the patient with such a disorder, reducing one or more signs or symptoms of the disorder, preventing or delaying infection, preventing or delaying the progression of a disease or disorder and the like beyond that expected in the absence of such treatment.

An agent can be administered to a subject, either alone or in combination with one or more therapeutic agents, as a pharmaceutical composition in mixture with conventional excipient, e.g., pharmaceutically acceptable carrier, or therapeutic treatments.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, Pa., 1985). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive, i.e., 1, 2, 3, 4, 5, 6, 7, 8, 9, 10, 11, 12, 13, 14, 15, 16, 17, 18, 19, or 20) carbon atoms in it. The term "alkylene" refers to a divalent alkyl (i.e., —R—).

The term "alkenyl" refers to a hydrocarbon chain that may be a straight chain or branched chain having one or more carbon-carbon double bonds. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "halo" refers to any radical of fluorine, chlorine, bromine or iodine.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

Ranges provided herein are understood to be shorthand for all of the values within the range. This includes all individual sequences when a range of SEQ ID NOs: is provided. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

The symbol

when used as part of a molecular structure refers to a single bond or a trans or cis double bond.

Any compositions or methods provided herein can be combined with one or more of any of the other compositions and methods provided herein.

Pharmaceutical Compositions and Routes of Administration

One or more structurally constrained peptide of the instant invention can be used in a pharmaceutical composition for the treatment of a disorder provided herein. Treatment method provided herein can be performed using a combination of the structurally constrained peptides, which can be selected and combined to treat the disorder in the subject. For example, a pharmaceutical composition of the instant invention can include 2, 3, 4, 5, 6, 7, 8, 9, 10, 11, 12, 13, 14, 15, or more structurally constrained peptides. The structurally constrained peptides can also be combined with other agents, e.g., anti-cancer agents or angiogenesis inhibitors.

As used herein, the compounds of this invention are defined to include pharmaceutically acceptable derivatives thereof. A "pharmaceutically acceptable derivative" means any pharmaceutically acceptable salt, ester, salt of an ester, or other derivative of a compound of this invention which, upon administration to a recipient, is capable of providing (directly or indirectly) a compound of this invention. Particularly favored derivatives are those that increase the bioavailability of the compounds of this invention when such compounds are administered to a mammal (e.g., by allowing an orally administered compound to be more readily absorbed into the blood, to increase serum stability or decrease clearance rate of the compound) or which enhance delivery of the parent compound to a biological compartment (e.g., the brain or lymphatic system) relative to the parent species. Derivatives include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_{4+}$ salts. This invention also envisions the quaternization of any basic nitrogen-containing groups of the compounds disclosed herein. Water or oil-soluble or dispersible products may be obtained by such quaternization.

The compounds of the invention can, for example, be administered by injection, intravenously, intraarterially, subdermally, intraperitoneally, intramuscularly, or subcutaneously; or orally, buccally, nasally, transmucosally, intravaginally, cervically, topically, in an ophthalmic preparation, or by inhalation, with a dosage ranging from about 0.001 to about 100 mg/kg of body weight, or according to the requirements of the particular drug and more preferably from 0.5-10 mg/kg of body weight. The methods herein contemplate administration of an effective amount of compound or compound composition to achieve the desired or stated effect.

The amount of active ingredient that may be combined with the carrier materials to produce a single dosage form will vary depending upon the host treated and the particular mode of administration. A typical preparation will contain from about 1% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise compounds of the invention or a pharmaceutically acceptable salt thereof; an additional agent including for example, one or more therapeutic agents for the prevention and/or treatment of a disorder provided herein, particularly for the prevention and/or treatment of cancer, and any pharmaceutically acceptable carrier, adjuvant or vehicle. Alternate compositions of this invention comprise a compound of the invention or a pharmaceutically acceptable salt thereof; and a pharmaceutically acceptable carrier, adjuvant or vehicle. The compositions delineated herein include the compounds of the invention delineated herein, as well as additional therapeutic agents if present, in amounts effective for achieving a modulation of disease or disease symptoms, including cancer or symptoms thereof.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α.-tocopherol polyethyleneglycol 1000 succinate, surfactants used in pharmaceutical dosage forms such as Tween® or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, may also be advantageously used to enhance delivery of compounds of the formulae described herein.

The pharmaceutical compositions of this invention may be administered enterally for example by oral administration, parenterally, by inhalation spray, topically, rectally, nasally, buccally, vaginally or via an implanted reservoir, preferably by oral or vaginal administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases, or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional, and intracranial injection or infusion techniques.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase and is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of the invention may be administered topically or intravaginally. The pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. In still another embodiment, the pharmaceutical composition is formulated as a vaginal ring. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Effective dosages of the peptides of the invention to be administered may be determined through procedures well known to those in the art which address such parameters as biological half-life, bioavailability, and toxicity.

A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (e.g., the concentration of the test compound which achieves a half-maximal inhibition of the BCL9/b-catenin protein interaction or functional surrogate thereof as measured by an assay relative to the amount of the event in the absence of the test compound) as determined in cell culture. Such information can be used to more accurately determine useful doses in humans. Levels in plasma may be measured, for example, by high performance liquid chromatography (HPLC) or mass spectrometry (MS).

Kits

The present invention also encompasses a finished packaged and labeled pharmaceutical product or laboratory reagent. This article of manufacture includes the appropriate instructions for use in an appropriate vessel or container such as a glass vial or other container that is hermetically sealed. A pharmaceutical product may contain, for example, a compound of the invention in a unit dosage form in a first container, and in a second container, sterile water or adjuvant for injection. Alternatively, the unit dosage form may be a solid suitable for oral, transdermal, intranasal, intravaginal, cervical ring, or topical delivery.

In a specific embodiment, the unit dosage form is suitable for intravenous, intramuscular, intraperitoneal, intranasal, oral, intravaginal, cervical, topical or subcutaneous delivery. Thus, the invention encompasses solutions, solids, foams, gels, preferably sterile, suitable for each delivery route.

As with any pharmaceutical product, the packaging material and container are designed to protect the stability of the product during storage and shipment. Further, the products of the invention include instructions for use or other informational material that advise the physician, technician, or patient on how to appropriately prevent or treat the disease or disorder in question. In other words, the article of manufacture includes instructions indicating or suggesting a dosing regimen including, but not limited to, actual doses, monitoring procedures (e.g., detection and quantitation of infection), and other monitoring information.

Specifically, the invention provides an article of manufacture including packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a compound of the invention, and wherein said packaging material includes instruction means which indicate that said compound can be used to manage, treat, and/or ameliorate one or more symptoms associated with a disease provided herein, by administering specific doses and using specific dosing regimens as described herein.

The following examples are provided merely as illustrative of various aspects of the invention and shall not be construed to limit the invention in any way.

Disorders Treated by the Invention

In certain embodiments, the disease or disorder treated by the stabilized peptides of the invention is associated with angiogenesis. In certain embodiments, the disease is selected from: tumor or cancer growth (neoplasia), skin disorders, neovascularization, inflammatory and arthritic diseases, retinoblastoma, cystoid macular edema (CME), exudative age-related macular degeneration (AMD), diabetic retinopathy, diabetic macular edema, or ocular inflammatory disorders.

In various embodiments, the structurally constrained peptides of the invention can be used for overcoming cancer stem cell chemo- and radioresistance (treatment-resistance).

In certain embodiments, the disease or disorder is tumor or cancer growth (neoplasia). In a further embodiment, the disease or disorder is ocular cancer, rectal cancer, colon cancer, colorectal caner, cervical cancer, prostate cancer, breast cancer, bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer, throat cancer, multiple myeloma, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In other embodiments, the disease or disorder is a skin disorder. In a further embodiment, the disease or disorder is psoriasis, acne, rosacea, warts, eczema, hemangiomas, lymphangiogenesis, Sturge-Weber syndrome, venous ulcers of the skin, neurofibromatosis, and tuberous sclerosis.

In certain embodiments, the disease or disorder is neovascularization. In a further embodiment, the disease or disorder is diabetic retinopathy, retinopathy of prematurity, corneal graft rejection, neovascular glaucoma, retrolental fibroplasias, epidemic keratoconjunctivitis, vitamin A deficiency, contact lens overwear, atopic keratitis, superior limbic keratitis, pterygium keratitis sicca, Sjogren's, acne rosacea, phlyctenulosis, syphilis, Mycobacteria infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, macular edema, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications, and diseases associated with rubeosis (neovascularization of the ankle).

In certain embodiments, the disease or disorder is inflammatory and arthritic disease. In a further embodiment, the disease or disorder is rheumatoid arthritis, osteoarthritis, lupus, scleroderma, Crohn's disease, ulcerative colitis, psoriasis, sarcoidosis, Sarcoidosis, skin lesions, hemangiomas, Osler-Weber-Rendu disease, hereditary hemorrhagic telangiectasia, and osteoarthritis.

In other embodiments, the disease or disorder affects the dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle, or respiratory tract.

EXAMPLES

Example 1. Peptide Synthesis and Circular Dichroism

Figure 14:
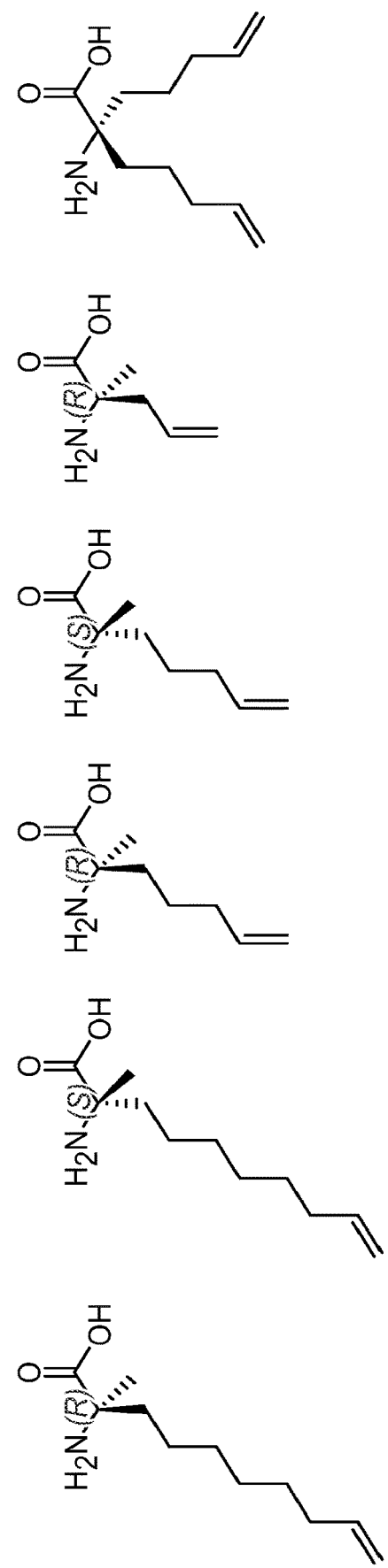
FIG. 14 shows examples of non-natural olefinic amino acids inserted into peptide templates to generate hydrocarbon-stapled peptides by olefin metathesis.
Figure 16:
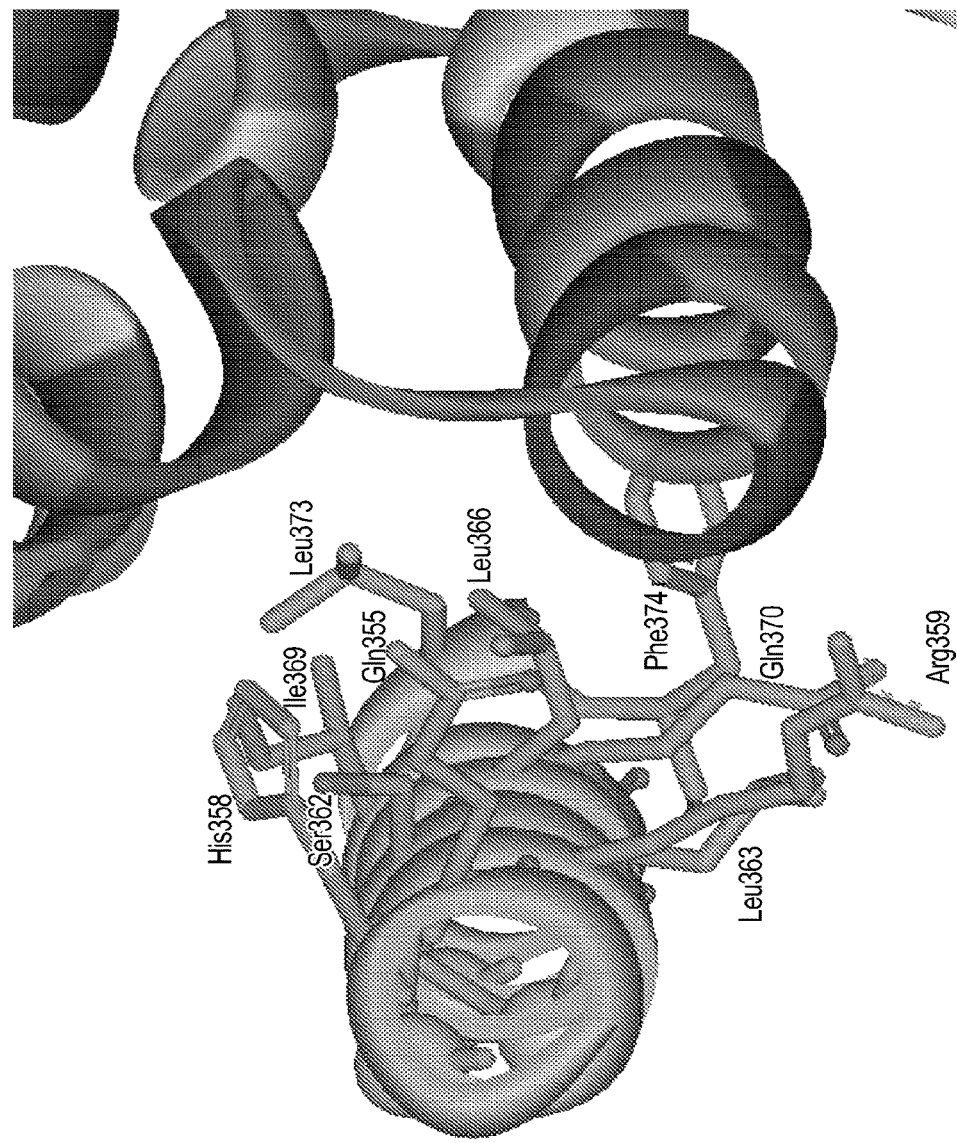
FIG. 16 shows that three dimensional structure of residues 351-374 of the α-helical HD2 domain of BCL9 (SEQ ID NO. 140), highlighting those amino acid residues of the BCL9 HD2 interaction face that contact β-catenin.

To generate stabilized alpha-helices of the BCL9 HD2 domain, which directly interacts with b-catenin (FIG. 16), syntheses of hydrocarbon stapled peptides (FIG. 14, FIG. 15) were performed as previously described (Walensky, L. D. et al. Science 305, 1466-70 (2004); Bird, G. H., et al., Methods Enzymol 446, 369-86 (2008); Bird et al. PNAS 107, 14093-8, (2010)). Peptides were produced on an Apex 396 (Aapptec) automated peptide synthesizer using Rink amide AM LL resin (EMD Biosciences, 0.2 mmol/g resin), at 50 mmol scale. The standard Fmoc protocol employed 2×10 min deprotections in 20% piperidine/NMP followed by a pair of consecutive methanol and dimethylformamide (DMF) washes. The incorporated non-natural amino acids were treated with 4×10 min incubations in 20% piperidine/NMP to achieve complete deprotection. Amino acid coupling was performed using 0.4 M stock solutions of Fmoc-protected amino acids, 0.67 M 2-(6-chloro-1H-benzotriazole-1-yl)-1,1,3,3-tetramethylaminium hexafluorophosphate (HCTU), and 2 M N,N-diisopropyl ethylamine (DIEA), yielding 1 mL of 0.2 M active ester (4 equivalents). Coupling frequency and incubation times were 2×30 min for standard residues, 2×45 min for the olefinic non-natural amino acids, and 3×45 min for the residue following a non-natural amino acid. Upon completion of automated synthesis, the amino terminus was either acetylated or capped with Fmoc-β-Ala for FITC derivatization. To generate hydrocarbon staples by olefin metathesis, the resin was charged with a 10 mM solution of bis(tricyclohexylphosphine)-benzylidene ruthenium (IV) dichloride (Grubbs' first generation catalyst) in 1,2-dichloroethane and stirred for 2 hours twice. For FITC derivatization, Fmoc-β-Ala was deprotected with piperidine in NMP and then reacted with fluorescein isothiocyanate (FITC) and triethylamine in dimethylformamide overnight. The peptide was cleaved from the resin and deprotected in TFA/triisopropyl silane (TIS)/water (95%, 2.5%, 2.5%), and precipitated with diethylether/hexanes. Stapled peptides were purified by reverse-phase HPLC (Agilent) using a C18 column (Zorbax), characterized by LC/MS (mass spectra obtained using electrospray in positive ion mode), and quantified by amino acid analysis (AAA) on a Beckman 6300 high-performance amino acid analyzer. Working stock solutions were generated by dissolving the lyophilized powder in 100% DMSO at 1 to 10 mM. SAH-gp41 powder and DMSO solutions were stored at −20° C. Determination of α-helicity was performed as previously described (Walensky, L. D. et al. Science 305, 1466-70 (2004); Bird, G. H., et al., Methods Enzymol 446, 369-86 (2008)). See experimental results in FIG. 1A-FIG. 1C, FIG. 1G.

Example 2. Protein Production and Purification

Recombinant human BCL9 (214-493) was cloned into pET-23a (+) was cloned into pET-23a (+) vector (Novagen) containing carboxy-terminal hexa-histidine tag (SEQ ID NO: 141) E. coli BL21 (DE3) competent cells (Stratagene) were transformed, incubated at 37° C. until A600=0.6 was reached and then induced with 1 mM isopropyl-β-D-thiogalactoside (IPTG) for 3 h. Cells were harvested by centrifugation and lysed by sonication in 50 mM $Na_2HPO_4$, pH 8.0, 0.3M NaCl buffer. The lysates were then centrifuged and loaded onto HIS-Select Nickel Affinity Gel (Sigma) and washed with wash buffer (50 mM $NaH_2PO_4$, pH 8.0, 0.3M NaCl and 10 mM imidazole). The protein was eluted in 50 mM $Na_2HPO_4$, pH 8.0, 0.3M NaCl and 250 mM imidazole and dialyzed overnight in sterile 1×PBS. Human β-catenin constructs (e.g., residues 1-781, 138-683, 273-684) were cloned into pGEX4T1/pGEX4T2, pET-28a, and pET-23a respectively. His-tagged fusion proteins were generated as described above for BCL9. For GST-tagged constructs, transformed E. coli BL21 (DE3) were cultured at 37° C. to A600=0.6 and induced with 1 mM IPTG for 4 h. Cells were pelleted, resuspended and sonicated in Buffer A (50 mM Tris, pH 8.0, 150 MM NaCl, sucrose 20%, 5 mM dithiothreitol (DTT), 1 mM EDTA, 1 mM PMSF, 2 mg/ml aprotinin, and 0.7 mg/ml pepstatin). Solubilized proteins were adsorbed to glutathione-Sepharose 4B beads (GE), which were then eluted in Buffer A with 20 mM glutathione and dialyzed against PBS buffer supplemented with protease inhibitor cocktail tablets (Roche).

Example 3. GST Pull-Down Assays

Equal amounts (0.5 μM) of His-tagged BCL9 and GST-tagged β-catenin bound to glutathione-Sepharose 4B beads (GE) were incubated with or without increasing amounts of HD2 or SAH-BCL9 peptides for 1 h at 4° C. in a final volume of 1000 μl PBS. Protein complexes were pelleted by centrifugation at 2000 rpm for 2 min and beads washed four times with PBS buffer. The beads were then taken up in SDS-PAGE loading buffer, boiled, and SDS-PAGE performed to visualize bound proteins by Coomassie staining.

Example 4. Patient Samples and Cell Lines

Bone marrow specimens were obtained from patients with MM in accordance with Dana-Farber Cancer Institute Review Board approval and informed consent performed in compliance with the Declaration of Helsinki. Primary CD138+ plasma cells were purified using magnetic beads as described (Sukhdeo, K. et al. Proc Natl Acad Sci USA 104, 7516-21 (2007)). CRC primary tumor samples were obtained from the Brigham and Women's Hospital in accordance with the policies of their Institutional Review Board. To generate sufficient CRC primary tumor cells for experimentation, the primary tumors were first expanded subcutaneously in NOD/SCID mice (Jackson Laboratory). After the tumors reached 2 cm in diameter, mice were sacrificed according to institutional guidelines and subcutaneous tumor xenografts were minced with a scalpel and digested by incubation with collagenase IV (Worthington Biomedical Corporation) and 0.01% DNase I (Sigma-Aldrich) at 37° C. for 30 min, followed by additional mechanical disaggregation using a Stomacher device (Seward Laboratory Systems Inc.). Samples were filtered through a 70 µm cell strainer and washed with PBS. Red blood cells were lysed using ACK lysing buffer (BioWhittaker, Lonza) and viable tumor cells were enriched by Ficoll-Paque gradient centrifugation (GE Healthcare). To purify viable tumor cells only, the samples were treated with APC conjugated anti-mouse H-2Kd (clone SF1-1.1.1, eBioscience), FITC-conjugated anti-human EpCAM antibodies (clone Ber-EP4, Dako), and Hoechst 33258 (Sigma-Aldrich), and then FACSAria flow sorting (BD Biosciences) was used to isolate the EpCAM-positive, H-2Kd-negative, and Hoechst-negative primary tumor cells. Cultured cell lines were maintained as previously described (Mani, M. et al. Cancer Res 69, 7577-86 (2009)). See results in FIG. 3B, FIG. 3D.

Example 5. Immunoblotting and Co-Immunoprecipitation

Western blotting, performed as described (Sukhdeo, K. et al. Proc Natl Acad Sci USA 104, 7516-21 (2007)), employed the following primary antibodies: BCL9 (6109) (Mani, M. et al. Cancer Res 69, 7577-86 (2009)), BCL9 (ab37305, Abcam), B9L (AF4967, R&D Systems), β-catenin (CATS-H10, Zymed), FITC (ab19224, Abcam), Actin-HRP (C-11, Santa Cruz), Caspase3 (#9662, Cell Signaling), IxBα (#9242, Cell signaling), PARP (#9542, Cell Signaling), E-cadherin (#3195, Cell Signaling), and Lamin B (sc-6217, Santa Cruz). Horseradish peroxidase conjugated secondary antibodies were purchased from Santa Cruz and SouthernBiotech. Co-immunoprecipitation was performed as described (Walensky, L. D. et al. Science 305, 1466-70 (2004)). Briefly, cells were lysed in 50 mM Tris, 150 mM NaCl, and 1% CHAPS buffer containing protease and phosphatase inhibitors. Lysates were precleared with Protein A/G PLUS-agarose beads (Santa Cruz Biotechnologies) for 3 hours followed by overnight incubation at 4° C. with the respective antibodies. Agarose A/G beads were then added for 4 h, pelleted, and washed as described (Walensky, L. D. et al. Science 305, 1466-70 (2004)). See results in FIG. 1D, FIG. 1H, FIG. 2A, FIG. 8.

Example 6. SAH-BCL9 Cellular Uptake and Localization Analyses

Figure 7A:
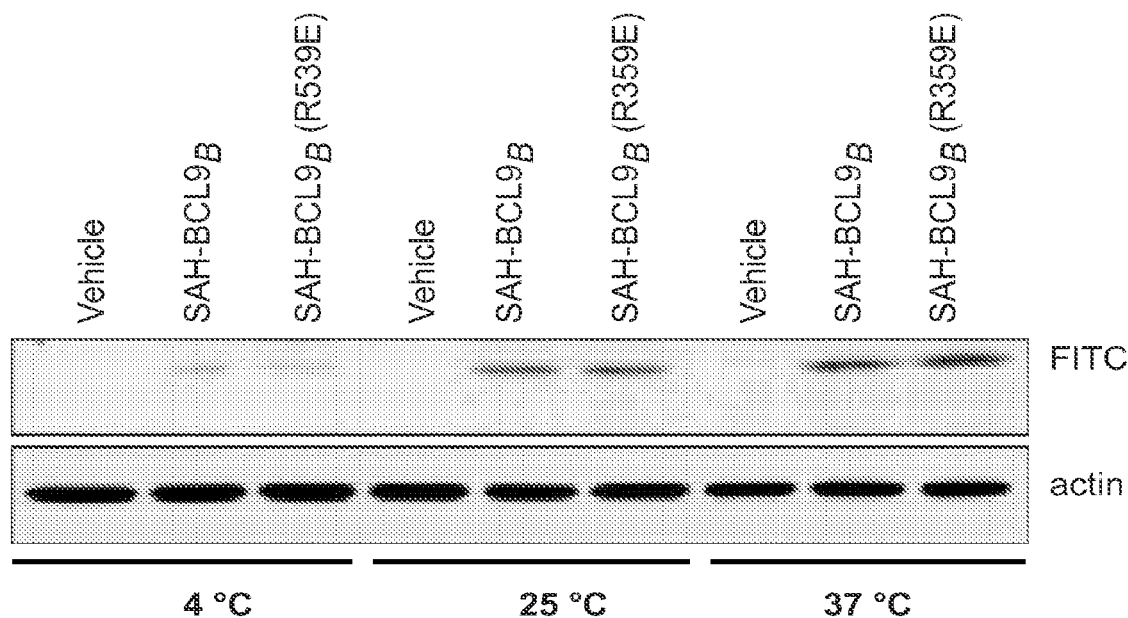
FIG. 7A-FIG. 7B show equivalent cellular uptake of SAH-BCL9 peptides.
Figure 7B:
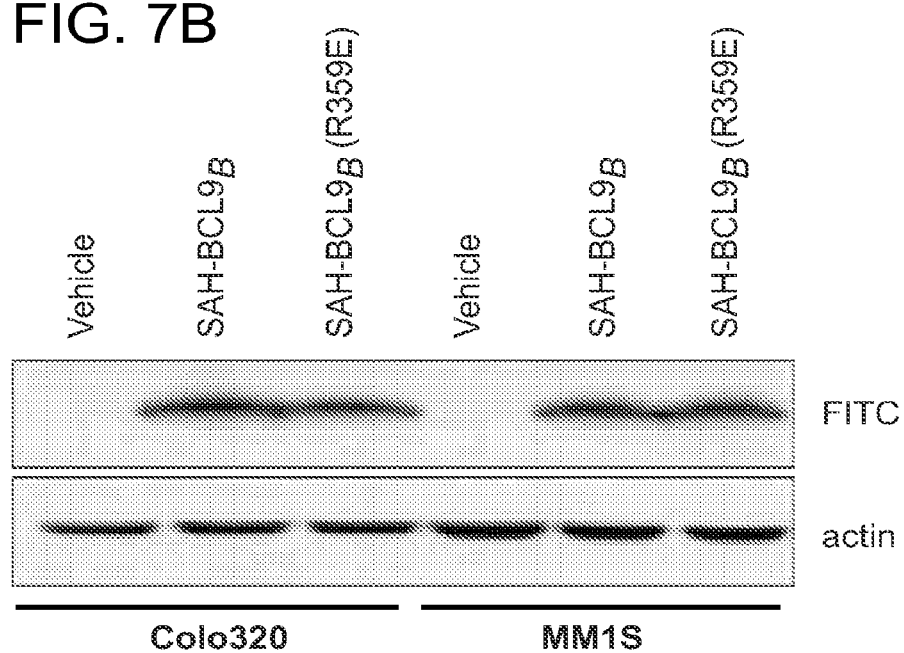
Figure 8A:
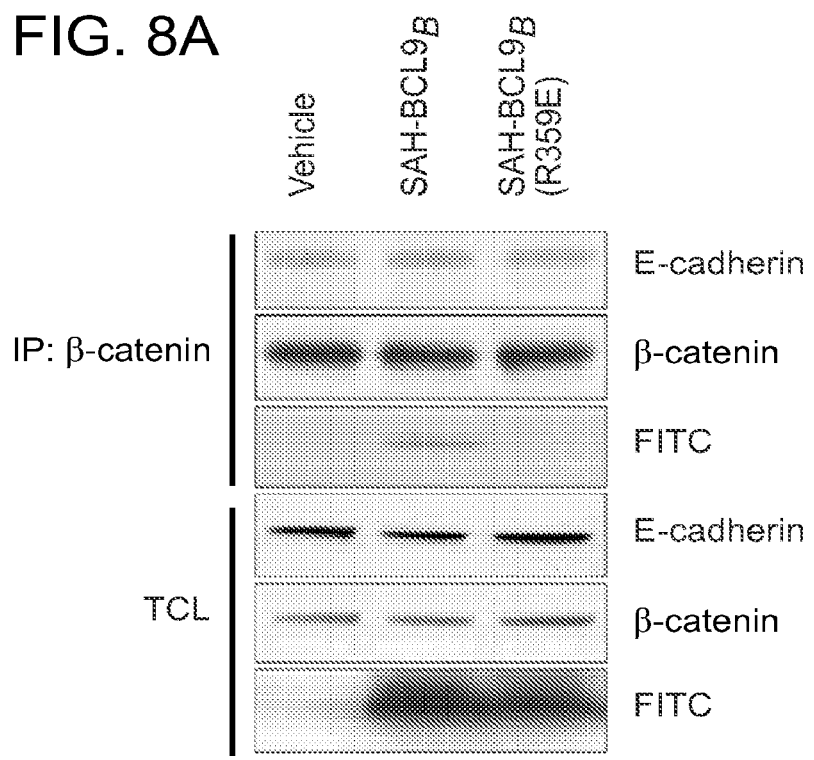
FIG. 8A-FIG. 8B show that SAH-BCL9$_B$ selectively engages β-catenin and does not disrupt its interaction with a non-BCL9 binding partner.
Figure 8B:
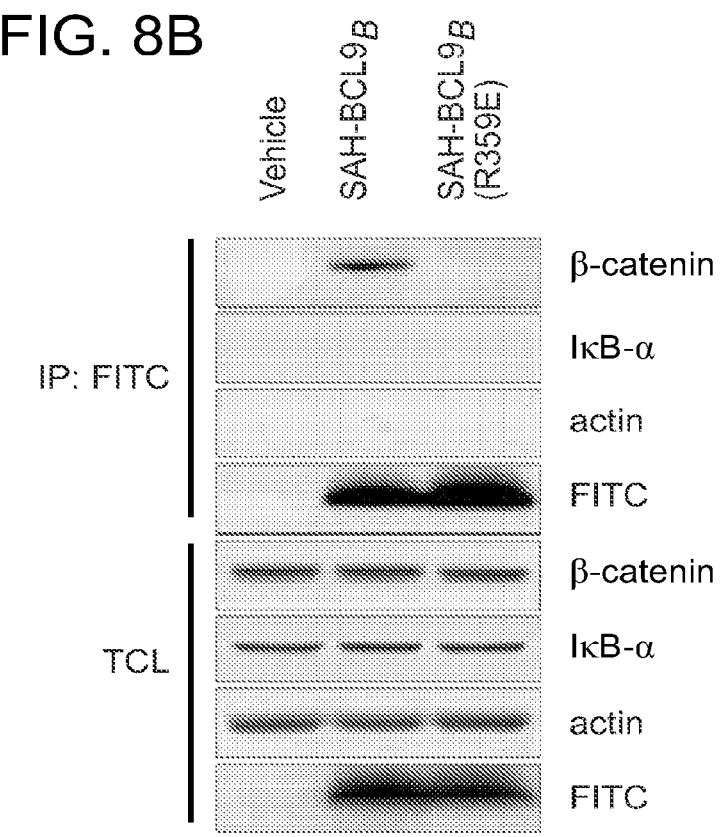

For fluorescence microscopy evaluation, cells were prepared using a cytocentrifuge (Thermo Shandon) and fixed as previously described (Sukhdeo, K. et al. Proc Natl Acad Sci USA 104, 7516-21 (2007); Mani, M. et al. Cancer Res 69, 7577-86 (2009)). Anti-β-catenin and rhodamine-conjugated secondary antibodies (5 µg/ml; Southern Biotechnology) were employed. Images were obtained using a BioRad Radiance 2000 laser scanning confocal microscope. Cell permeability of SAH-BCL9$_B$ and SAH-BCL9$_B$(R359E) were determined by fluorescence microscopy of cells treated with FITC-derivatives of the above described stapled peptides and also by blotting/fluorescence scan, performed as previously described (Fitter, K. et al Methods Enzymol, 446, (2008), 387-408; Walensky, L. D. et al. Science 305, 1466-70 (2004). See results in FIG. 1E, FIG. 7.

Example 7. Histopathological Analysis and Immunohistochemistry

Tissue sections were process as described (Sukhdeo, K. et al. Proc Natl Acad Sci USA 104, 7516-21 (2007)). Sections were incubated with primary antibodies (5 µg/ml) or the corresponding IgG fraction of preimmune serum overnight at 4° C. in blocking solution (3% BSA/PBS). BCL9 (ab37305, Abcam), mouse CD34 (RAM34, eBiosciences), human CD34 (M7165, Dako) and human CD44H (2C5, R&D Systems) antibodies were employed. Blood vessel formation in the CRC and MM models was evaluated using anti-mouse CD34 and anti-human CD34 antibodies, respectively, and the corresponding biotinylated antibodies coupled to streptavidin peroxidase (Vector). The number of blood vessels was determined by counting the mean number of independent blood vessels in 5 randomly selected fields at 50× magnification as highlighted by CD34 staining (brown color). See results in FIG. 4B, FIG. 4E, FIG. 4I, FIG. 6.

Example 8. Quantitative Reverse Transcription-PCR

RNA was extracted with TRIzol Reagent (Invitrogen) according to the manufacturer's protocol. Total RNA (2 µg) was reverse transcribed (SuperScript VILO cDNA synthesis kit, Invitrogen) and qPCR was performed using an Applied Biosynthesis 7500 Real-time PCR system. Analysis of target genes was conducted in quadruplicate using POWER SYBR Green Master Mix (Applied Biosystems) with previously described primer sets. Transcripts levels were normalized to β-actin expression. These experiments were repeated three times. See results in FIG. 2B, FIG. 2C.

Example 9. Gene Expression Profiling

RNA from SAH-BCL9$_B$ and vehicle (0.1% DMSO)-treated cells were run on an Affymetrix U133A 2.0 array chip as described (Mollering et al, Nature 462, 182-8 (2009). Statistical analyses were performed in R (http://www.r-project.org). The array data were normalized with rma method (Bolstad, B. M., et al. Bioinformatics 19, 185-93 (2003)) as implemented in the Affy package (http://www.bioconductor.org/packages/2.6/bioc/html/affy.html) and differential expression calculated with empirical Bayes shrinkage of the standard errors toward a common value with LIMMA (http://www.bioconductor.org/packages/2.6/bioc/html/limma.html) (McCarthy, D. J. & Smyth, G. K. Bioinformatics 25, 765-71 (2009); Smyth, G. K. Stat Appl Genet Mol Biol 3, Article3 (2004)). Gene set enrichment analysis was performed using GSEA software (version 2.06) and mSigDB (version 2.5) (Subramanian, A. et al. Proc Natl Acad Sci USA 102, 15545-50 (2005)).

Example 10. Cell Proliferation, Viability Assay and Detection of Apoptosis

Cell proliferation assays were performed as described (Sukhdeo, K. et al. Proc Natl Acad Sci USA 104, 7516-21

(2007)). Cell viability was measured using the CellTiter-Glo assay (Promega) according to the manufacturer's instructions. Apoptosis was evaluated by activated caspase-3 and PARP western blotting. See results in FIG. 3A-FIG. 3F, FIG. 13, and FIG. 20.

Example 11. Angiogenesis and Invasion Assays

Angiogenesis was evaluated as previously described (Mani, M. et al. Cancer Res 69, 7577-86 (2009)) using an in vitro angiogenesis assay kit (Millipore). For capillary tube formation analysis, HUVEC were cultured on polymerized matrix gel and exposed to supernatant media collected from Colo320 or MM1S cells treated with vehicle (0.5% DMSO), SAH-BCL9$_B$ peptides (5 µM) for 24 h. The number of capillary tubes formed after 5 h treatment at 37° C. was determined by counting 5 randomly selected fields at 40× magnification, according to manufacture's instructions. HUVEC cultured in VEGF media and VEGF-free media were used as positive and negative controls, respectively. Cellular invasion assays were performed using Matrigel Boyden chambers (BD Biosciences) as described (Mani, M. et al. Cancer Res 69, 7577-86 (2009)). The reported data represent the average of three independent experiments performed in triplicate. See results in FIG. 3H-FIG. 3I.

Example 12. In Vivo Anti-Tumor Effect of SAH-BCL9$_B$ (Xenograft Models)

GFP-positive Colo320 cells were generated as previously reported (Mani, M. et al. Cancer Res 69, 7577-86 (2009)). Cells were pelleted, resuspended in sterile 1×PBS and injected intraperitoneally (1×10$^6$ cells/mouse) into 5-week-old sublethally irradiated NOD.CB17-PrkdcSCID/J mice (Jackson Laboratory) (n=6 per cohort). Two days after cellular inoculation, mice were treated by intraperitoneal injection with vehicle (2.5% DMSO in D5W) or SAH-BCL9 peptides (20 mg/kg) on alternate days for a total of 6 doses. Forty days after tumor cell injection, the mice were euthanized and GFP-positive tumor visualized using an ImageQuant LAS-4000 (GE Healthcare). Complete necropsies were performed for each experimental animal and livers were sectioned in their entirety at 5 mm intervals for quantitation of tumor metastases. Tissues were subjected to H&E staining and immunohistochemical analysis using anti-CD34 and anti-CD44 antibodies.

Figure 22:
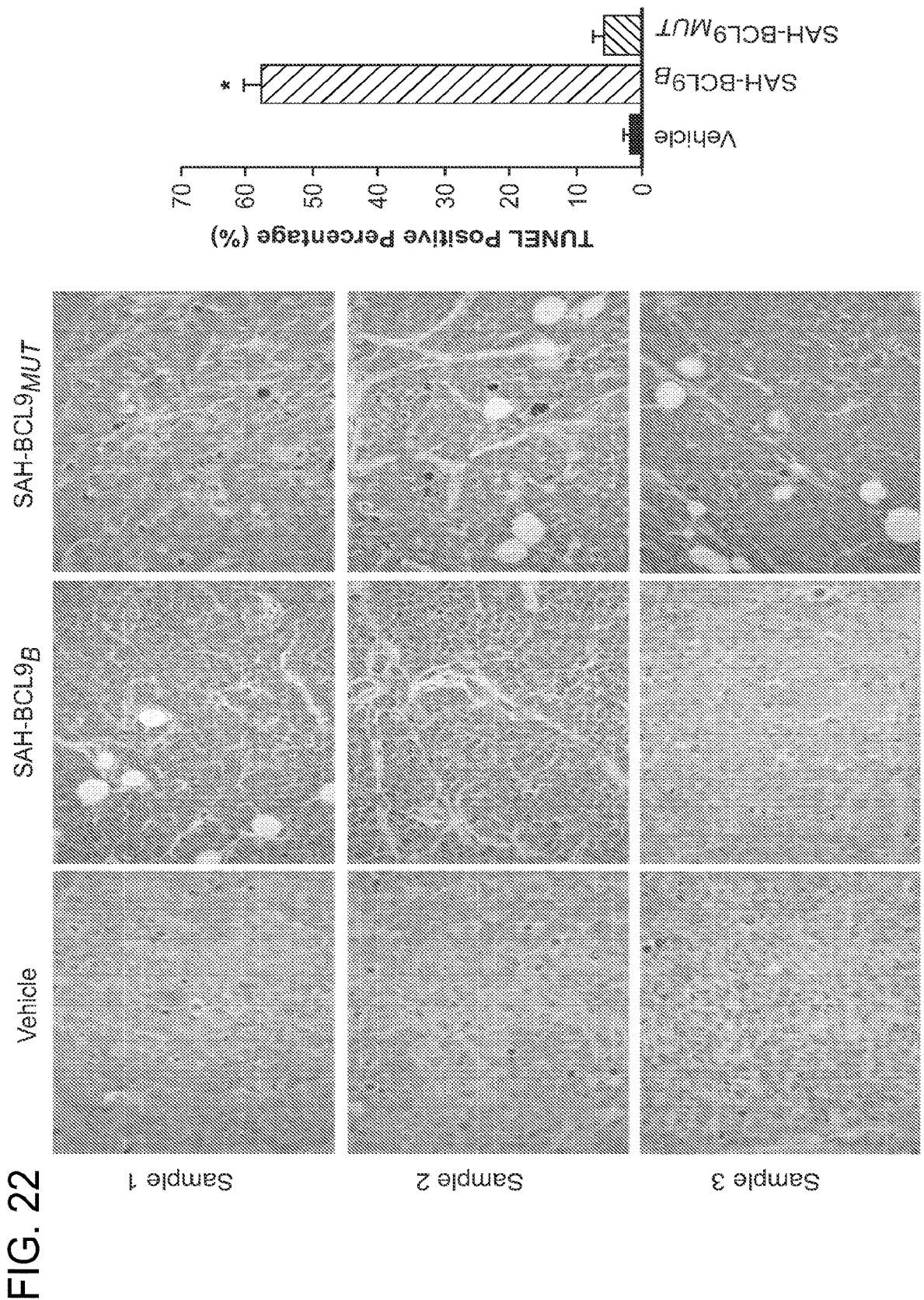
FIG. 22 shows increased apoptosis in colonic tumor tissue of SAH-BCL9$_B$-treated mice. Tumor tissue of NOD/SCID mice bearing intraperitoneal Colo320 cells were evaluated for apoptosis induction using TUNEL assay (brown). SAH-BCL9$_B$, but not vehicle or SAH-BCL9$_{MUT}$, notably increased TUNEL positivity. Three representative 40× power fields are shown, including quantitation of TUNEL positivity in 6 high power fields. * p<0.001.
Figure 23A:
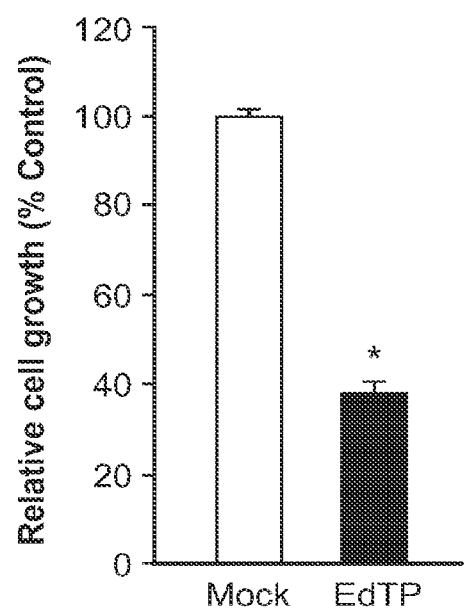
FIG. 23A FIG. 23B show that proliferation of INA-6 cells is dependent on Wnt transcriptional activity and increased apoptosis in myeloma tumor tissue of SAH-BCL9$_B$-treated mice.
Figure 23B:
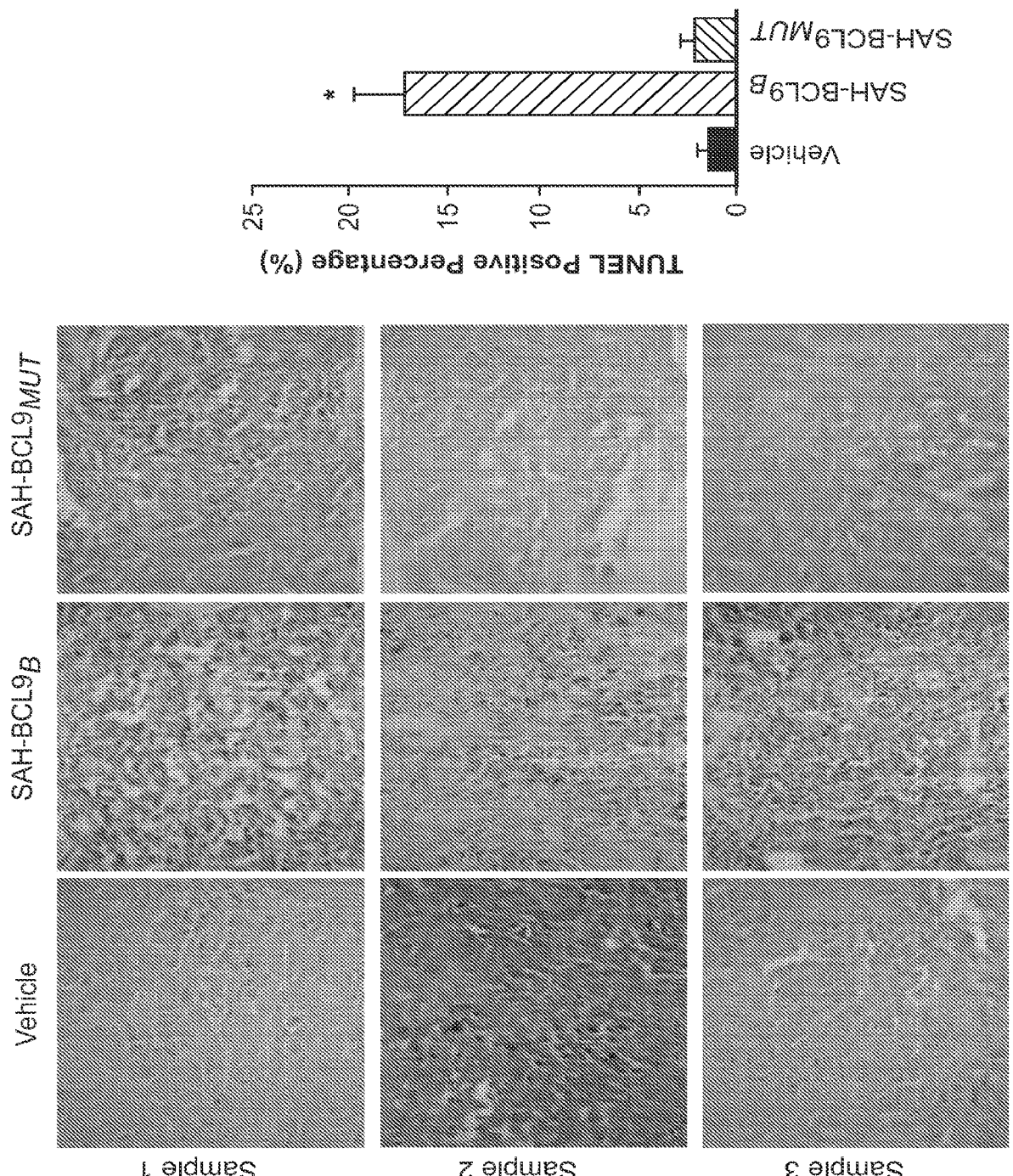

For the SCID-hu murine model of human MM, human fetal bone grafts measuring 1.5×0.5 cm were subcutaneously implanted into eight week old male CB-17 SCID mice (Taconic) as previously described (Tassone, P. et al. Blood 106, 713-6 (2005)). Four weeks after bone implantation, 5×10$^6$ GFP-positive INA-6 MM cells were injected directly into each bone implant. Two days later, mice were treated with 100 µl injections of vehicle (2.5% DMSO in D5W) or SAH-BCL9 peptides (5 mg/kg) instilled adjacent to the bone chips on alternate days for a total of 10 doses. Mouse sera were serially monitored for shuIL-6R levels by ELISA (R&D Systems). Thirty-three days after tumor cell injection, the mice were sacrificed and analyzed for tumor burden by fluorescence imaging and histologic analysis of the bone grafts. See results in FIG. 4A-FIG. 4I. In addition, TUNEL staining was performed on samples obtained from the mice. The results demonstrated that there is an increase in apoptotic tumor cells in animals treated with SAH-BCL9$_B$ compared to vehicle or SAH-BCL9$_{MUT}$-treated mice. See results in FIG. 22 and FIG. 23. All animal experiments were performed in accordance with approved protocols of the Dana-Farber Cancer Institute Animal Care and Use Committee.

Example 13. In Vivo Effect of SAH-BCL9$_B$ on Wnt Reporter Activity

Figure 9:
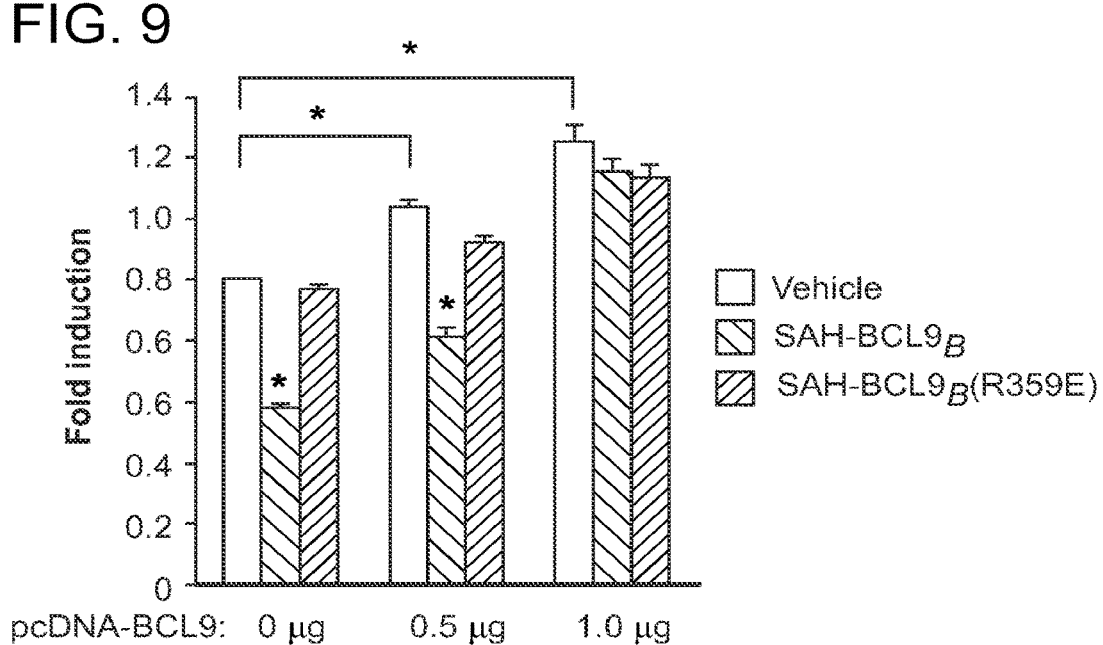
FIG. 9 shows that suppression of β-catenin/BCL9-driven transcription by SAH-BCL9$_B$ is dose-responsively reversed by increased expression of BCL9. HCT116 cells transfected with TOP-FLASH and pcDNA-BCL9 were treated with vehicle or SAH-BCL9 peptides (5 µM) and dual luciferase assays were performed at 24 h. The suppression of reporter activities by SAH-BCL9$_B$ is dose-responsively reversed by increasing BCL9 protein expression, highlighting the on-target specificity of SAH-BCL9$_B$-based inhibition of β-catenin/BCL9-driven transcription. *P<0.01. HCT116 cells were employed in this assay due to their relatively low level expression of endogenous BCL9.

HCT116 cells were transfected with pOT-Luc plasmid or a control UbC-Luc plasmid. The HCT116-pOT-Luc cells were implanted into mice (n=2) on the left flank and the constitutive UbC-Luc control cells on the right flank. Animals underwent baseline imaging, followed by SAH-BCL9$_B$ or SAH-BCL9$_B$(R359E) injection and serial imaging at the indicated time points. The pOT-Luc reporter activity was normalized to UbC-Luc activity. See results in FIG. 9.

Example 14. VEGF ELISA

VEGF ELISA was performed as previously described (Mani, M. et al. Cancer Res 69, 7577-86 (2009)). Briefly, cells (1×10$^6$) were treated with vehicle and SAH-BCL9 peptides (5 µM) for 24 h. VEGF levels in the supernatant were then measured according to the manufacturer's ELISA protocol (DuoSet, R&D Systems).

Example 15. Chromatin Immunoprecipitation (ChIP) and Polymerase Chain Reaction (PCR)

Figure 11A:
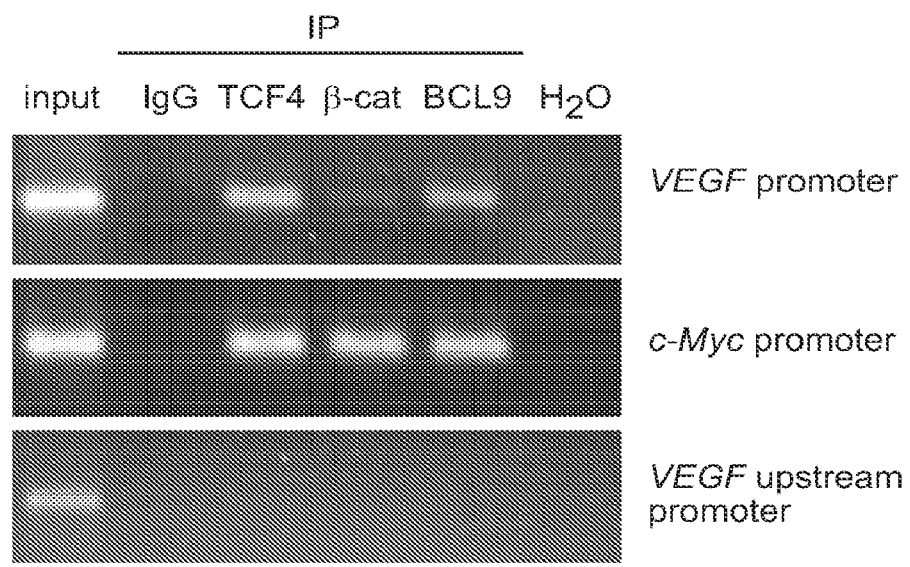
FIG. 11A-FIG. 11B show that VEGF is a direct transcriptional target of BCL9.

Antibody (3 µg) was prebound for 8 h to protein A and protein G Dynal magnetic beads (Dynal Biotech, Norway) and washed 5 times with ice-cold PBS containing 5% BSA, and then added to the diluted chromatin for overnight immunoprecipitation using the following antibodies: TCF-4 (Upstate #05-511), mouse IgG2a isotype control (Sigma, M5409), and rabbit IgG (sc-2027, Santa Cruz). The magnetic bead-chromatin complexes were collected and washed 6× in RIPA buffer (50 mM HEPES [pH 7.6], 1 mM EDTA, 0.7% Na deoxycholate, 1% NP-40, 0.5 M LiCl). DNA was eluted from the beads as previously described (Clevers, H. Cell 127, 469-80 (2006)). Amplification was carried out with a PTC-200 programmable thermal controller (MJ Research) after an initial denaturation at 94° C. for 5 min, followed by 30 cycles of PCR using the following temperature and time profile: denaturation at 94° C. for 0.5 min, primer annealing at 59° C. for 0.5 min, primer extension at 72° C. for 0.5 min, and a final extension of 72° C. for 10 min. The PCR products were visualized by 2% gel electrophoresis. The following promoter primer sets were employed: (1) VEGF: F (Forward): 5'-gcgtgtctctggacagagttt-3' (SEQ ID NO: 116) and R (Reverse): 5'-agcctcagccctccaca-3'(SEQ ID NO: 117); (2) VEGF upstream: F: 5'-gaggctatgccagctgtagg-3'(SEQ ID NO: 118) and R: 5'-ccctttctcctccaactctcc-3'(SEQ ID NO: 119); (3) c-Myc: F: 5'-actccccggctcggtccacaagc-3', (SEQ ID NO: 120) and R: 5'-cccaatttctcagccaggtttcag-3' (SEQ ID NO: 121) (Klaus, A. & Birchmeier, W. Nat Rev Cancer 8, 387-98 (2008)). See results in FIG. 11A.

Example 16. VEGF Promoter Luciferase Assays

Figure 11B:
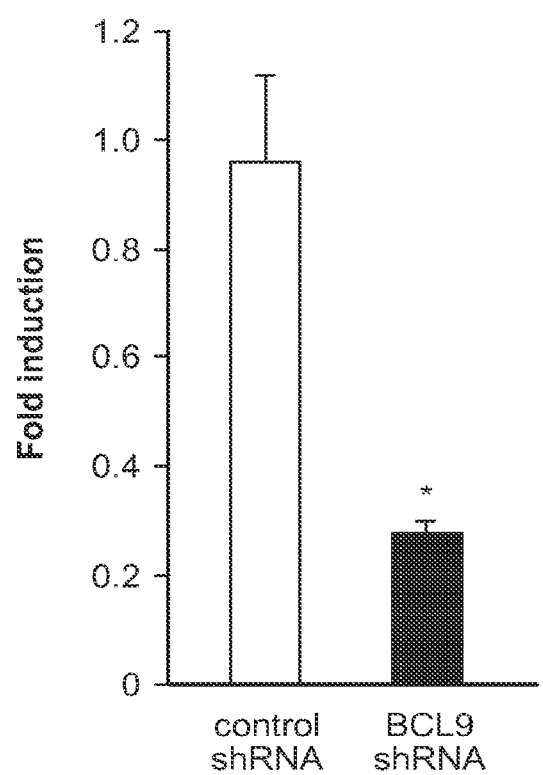
Figure 12:
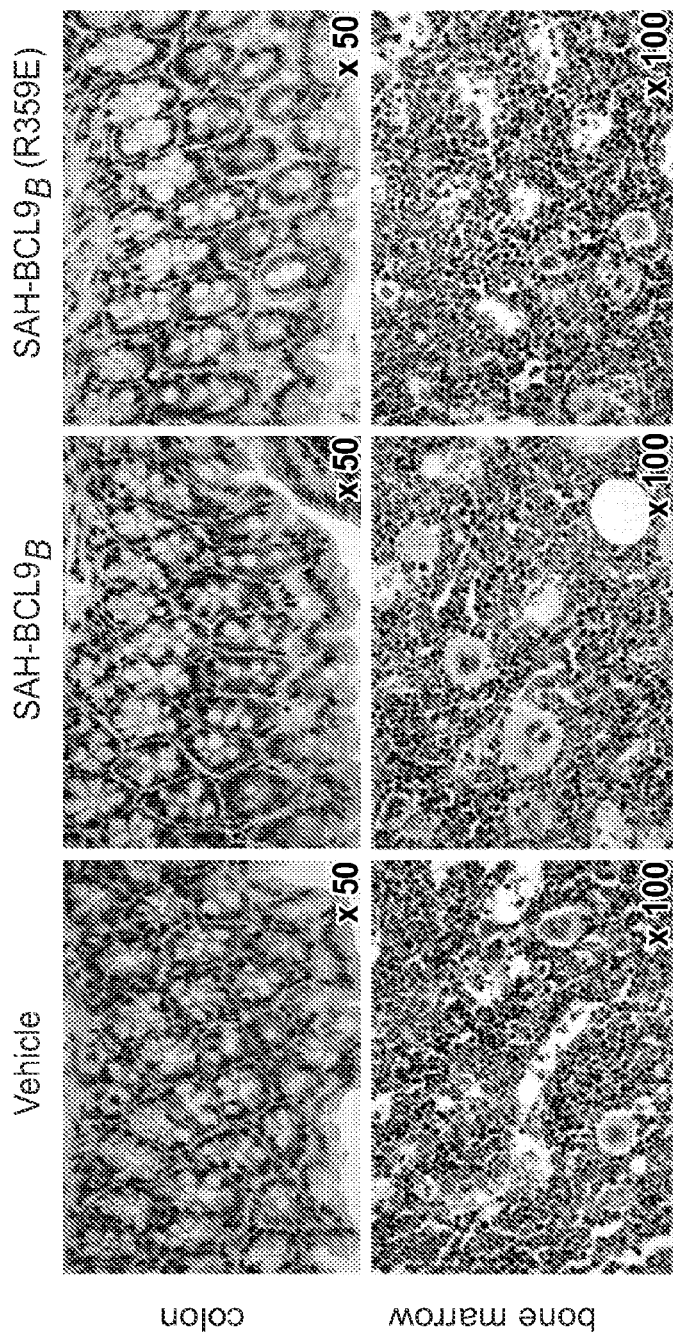
FIG. 12 shows normal appearance of colonic mucosa and bone marrow in SAH-BCL9-treated mice. H&E staining of colonic mucosa and bone marrow tissues isolated from experimental mice treated with vehicle or SAH-BCL9-peptides showed no evidence of toxicity across all histologic specimens.
Figure 13A:
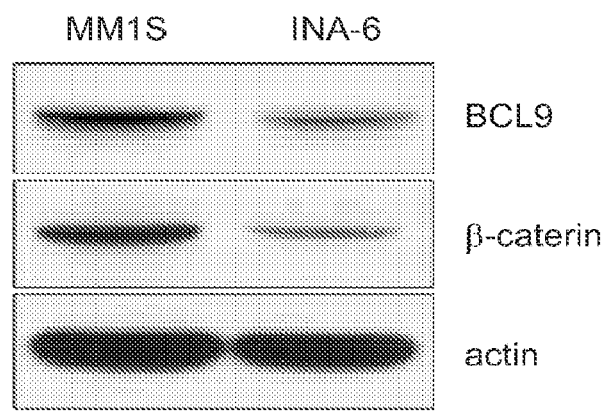
FIG. 13A-FIG. 13B show that SAH-BCL9$_B$ inhibits the proliferation of INA-6 multiple myeloma cells.
Figure 13B:
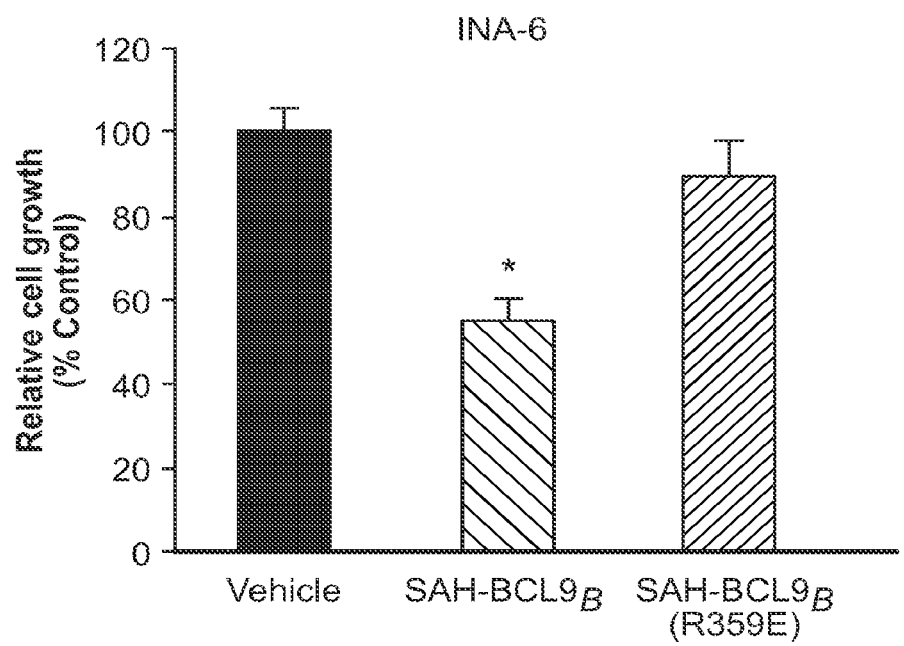

The VEGF promoter-driven luciferase constructs (2.6-kb) were a kind gift from Soumitro Pal (Transplantation Research Center, Children's Hospital Boston and Brigham and Women's Hospital) (Basu, A. et al. Cancer Res 68, 5689-98 (2008)). Cells were transfected with the VEGF luciferase constructs using FuGENE transfection reagent (Roche) and luciferase activity was measured using Dual Luciferase Reporter Assay System (Promega) as previously described (Sukhdeo, K. et al. Proc Natl Acad Sci USA 104, 7516-21 (2007)). See results in FIG. 11B.

Example 17. Lentiviral Vectors

Figure 10:
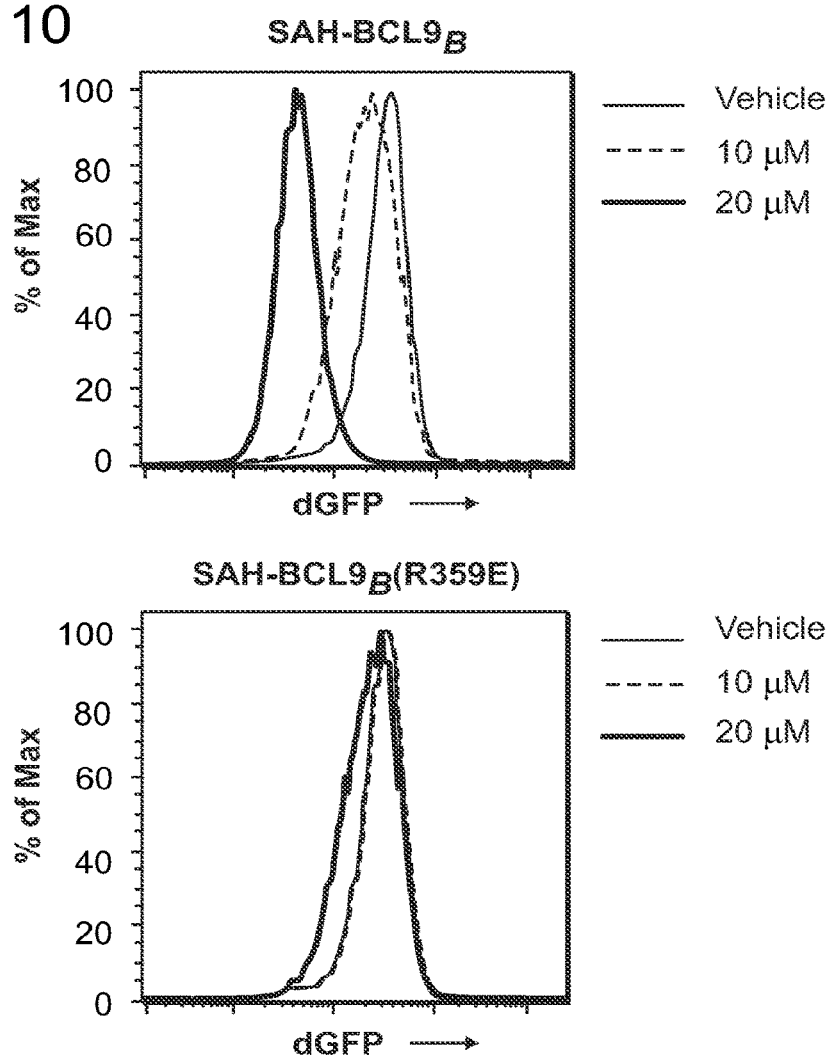
FIG. 10 shows inhibition of Wnt-specific transcriptional reporter activity by SAH-BCL9$_B$. SAH-BCL9$_B$ dose-responsively blocked dGFP expression under the transcriptional control of TCF regulatory sequences (7×TdG) in Colo320 cells. In contrast, treatment with SAH-BCL9$_B$ (R359E) had little to no effect.

A lentiviral reporter vector containing seven TCF/LEF-1 binding motifs and a minimal promoter driving destabilized GFP expression (7×TdG) was derived from the lentiviral vector TOP-dGFP, which contains three TCF/LEF-1 binding motifs (Sukhdeo, K. et al. Proc Natl Acad Sci USA 104, 7516-21 (2007)). Two synthetic complementary oligonucleotides (IDT-DNA) with four TCF/LEF-1 binding motifs (GATCAAAGG) were designed to generate compatible overhanging ends for annealing to an Xba1 restriction site. The oligonucleotides were annealed by heating to 95° C. and slow cooling to room temperature, followed by ligating into the Xba1-linearized TOP-dGFP vector, yielding 7×TdG. For construction of the control vector carrying seven FOP-sites (7×FdG), the 7×TOP cassette was removed from the 7×TdG vector by restriction digesting with Xma1 and Age1. A synthetic cassette carrying seven FOP sites (GGC-CAAAGG) but otherwise identical to the removed 7×TOP cassette was inserted, yielding 7×FdG. BCL9 shRNA and control shRNA lentiviral vectors were generated as reported (Sampietro, J. et al. Mol Cell 24, 293-300 (2006)). See results in FIG. 10, FIG. 11B.

Example 18. Lentivirus Production and Infection

HEK293T cells were plated in 10 cm tissue culture dishes and co-transfected with 10 μg lentiviral vector (either 7×TdG or 7×FdG), 10 μg pCMV-dR8.91 and 2 μg pMD2.G (Naldini et al, PNAS, 1996) using 60 μL LipoD293 (Signagen) according to the manufacturer's protocol. The media was replaced after 12 h with 30% FCS containing DMEM (Gibco) and conditioned for 36 h. Conditioned medium was then filtered through 0.45 μm syringe filters (Millipore), mixed 1:1 with fresh DMEM, and then directly used for infection of cultured Colo320 (ATCC) cells. Polybrene (Sigma) was added to a final concentration of 8 μg/mL to enhance the efficiency of infection. Lentivirus shRNA infections to knockdown BCL9 expression were performed as described previously (Logan, C. Y. & Nusse, R. Annu Rev Cell Dev Biol 20, 781-810 (2004)). Briefly, recombinant BCL9 shRNA and control lentiviruses were produced by transient transfection of 293T cells. Colo320 were transduced with virus supernatant containing polybrene, and GFP-expressing cells sorted by FACS. See results in FIG. 10, FIG. 11B.

Example 19. Establishment of Single Cell Cultures

Colo320 cells were subjected to infection for 72 h with either 7×TdG or 7×FdG lentivirus, and the transduced and control non-transduced cells were trypsinized, washed, and then analyzed on a FACSaria flow sorter. Hoechst 33258 staining was used to exclude dead cells. Single GFP-positive Colo320-7×TdG cells were sorted into 96 well plates using stringent gating on forward/side scatter height and width to exclude doublets. The presence of a single cell per well was confirmed microscopically after sorting and then single cell cultures were expanded for subsequent use. See results in FIG. 11B.

Example 20. Chromatin Immunoprecipitation

Three micrograms of antibody was prebound for 8 h to protein A and protein G Dynal magnetic beads (Dynal Biotech, Norway) and washed 5× with ice-cold PBS containing 5% BSA, and then added to the diluted chromatin for overnight immunoprecipitation using the following antibodies: TCF-4 (Upstate #05-511), mouse IgG2a isotype control (Sigma, M5409), and rabbit IgG (sc-2027, Santa Cruz). The magnetic bead-chromatin complexes were collected and washed 6× in RIPA buffer (50 mM HEPES [pH 7.6], 1 mM EDTA, 0.7% Na deoxycholate, 1% NP-40, 0.5 M LiCl). DNA was eluted from the beads as previously described (Shang, Y., et al. Cell 103, 843-52 (2000)). Amplification was carried out with a PTC-200 programmable thermal controller (MJ Research) after an initial denaturation at 94° C. for 5 min, followed by 30 cycles of PCR using the following temperature and time profile: denaturation at 94° C. for 0.5 min, primer annealing at 59° C. for 0.5 min, primer extension at 72° C. for 0.5 min, and a final extension of 72° C. for 10 min. The PCR products were visualized by 2% gel electrophoresis. The following promoter primer sets were employed: (1) VEGF$^B$: F (Forward): 5'-gcgtgtctctggacagagttt-3' (SEQ ID NO: 116) and R (Reverse): 5'-agcctcagcccttccaca-3'(SEQ ID NO: 117); (2) VEGF upstream: F: 5'-gaggctatgccagctgtagg-3'(SEQ ID NO: 118) and R: 5'-ccctttcctccaactctcc-3' (SEQ ID NO: 119); (3) c-Myc: F: 5'-actcccccggctcggtccacaagc-3' (SEQ ID NO: 120), and R: 5'-cccaatttctcagccaggtttcag-3' (SEQ ID NO: 121). See results in FIG. 11A.

Example 21. Reporter Assays

Luciferase activity was measured using the Dual Luciferase Reporter Assay System (Promega) as previously described (Sukhdeo, K. et al. Proc Natl Acad Sci USA 104, 7516-21 (2007)). To measure Wnt or NFκB reporter activity, Colo320 cells were transfected with TOP-FLASH, FOP-FLASH plasmid (Millipore Corporation) or NFκB luciferase reporter (Stratagene), along with an internal *Renilla* control plasmid (hRL-null). Transfection was accomplished using FuGENE (Roche) according to the manufacturer's protocol. The results were normalized to control *Renilla* activity. The reported data represent the average of three independent transfection experiments performed in triplicate. See results in FIG. 9, FIG. 10.

Example 22. Selective Dissociation of the BCL9/β-Catenin Complex by SAH-BCL9$_B$ To evaluate binding by ELISA, glutathione microtiter plates (Pierce) were incubated with 50 ng recombinant GST-β-catenin in 100 μL of ELISA buffer (PBS, 1% BSA, 0.05% Tween-20) per well and rotated (200 rpm) at 37° C. for 1 hr, followed by 4-cycles of automated plate-washing with PBS, 0.05% Tween-20. Two-fold serial dilution of FITC-conjugated peptides in ELISA buffer were prepared in a separate 96-well plate and transferred (100 μL) to the β-catenin-bound plate. The experimental plate was incubated for 2 hr at 37° C. (200 rpm), subjected to automated plate washing, and then 100 μL of a 1:7500 dilution of anti-FITC-conjugated HRP in ELISA buffer was transferred to each well for an additional 1 hr incubation at 37° C. (200 rpm), followed by automated plate washing. Wells were developed by adding 50 μL of tetramethylbenzidine (TMB) solution, incubating at room temperature for 20 min, and then stopping the reaction with 50 μL of 2 M H2SO4. The absorbance at 450 nm was read on a microplate reader (Molecular Devices) and the binding isotherms plotted and EC50 values determined by nonlinear regression analysis using Prism software (GraphPad). Binding assays were performed in triplicate and repeated at least twice with freshly prepared recombinant proteins. Consistent with the reduced capacity of FITC-SAH-BCL9$_{MUT}$ (SAH-BCL9$_B$ (R359E)) to immunoprecipitate native β-catenin (see FIG. 1H), R359E point mutagenesis caused a 5-fold decrease in direct binding activity to recombinant β-catenin protein. See results in FIG. 17A.

To evaluate the capacity of SAH-BCL9 to disrupt pre-formed BCL9/β-catenin complexes, the biological activity required for Wnt signaling blockade, recombinant human BCL9 (residues 243-469) cloned into pET-23a (+) vector containing carboxy-terminal hexa-histidine tag (SEQ ID NO: 141) (His-BCL9) and full-length human β-catenin cloned into pGEX-4T-1 vector with an amino-terminal glutathione-S-transferase (GST) tag (recombinant GST-β-catenin) were expressed and purified as previously reported (J. Sampietro et al., Mol Cell 24, 293 (2006)). Equal amounts (1 nM) of His-tagged BCL9 and GST-tagged β-catenin bound to glutathione-Sepharose 4B beads (GE) were incubated overnight at 4° C. in assay buffer (100 mM Na$_2$PO$_4$ [pH7.4], 100 µg/mL bovine serum albumin, 0.01% Triton X-100 and 4% DMSO). Complexes of His-tagged BCL9 bound to bead-immobilized GST-tagged β-catenin were isolated by centrifugation, resuspended in 1 mL of assay buffer, and 50 µL of slurry incubated in the presence or absence of SAH-BCL9$_B$ or SAH-BCL9$_{MUT}$ (SAH-BCL9$_B$(R359E)) in 500 µl assay buffer for 2 hr at room temperature. Glutathione bead-bound proteins were washed twice by centrifugation, eluted, and resolved by gel electrophoresis. GST-β-catenin was detected by Coomassie blue staining and the presence of retained His-BCL9 was detected by immunoblot analysis (anti-His 23655, Cell Signaling) and quantified using ImageJ software (rsbweb.nih.gov/ij). The experiment was repeated three times with similar results. The results demonstrated that SAH-BCL9$_B$ could dose-responsively dissociate the complex with an IC$_{50}$ of 135 nM, whereas single point mutagenesis reduced the activity by 6-fold. See results FIG. 17B.

Example 23. SAH-BCL9$_B$ Inhibits Wnt Transcriptional Activity

To measure the effects of vehicle, SAH-BCL9$_B$, and SAH-BCL9$_{MUT}$ on the expression of Wnt/β-catenin target genes, including VEGF, in Colo320 (FIG. 18) and MM1S (FIG. 19) cell lines, quantitative PCR (qRT-PCR) analysis was performed. RNA was extracted with TRIzol Reagent (Invitrogen) according to the manufacturer's protocol. Total RNA (2 µg) was reverse transcribed (SuperScript VILO cDNA synthesis kit, Invitrogen) and qPCR was performed using an Applied Biosynthesis 7500 Real-time PCR system. PCR primers were designed as below:

```
FOXQ 1:
                                        (SEQ ID NO: 122)
cgcggactttgcactttgaa;

(SEQ ID NO: 123)
agctttaaggcacgtttgatggag

CDK4:
                                        (SEQ ID NO: 124)
atgttgtccggctgatgga;

(SEQ ID NO: 125)
caccagggttaccttgatctcc
```

```
Axin2:
                                        (SEQ ID NO: 126)
cggaaactgttgacagtggat;

(SEQ ID NO: 127)
ggtgcaaagacatagccagaa

VEGF:
                                        (SEQ ID NO: 128)
catgaactttctgctgtcttgg;

(SEQ ID NO: 129)
atgattctgccctcctcctt

LGR5:
                                        (SEQ ID NO: 130)
ctcccaggtctggtgtgttg;

(SEQ ID NO: 131)
gtgaagacgctgaggttgga

CMYC:
                                        (SEQ ID NO: 132)
tttttcgggtagtggaaaacc;

(SEQ ID NO: 133)
gcagtagaaatacggctgcac

CD44:
                                        (SEQ ID NO: 134)
tttgcattgcagtcaacagtc;

(SEQ ID NO: 135)
tgagtccacttggctttctgt

CLDN2:
                                        (SEQ ID NO: 136)
cggtgtggctaagtacaggc;

(SEQ ID NO: 137)
caaagctcacgatggtggtct

LEF-1:
                                        (SEQ ID NO: 138)
catcccttcctcattccttcaac;

(SEQ ID NO: 139)
aggcttcctaaaaggtggtgg
```

Figure 18A:
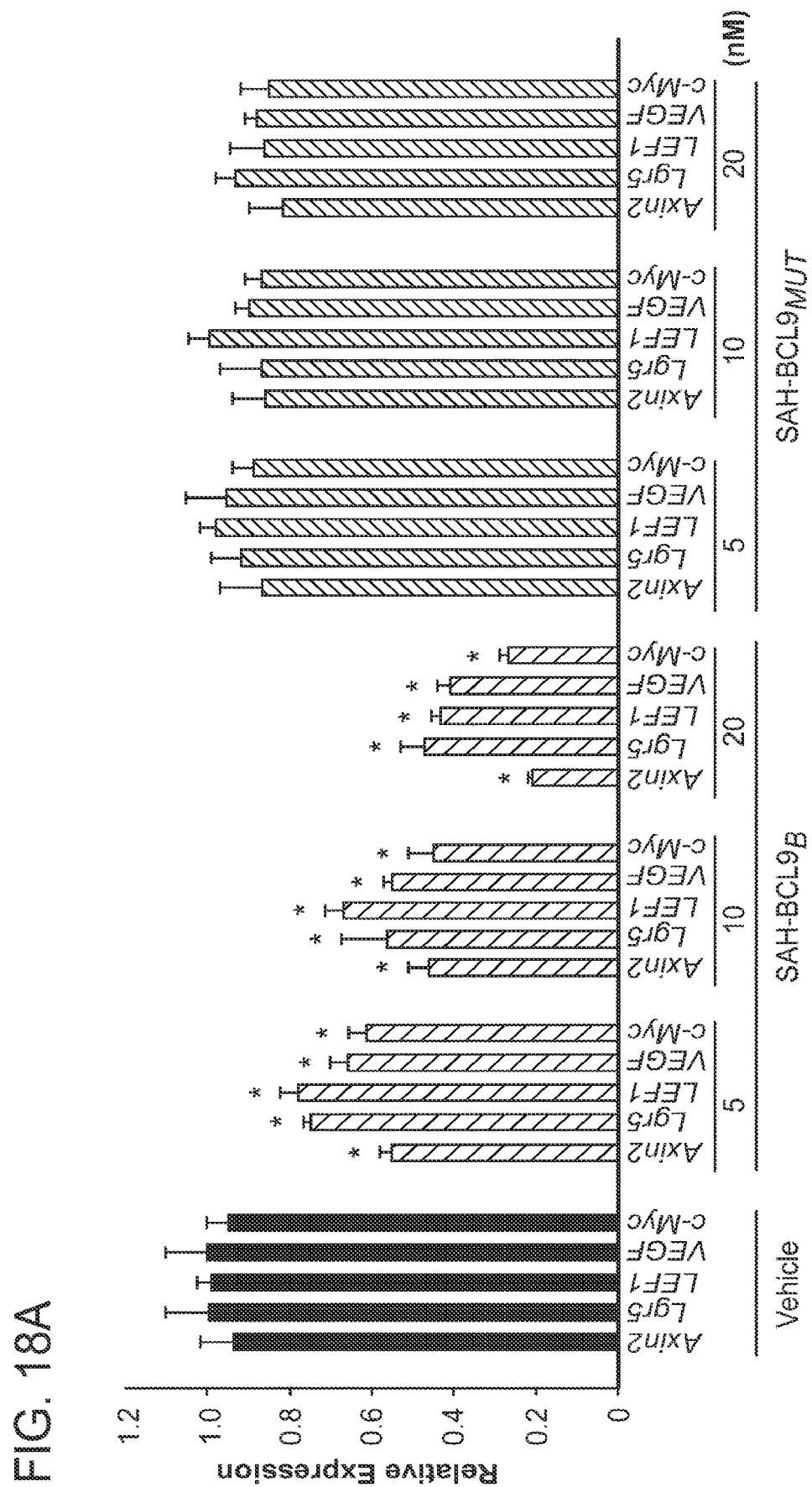
Figure 18B:
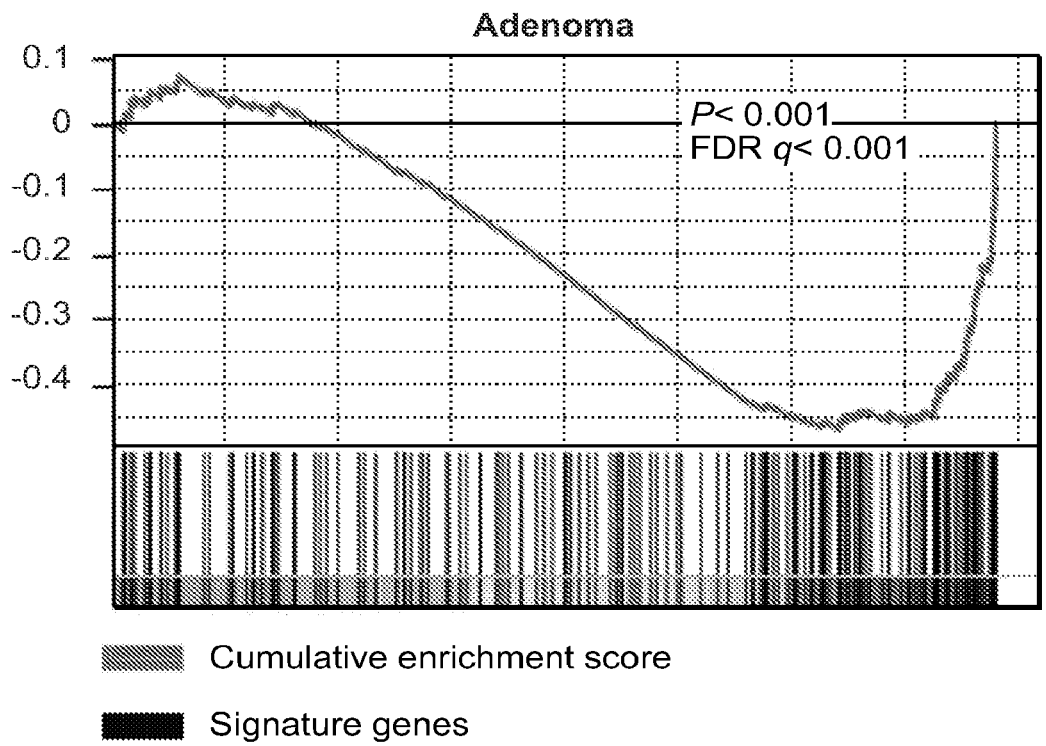
Figure 18C:
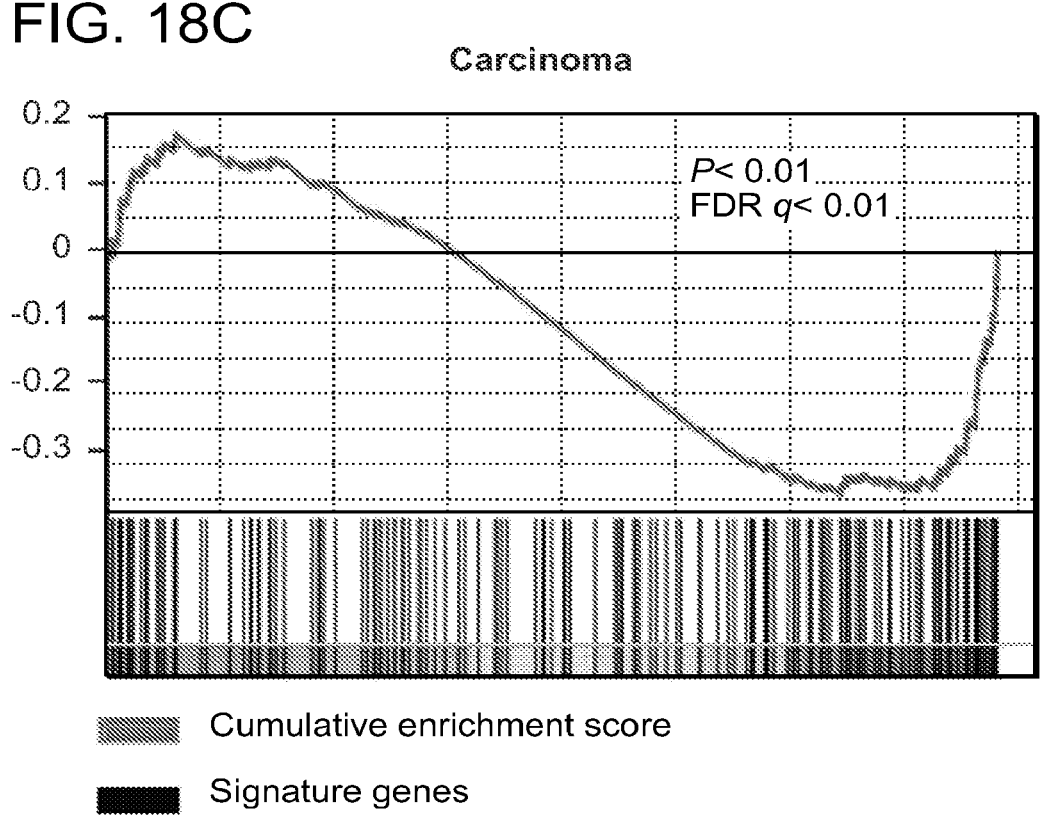
Figure 19A:
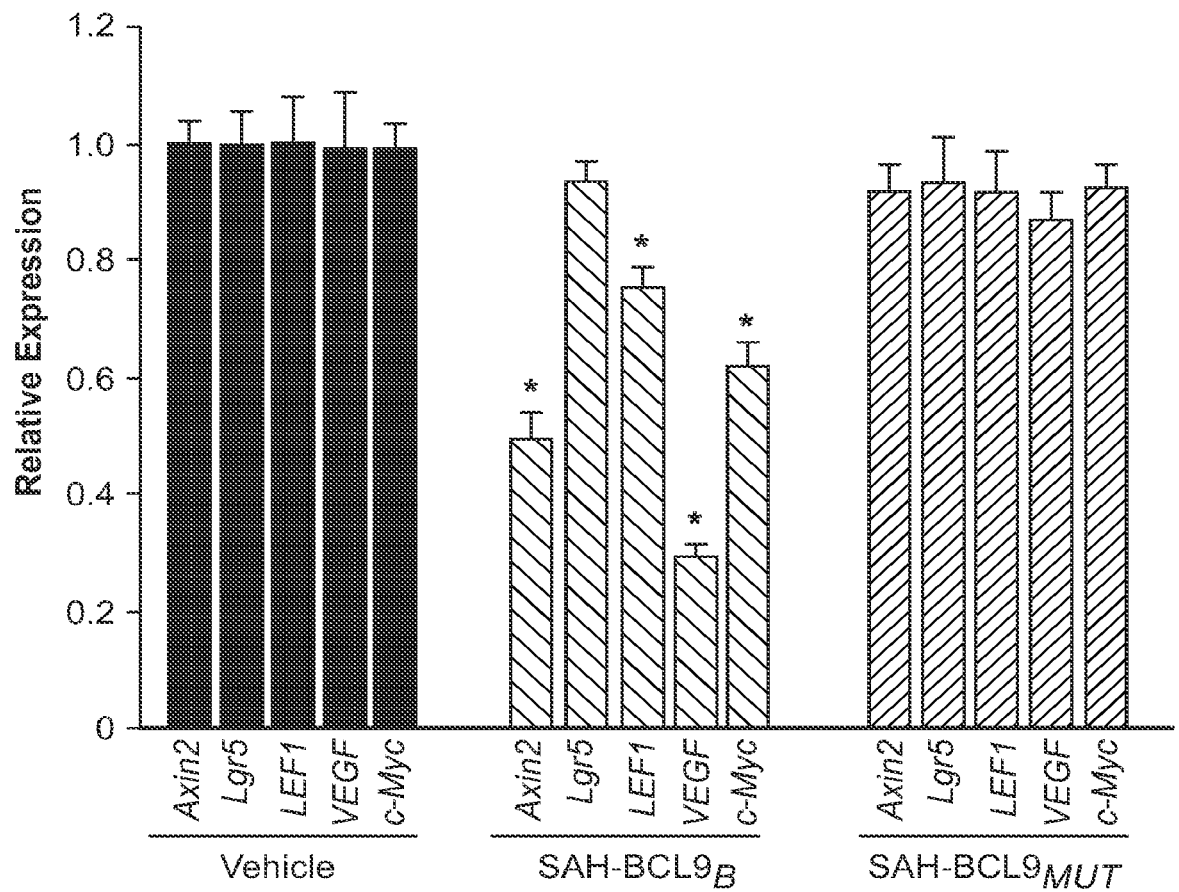
FIG. 19A-FIG. 19B show the suppression of Wnt target gene expression by SAH-BCL9$_B$.
Figure 19B:
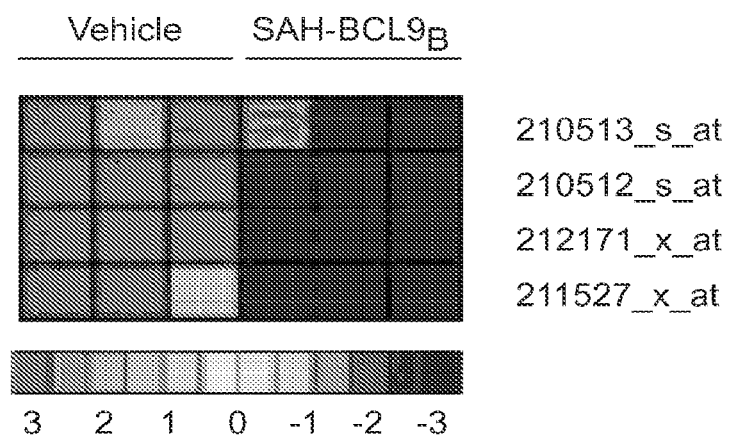
Figure 20A:
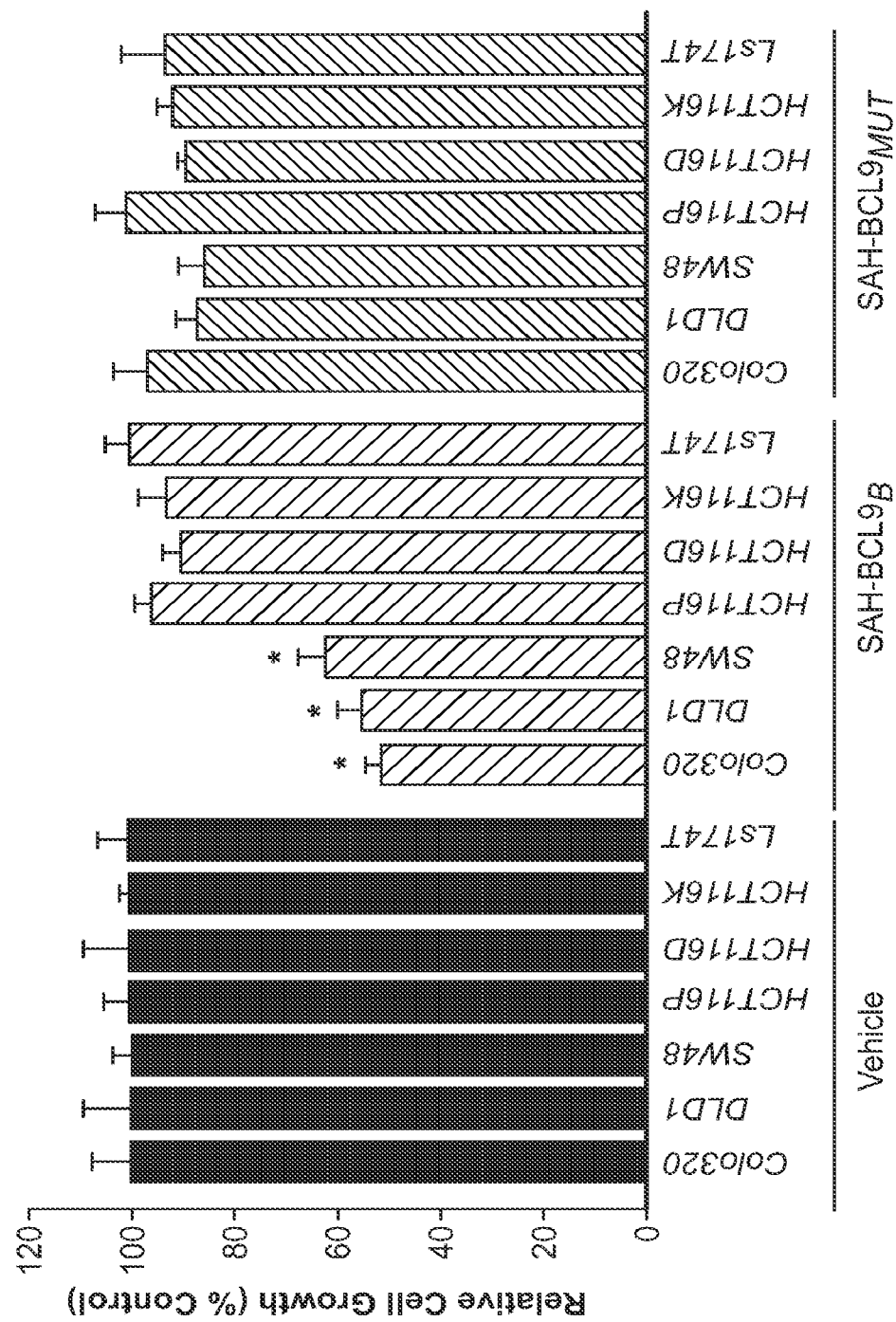
FIG. 20A-FIG. 20B show that SAH-BCL9$_B$ selectively inhibits proliferation of cultured colon cancer cells that are driven by pathologic Wnt signaling and express BCL9.
Figure 20B:
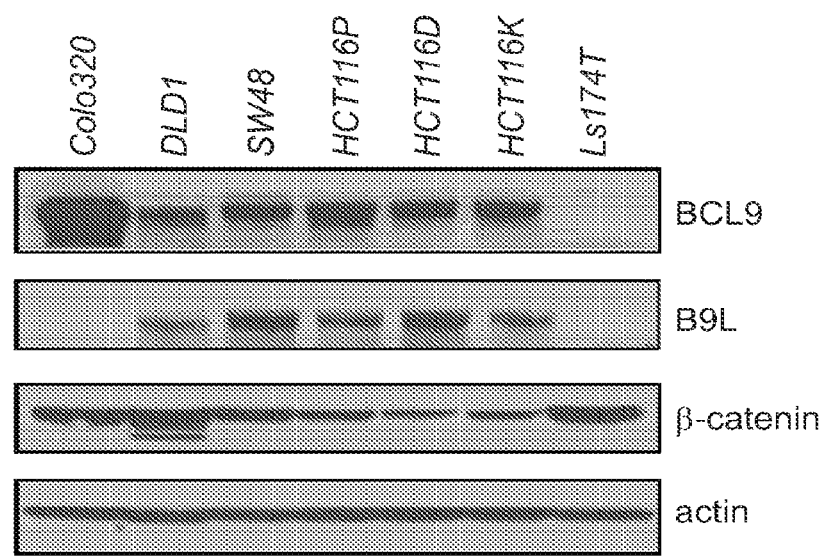

Analysis of target genes was conducted in quadruplicate using POWER SYBR Green Master Mix (Applied Biosystems) as previously described (M. Mani et al., Cancer Res 69, 7577 (2009)). Transcripts levels were normalized to β-actin expression. These experiments were repeated three times. Treatment with SAH-BCL9$_B$, but not vehicle or SAH-BCL9$_{MUT}$, dose-responsively reduced the mRNA levels of VEGF, c-MYC, LGR5, LEF1, and AXIN2 (FIG. 18A and FIG. 19A). Actin, a non-Wnt pathway target gene, was used as a reference in Colo320 cells and showed no change in response to SAH-BCL9$_B$ treatment (FIG. 18A). LGR5 was reduced in Colo320 cells but not in MM1S cells, consistent with the cellular specificity of Wnt target gene transcription.

To further investigate the specificity of SAH-BCL9$_B$ in blocking Wnt transcriptional activity, comparative genome-wide expression analyses of Wnt target genes in the DLD1 colon cancer cell line, for which a Wnt transcription pathway signature has been described (L. G. Van der Flier et al., Gastroenterology 132, 628 (2007)), was performed. RNA from triplicate SAH-BCL9$_B$- and vehicle-treated DLD1 samples (10 µM each for 12 hours) was isolated for gene expression profiling analyses. Affymetrix Human U133 Plus 2.0 arrays were processed using the function of the affy Bioconductor package (URL http://www.R-project.org.). Gene sets were compiled from Van der Flier et al. and gene set enrichment and statistical analyses performed using GSEA software (http://www.broad.mit.edu/GSEA) and a two-tailed t-test, respectively. Microarray data has been deposited in the Gene Expression Omnibus (http://www.ncbi.nlm.nih.gov/geo) and comply with MIAME annotation standards.

Figure 18F:
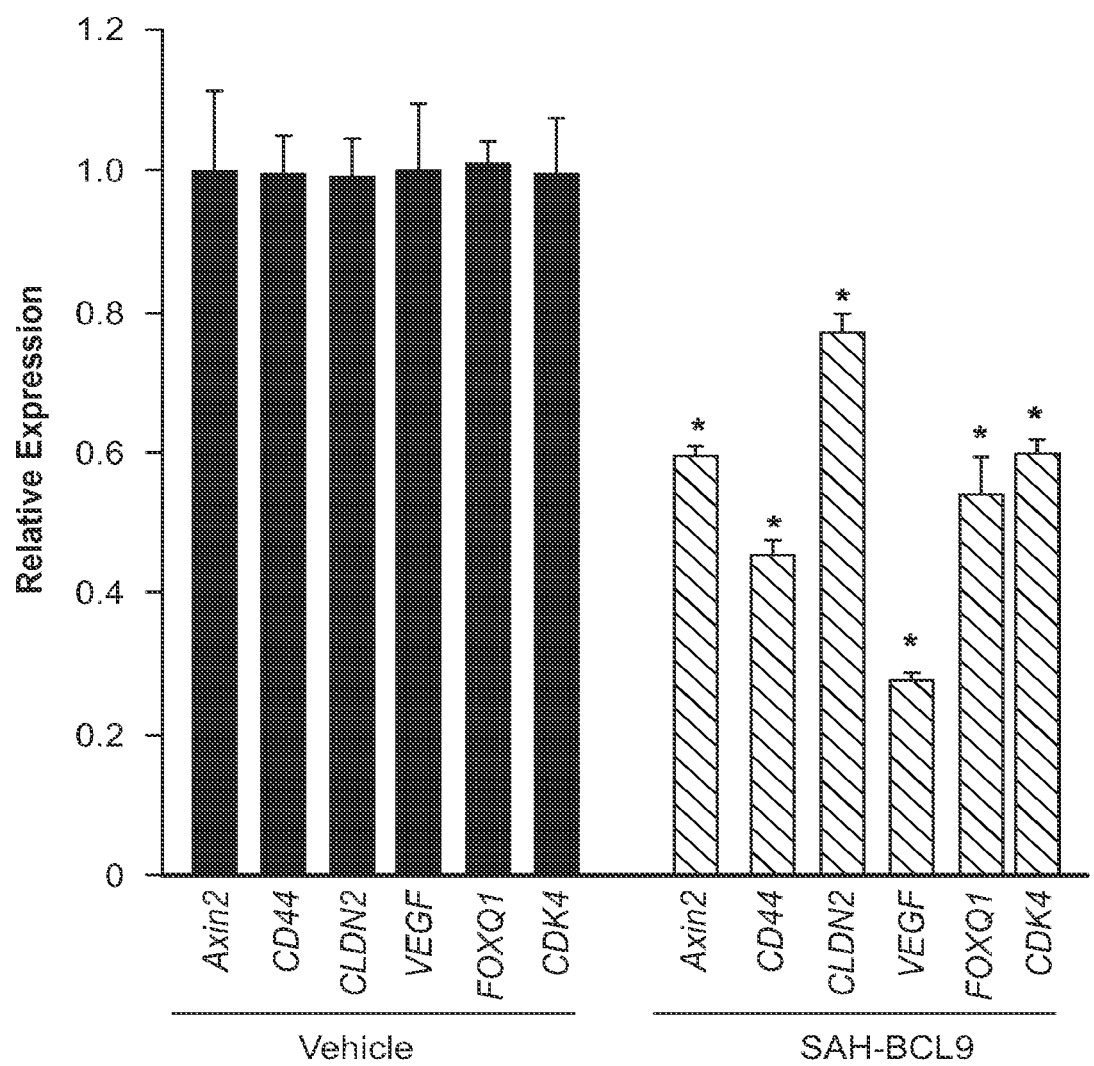

The triplicate data sets from SAH-BCL9$_B$- and vehicle-treated DLD1 generated using Affymetrix oligonucleotides microarrays were compared with published gene expression data from DLD1 cells bearing inducible dominant-negative forms of TCF1 and TCF4 (L. G. Van der Flier et al., Gastroenterology 132, 628 (2007)). Gene set enrichment analysis (GSEA) revealed a strong and statistically significant correlation between the genes down-regulated by SAH-BCL9$_B$ and the dominant-negative forms of TCF1 and TCF4 in both adenoma (FIG. 18B, family-wise error (FWER) p-value<0.001; false discovery rate (FDR) q-value<0.001) and carcinoma (FIG. 18C FWER and FDR<0.01), highlighting the specificity of SAH-BCL9$_B$ in blocking Wnt transcriptional activity. Axing, a robust and specific Wnt target gene(3), was among the most down-regulated genes by SAH-BCL9$_B$ treatment, in addition to other Wnt targets involved in cell metastasis (CD44, CLDN2), cell proliferation (CyclinA2, CDK4), and EMT (FOXQ1) (FIG. 18D and FIG. 18E). These findings were then validated by qRT-PCR (FIG. 18F). VEGF-A was among the genes downregulated in cells treated with SAH-BCL9$_B$ (FIG. 18F and FIG. 19), linking the β-catenin/BCL9 complex to tumor-induced angiogenesis.

Example 24. Combination Therapies

Figure 21A:
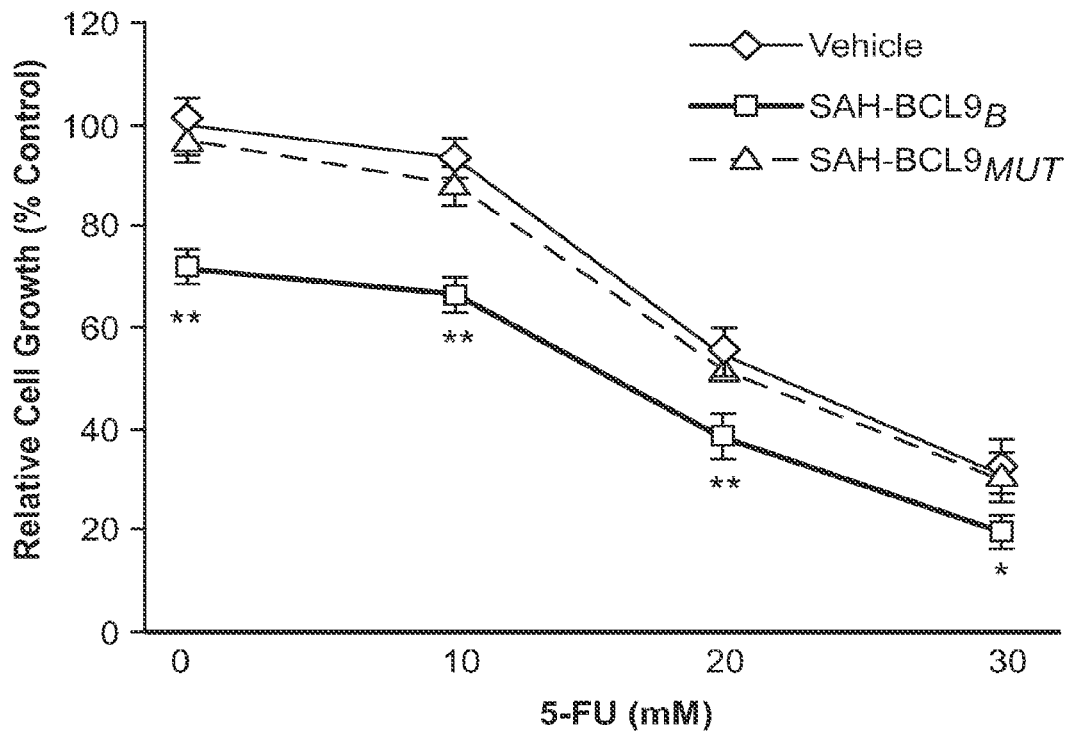
FIG. 21A-FIG. 21B show that SAH-BCL9$_B$ enhances the cytotoxic effect of conventional chemotherapeutic agents.
Figure 21B:
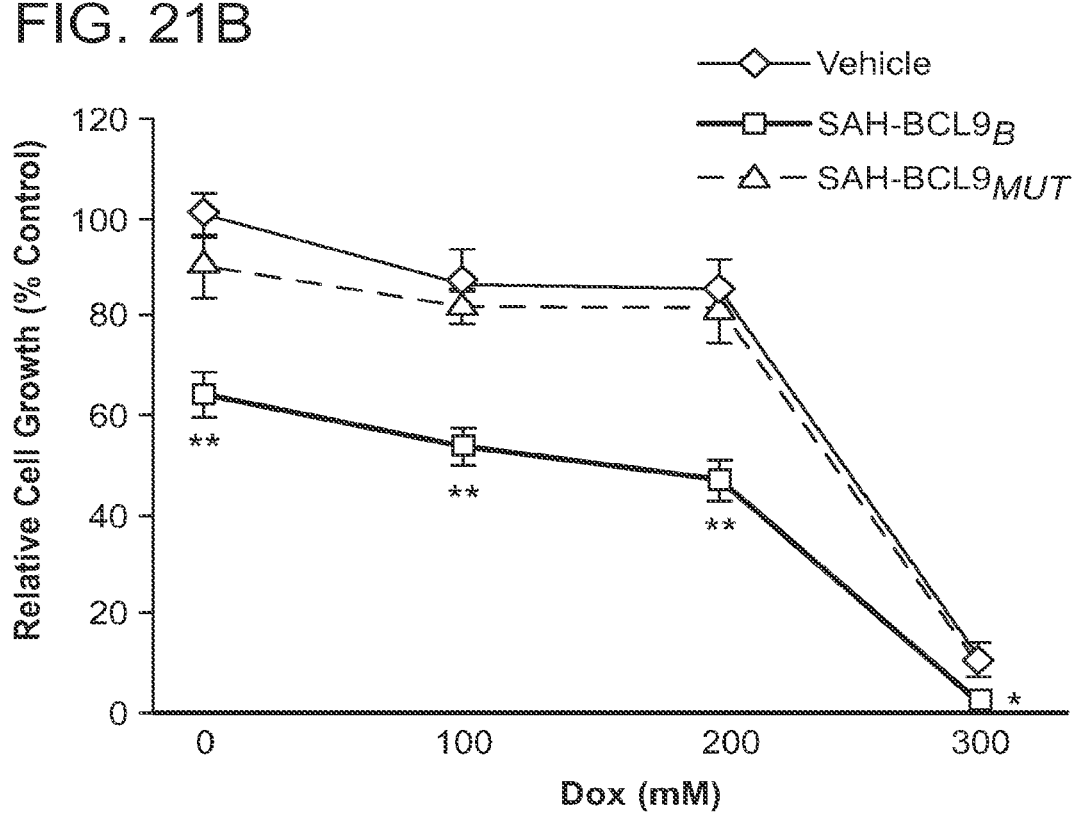

To test whether the anti-proliferative effect of SAH-BCL9$_B$ could synergize with other agents commonly used to treat MM or CRC, combination treatment studies were conducted. Indeed, the cytotoxic effects of 5-fluorouracil on CRC cells and of doxorubicin on MM cells were enhanced by SAH-BCL9$_B$, but not by vehicle or the mutant peptide. See results in FIG. 21.

INCORPORATION BY REFERENCE

The contents of all references (including literature references, issued patents, published patent applications, co-pending patent applications, and GenBank numbers) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A method of treating cancer mediated by BCL9/β-catenin binding in a human subject, the method comprising administering to the human subject a therapeutically effective amount of a structurally constrained peptide of an HD2 domain of BCL9 (BCL9-HD2) comprising at least one hydrocarbon staple, wherein the at least one hydrocarbon staple links the side chain of a first non-natural amino acid that replaces a first BCL9-HD2 amino acid selected from the group consisting of Leu-351, Ser-352, Gln-353, Glu-354, Gln-355, His-358, Arg-359, Arg-361, Ser-362, Leu-363, Thr-365, Leu-366, Ile-369, Gln-370, Met-372, Leu-373, and Phe-374 with the side chain of a second non-natural amino acid that replaces a second BCL9-HD2 amino acid selected from the group consisting of Leu-351, Ser-352, Gln-353, Glu-354, Gln-355, Leu-356, Glu-357, His-358, Arg-359, Glu-360, Arg-361, Ser-362, Leu-363, Thr-365, Leu-366, Arg-367, Asp-368, Ile-369, Gln-370, Arg-371, Met-372, Leu-373, and Phe-374, wherein the first and second non-natural amino acids are two, three, or six amino acids apart, and wherein the cancer is selected from the group consisting of colorectal cancer, colon cancer, and multiple myeloma.

2. The method of claim 1, wherein the human subject has been previously identified as in need of a canonical Wnt/β-catenin signaling inhibitor to treat the cancer.

3. The method of claim 1, wherein the human subject is administered with an additional therapeutic agent, radiation, or chemotherapy.

4. The method of claim 3, wherein the additional therapeutic agent is an anti-cancer compound.

5. The method of claim 3, wherein the structurally constrained peptide and the additional therapeutic agent are administered simultaneously or sequentially.

6. The method of claim 1, wherein the structurally constrained peptide comprises an interacting face comprised of amino acids that interact with β-catenin, wherein the interacting face comprises BCL9 residues Gln-355, His-358, Arg-359, Ser-362, Leu-363, Leu-366, Ile-369, Gln-370, Leu-373, and Phe-374.

7. The method of claim 6, wherein the interacting face represents a single face of an α-helix.

8. The method of claim 7, wherein the single face of a helix comprises one, two, three, or four adjacent stacked columns of amino acids, wherein the stacked columns of amino acids are defined by positions a, d, and g; positions b and e; or positions c and f; in an alpha helix having 3.6 amino acids per turn wherein the amino acids are consecutively and serially assigned positions a-g; and positions a and d; positions b and e; or positions c and f in a $3_{10}$ helix having 3 amino acids per turn wherein the amino acids are consecutively and serially assigned positions a-f; or homologues thereof.

9. The method of claim 1, wherein the at least one hydrocarbon staple is formed by an olefin metathesis reaction.

10. The method of claim 1, wherein the first and second non-natural amino acids are selected from the following:

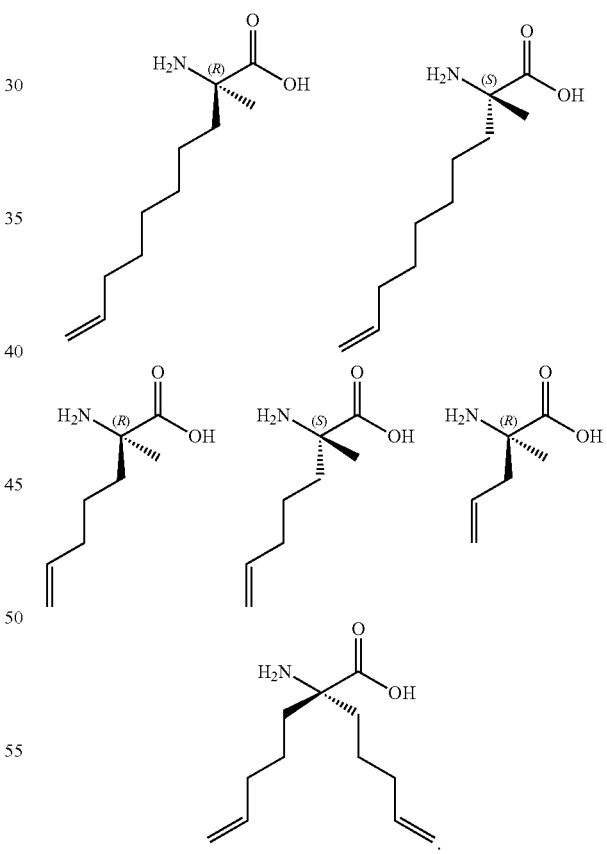

11. The method of claim 1, wherein the structurally constrained peptide comprises 1 to 2 staples within the BCL9 HD2 peptide.

12. The method of claim 1, wherein the at least one hydrocarbon staple is located at any of the staple positions in any one of the following BCL9 HD2 stapled peptides:

i, i + 4 single staples:

(SEQ ID NO: 8)
XSQEXLEHRERSLQTLRDIQRBLF (SEQ ID NO: 9)
LXQEQXEHRERSLQTLRDIQRBLF (SEQ ID NO: 10)
LSXEQLXHRERSLQTLRDIQRBLF (SEQ ID NO: 11)
LSQXQLEXRERSLQTLRDIQRBLF (SEQ ID NO: 12)
LSQEXLEHXERSLQTLRDIQRBLF (SEQ ID NO: 13)
LSQEQXEHRXRSLQTLRDIQRBLF (SEQ ID NO: 14)
LSQEQLXHREXSLQTLRDIQRBLF (SEQ ID NO: 15)
LSQEQLEXRERXLQTLRDIQRBLF (SEQ ID NO: 16)
LSQEQLEHXERSXQTLRDIQRBLF (SEQ ID NO: 17)
LSQEQLEHRXRSLXTLRDIQRBLF (SEQ ID NO: 18)
LSQEQLEHREXSLQXLRDIQRBLF (SEQ ID NO: 19)
LSQEQLEHRERXLQTXRDIQRBLF (SEQ ID NO: 20)
LSQEQLEHRERSXQTLXDIQRBLF (SEQ ID NO: 21)
LSQEQLEHRERSLXTLRXIQRBLF (SEQ ID NO: 22)
LSQEQLEHRERSLQXLRDXQRBLF (SEQ ID NO: 23)
LSQEQLEHRERSLQTXRDIXRBLF (SEQ ID NO: 24)
LSQEQLEHRERSLQTLXDIQXBLF (SEQ ID NO: 25)
LSQEQLEHRERSLQTLRXIQRXLF (SEQ ID NO: 26)
LSQEQLEHRERSLQTLRDXQRBXF (SEQ ID NO: 27)
LSQEQLEHRERSLQTLRDIXRBLX i, i + 7 staples:

(SEQ ID NO: 28)
XSQEQLEXRERSLQTLRDIQRBLF (SEQ ID NO: 29)
LXQEQLEHXERSLQTLRDIQRBLF (SEQ ID NO: 30)
LSXEQLEHRXRSLQTLRDIQRBLF (SEQ ID NO: 31)
LSQXQLEHREXSLQTLRDIQRBLF (SEQ ID NO: 32)
LSQEXLEHRERXLQTLRDIQRBLF (SEQ ID NO: 33)
LSQEQXEHRERSXQTLRDIQRBLF (SEQ ID NO: 34)
LSQEQLXHRERSLXTLRDIQRBLF (SEQ ID NO: 35)
LSQEQLEXRERSLQXLRDIQRBLF (SEQ ID NO: 36)
LSQEQLEHXERSLQTXRDIQRBLF (SEQ ID NO: 37)
LSQEQLEHRXRSLQTLXDIQRBLF (SEQ ID NO: 38)
LSQEQLEHREXSLQTLRXIQRBLF (SEQ ID NO: 39)
LSQEQLEHRERXLQTLRDXQRBLF (SEQ ID NO: 40)
LSQEQLEHRERSXQTLRDIXRBLF (SEQ ID NO: 41)
LSQEQLEHRERSLXTLRDIQXBLF (SEQ ID NO: 42)
LSQEQLEHRERSLQXLRDIQRXLF (SEQ ID NO: 43)
LSQEQLEHRERSLQTXRDIQRBXF (SEQ ID NO: 44)
LSQEQLEHRERSLQTLXDIQRBLX i, i + 3 single staples:

(SEQ ID NO: 45)
XSQXQLEHRERSLQTLRDIQRBLF (SEQ ID NO: 46)
LXQEXLEHRERSLQTLRDIQRBLF (SEQ ID NO: 47)
LSXEQXEHRERSLQTLRDIQRBLF (SEQ ID NO: 48)
LSQEXLEXRERSLQTLRDIQRBLF (SEQ ID NO: 49)
LSQEQXEHXERSLQTLRDIQRBLF (SEQ ID NO: 50)
LSQEQLXHRXRSLQTLRDIQRBLF (SEQ ID NO: 51)
LSQEQLEXREXSLQTLRDIQRBLF (SEQ ID NO: 52)
LSQEQLEHXERXLQTLRDIQRBLF (SEQ ID NO: 53)
LSQEQLEHRXRSXQTLRDIQRBLF (SEQ ID NO: 54)
LSQEQLEHREXSLXTLRDIQRBLF (SEQ ID NO: 55)
LSQEQLEHRERXLQXLRDIQRBLF (SEQ ID NO: 56)
LSQEQLEHRERSXQTXRDIQRBLF (SEQ ID NO: 57)
LSQEQLEHRERSLXTLXDIQRBLF (SEQ ID NO: 58)
LSQEQLEHRERSLQXLRXIQRBLF (SEQ ID NO: 59)
LSQEQLEHRERSLQTXRDXQRBLF

```
                                  (SEQ ID NO: 60)
LSQEQLEHRERSLQTLXDIXRBLF (SEQ ID NO: 61)
LSQEQLEHRERSLQTLRXIQXBLF (SEQ ID NO: 62)
LSQEQLEHRERSLQTLRDXQRXLF (SEQ ID NO: 63)
LSQEQLEHRERSLQTLRDIXRBXF (SEQ ID NO: 64)
LSQEQLEHRERSLQTLRDIQXBLX.
```

13. The method of claim 1, wherein the structurally constrained peptide of BCL9-HD2 comprises two hydrocarbon staples and the two hydrocarbon staples are located at any of the positions within any one of the following BCL9 HD2 stapled peptides:

```
    i, i + 3 double staples:
                                  (SEQ ID NO: 65)
XSQXQLEHRERSLQTLRDIQXBLX (SEQ ID NO: 66)
XSQXQLEHRERSLQTLRDIXRBXF (SEQ ID NO: 67)
XSQXQLEHRERSLQTLRDXQRBXF i, i + 4 double staples:
                                  (SEQ ID NO: 68)
XSQEXLEHRERSLQTLRDIXRBLX (SEQ ID NO: 69)
XSQEXLEHRERSLQTLRDXQRBXF (SEQ ID NO: 70)
XSQEXLEHRERSLQTLXDIQRXLF i, i + 7 double staples:
                                  (SEQ ID NO: 71)
XSQEQLEXRERSLQTLXDIQRBLX (SEQ ID NO: 72)
XSQEQLEXRERSLQTXRDIQRBXF (SEQ ID NO: 73)
XSQEQLEXRERSLQXLRDIQRXLF.
```

14. The method of claim 1, wherein the at least one hydrocarbon staple is located at any of the positions within any one of the following BCL9 HD2 stapled peptides:

```
Mixed i, i + 4; i, i + 3; and i, i + 7
double staples:
                                  (SEQ ID NO: 74)
XSQEXLEHRERSLQTLXDIQRBLX (SEQ ID NO: 75)
XSQEXLEHRERSLQTXRDIQRBXF (SEQ ID NO: 76)
XSQEXLEHRERSLQXLRDIQRXLF (SEQ ID NO: 77)
XSQEXLEHRERSLQTLRDIQXBLX (SEQ ID NO: 78)
XSQEXLEHRERSLQTLRDIXRBXF (SEQ ID NO: 79)
XSQEXLEHRERSLQTLRDXQRXLF (SEQ ID NO: 80)
XSQEQLEXRERSLQTLRDIXRBLX (SEQ ID NO: 81)
XSQEQLEXRERSLQTLRDXQRBXF (SEQ ID NO: 82)
XSQEQLEXRERSLQTLRXIQRXLF (SEQ ID NO: 83)
XSQEQLEXRERSLQTLRDIQXBLX (SEQ ID NO: 84)
XSQEQLEXRERSLQTLRDIXRBXF (SEQ ID NO: 85)
XSQEQLEXRERSLQTLRDXQRXLF (SEQ ID NO: 86)
XSQXQLEHRERSLQTLRDIXRBLX (SEQ ID NO: 87)
XSQXQLEHRERSLQTLRDXQRBXF (SEQ ID NO: 88)
XSQXQLEHRERSLQTLRXIQRXLF (SEQ ID NO: 89)
XSQXQLEHRERSLQTLXDIQRBLX (SEQ ID NO: 90)
XSQXQLEHRERSLQTXRDIQRBXF (SEQ ID NO: 91)
XSQXQLEHRERSLQXLRDIQRXLF Sequential i, i + 4 staples:
                                  (SEQ ID NO: 92)
XSQEXLEHXERSLQTLRDIQRBLF (SEQ ID NO: 93)
LXQEQXEHRXRSLQTLRDIQRBLF (SEQ ID NO: 94)
LSXEQLXHREXSLQTLRDIQRBLF (SEQ ID NO: 95)
LSQXQLEXRERXLQTLRDIQRBLF (SEQ ID NO: 96)
LSQEXLEHXERSXQTLRDIQRBLF (SEQ ID NO: 97)
LSQEQXEHRXRSLXTLRDIQRBLF (SEQ ID NO: 98)
LSQEQLXHREXSLQXLRDIQRBLF (SEQ ID NO: 99)
LSQEQLEXRERXLQTXRDIQRBLF (SEQ ID NO: 100)
LSQEQLEHXERSXQTLXDIQRBLF (SEQ ID NO: 101)
LSQEQLEHRXRSLXTLRXIQRBLF (SEQ ID NO: 102)
LSQEQLEHREXSLQXLRDXQRBLF (SEQ ID NO: 103)
LSQEQLEHRERXLQTXRDIXRBLF (SEQ ID NO: 104)
LSQEQLEHRERSXQTLXDIQXBLF (SEQ ID NO: 105)
LSQEQLEHRERSLXTLRXIQRXLF (SEQ ID NO: 106)
LSQEQLEHRERSLQXLRDXQRBLF
```

-continued

LSQEQLEHRERSLQTXRDIXRBLX (SEQ ID NO: 107)

Sequential i, i + 3 staples:

XSQXQLXHRERSLQTLRDIQRBLF (SEQ ID NO: 108)

Sequential i, i + 7 staples:

XSQEQLEXRERSLQXLRDIQRBLF (SEQ ID NO: 109)

Mixed sequential staples:

XSQXQLEXRERSLQTLRDIQRBLF (SEQ ID NO: 110)

XSQXQLEHREXSLQTLRDIQRBLF (SEQ ID NO: 111)

XSQEXLEXRERSLQTLRDIQRBLF (SEQ ID NO: 112)

XSQEXLEHRERXLQTLRDIQRBLF (SEQ ID NO: 113)

XSQEQLEXREXSLQTLRDIQRBLF (SEQ ID NO: 114)

XSQEQLEXRERXLQTLRDIQRBLF. (SEQ ID NO: 115)

15. The method of claim 1, wherein the structurally constrained peptide comprises an amino acid sequence selected from the group consisting of:

SAH-BCL9$_A$:

LSQEQLEHRERSLQTLRXIQRXLF; (SEQ ID NO: 3)

SAH-BCL9$_B$:

LSQEQLEHRERSLXTLRXIQRBLF; (SEQ ID NO: 4)

and

SAH-BCL9$_C$:

LSQEQLEHREXSLQXLRDIQRBLF. (SEQ ID NO: 5)

16. The method of claim 15, wherein the structurally constrained peptide comprises the amino acid sequence of SEQ ID NO: 3.

17. The method of claim 15, wherein the structurally constrained peptide comprises the amino acid sequence of SEQ ID NO: 4.

* * * * *